(12) United States Patent
Tadano et al.

(10) Patent No.: US 11,484,224 B2
(45) Date of Patent: Nov. 1, 2022

(54) GAIT ANALYSIS METHOD AND GAIT ANALYSIS SYSTEM

(71) Applicants: NIPRO CORPORATION, Osaka (JP); HARADA ELECTRONICS INDUSTRY CO., LTD., Sapporo (JP)

(72) Inventors: Shigeru Tadano, Sapporo (JP); Ryo Takeda, Sapporo (JP); Harukazu Tohyama, Sapporo (JP); Yoshihiko Sano, Osaka (JP); Masahide Harada, Sapporo (JP)

(73) Assignees: NIPRO CORPORATION, Osaka (JP); HARADA ELECTRONICS INDUSTRY CO., LTD., Sapporo (JP)

( * ) Notice: Subject to any disclaimer, the term of this patent is extended or adjusted under 35 U.S.C. 154(b) by 959 days.

(21) Appl. No.: 15/746,656

(22) PCT Filed: Jul. 22, 2016

(86) PCT No.: PCT/JP2016/071512
§ 371 (c)(1),
(2) Date: Jan. 22, 2018

(87) PCT Pub. No.: WO2017/014294
PCT Pub. Date: Jan. 26, 2017

(65) Prior Publication Data
US 2018/0220935 A1 Aug. 9, 2018

(30) Foreign Application Priority Data
Jul. 23, 2015 (JP) ............................. JP2015-145395

(51) Int. Cl.
*A61B 5/00* (2006.01)
*A61B 5/11* (2006.01)

(52) U.S. Cl.
CPC ................ *A61B 5/112* (2013.01); *A61B 5/11* (2013.01); *A61B 5/1116* (2013.01); *A61B 5/1122* (2013.01); *A61B 2562/0219* (2013.01)

(58) Field of Classification Search
CPC ......... A61B 5/112; A61B 5/1122; A61B 5/11; A61B 5/1116; A61B 2562/0219
(Continued)

(56) References Cited

U.S. PATENT DOCUMENTS 5,808,433 A * 9/1998 Tagami ................ B62D 57/032
180/8.6
7,972,246 B2 * 7/2011 Shinomiya ........... A61B 5/1038
482/8

(Continued)

FOREIGN PATENT DOCUMENTS

JP 2006-068312 A 3/2006
JP 2011-092274 A 5/2011
(Continued)

OTHER PUBLICATIONS

Tanawongsuwan, R., & Bobick, A. (Dec. 2001). Gait recognition from time-normalized joint-angle trajectories in the walking plane. In Proceedings of the 2001 IEEE Computer Society Conference on Computer Vision and Pattern Recognition. CVPR 2001 (vol. 2, pp. II-II). IEEE. (Year: 2001).*

(Continued)

*Primary Examiner* — May A Abouelela
(74) *Attorney, Agent, or Firm* — Oliff PLC

(57) ABSTRACT

A triaxial acceleration sensor and a triaxial angular rate sensor are mounted on each of the lower limb portions on both sides of one joint among joints constituting a part of one lower limb of a subject. The acceleration and angular rate of each lower limb portion are measured by the triaxial acceleration sensor and triaxial angular rate sensor while the (Continued)

subject is walking. The orientations of each lower limb portion while walking are calculated on the basis of the measured acceleration and angular rate. A three-dimensional model including the motion trajectory of one joint is constructed by linking the lower limb portions in the calculated orientation to each other. The angle formed by the acceleration vector of one joint when the heel strikes the ground to the movement trajectory in the sagittal plane is calculated as a gait parameter.

16 Claims, 32 Drawing Sheets

(58) Field of Classification Search
USPC .......................................................... 600/595
See application file for complete search history.

(56) References Cited

U.S. PATENT DOCUMENTS

| | | | |
|---|---|---|---|
| 10,285,628 B2* | 5/2019 | Ichikawa | A61B 5/725 |
| 2005/0004495 A1* | 1/2005 | Goswami | A61B 5/4528 |
| | | | 600/595 |
| 2007/0091091 A1* | 4/2007 | Gardiner | G06T 11/206 |
| | | | 345/440 |
| 2009/0318779 A1* | 12/2009 | Tran | A61B 5/411 |
| | | | 600/595 |
| 2010/0184563 A1* | 7/2010 | Molyneux | A63B 24/0021 |
| | | | 482/1 |
| 2013/0123669 A1* | 5/2013 | Kinoshita | A61B 5/112 |
| | | | 600/595 |
| 2013/0130843 A1* | 5/2013 | Burroughs | A43B 5/02 |
| | | | 473/415 |
| 2013/0131555 A1* | 5/2013 | Hook | A61B 5/1121 |
| | | | 600/595 |
| 2014/0066816 A1* | 3/2014 | McNames | A61B 5/6831 |
| | | | 600/595 |
| 2015/0100251 A1* | 4/2015 | Solinsky | A63B 24/0006 |
| | | | 702/33 |
| 2015/0133821 A1* | 5/2015 | Pusch | A61B 5/4585 |
| | | | 600/595 |
| 2015/0173654 A1* | 6/2015 | Belanger | A61B 5/7246 |
| | | | 600/301 |
| 2015/0196231 A1* | 7/2015 | Ziaie | A61B 5/112 |
| | | | 600/595 |
| 2016/0015299 A1* | 1/2016 | Chan | A61B 5/683 |
| | | | 600/595 |
| 2016/0029928 A1* | 2/2016 | Jang | A61H 3/00 |
| | | | 600/595 |
| 2016/0038059 A1* | 2/2016 | Asada | A61B 5/6823 |
| | | | 600/595 |
| 2016/0038788 A1* | 2/2016 | McMillan | G01L 5/03 |
| | | | 73/488 |
| 2016/0045140 A1* | 2/2016 | Kitamura | A61B 5/1128 |
| | | | 600/595 |
| 2016/0249829 A1* | 9/2016 | Trabia | A61B 5/112 |
| | | | 600/592 |
| 2016/0249833 A1* | 9/2016 | Ronchi | G01C 22/006 |
| | | | 702/141 |
| 2016/0258779 A1* | 9/2016 | Hol | A61B 5/1121 |
| 2017/0027803 A1* | 2/2017 | Agrawal | A61B 5/1122 |
| 2017/0055880 A1* | 3/2017 | Agrawal | A43B 3/38 |
| 2017/0225033 A1* | 8/2017 | Czaja | A43B 5/04 |
| 2018/0020950 A1* | 1/2018 | Finch | A61B 5/6829 |
| | | | 600/595 |
| 2018/0361221 A1* | 12/2018 | Czaja | H04W 4/38 |
| 2019/0017007 A1* | 1/2019 | San | A01K 15/02 |
| 2020/0093400 A1* | 3/2020 | Hamner | A43B 3/0005 |

FOREIGN PATENT DOCUMENTS

| | | |
|---|---|---|
| JP | 2015-009032 A | 1/2015 |
| WO | 2016/088842 A1 | 6/2016 |

OTHER PUBLICATIONS

Miyagawa, Hiroaki et. al., "3-Dimensional Gait Analysis using Wearable Acceleration and Gyro Sensors", Proceedings of the Japan Society of Mechanical Engineers Annular Meeting of 2010, vol. 5, pp. 63-64, (2010).
Tadano, Shigeru et. al., "Gait Characterization for Osteoarthritis Patients Using Wearable Gait Sensors (H-Gait Systems)", Journal of Biomechanics, (Mar. 21, 2016), vol. 49, pp. 684-690.
Morris, J. R. W., "Accelerometry—A Technique for the Measurement of Human Body Movements", Journal of Biomechanics, vol. 6, pp. 729-736, (1973).
Liu, Tao et. al., "Development of a Wearable Sensor System for Quantitative Gait Analysis", Measurement, vol. 42, Issue 7, pp. 978-988, (2009).
Picerno, Pietro et. al., "Joint Kinematics Estimate Using Wearable Inertial and Magnetic Sensing Modules", Gait & Posture, vol. 28, pp. 588-595, (2008).
Takeda, Ryo et. al., "Gait Analysis Using Gravitational Acceleration Measured by Wearable Sensors", Journal of Biomechanics, vol. 42, Issue 3, pp. 223-233, (2009).
Takeda, Ryo et. al., "Gait Posture Estimation Using Wearable Acceleration and Gyro Sensors", Journal of Biomechanics, vol. 42, Issue 15, pp. 2486-2494, (2009).
Sep. 13, 2016 Search Report issued in International Patent Application No. PCT/JP2016/071512.
Jan. 23, 2018 International Preliminary Report on Patentability issued in International Patent Application No. PCT/JP2016/071512.

* cited by examiner (a)

(b)

(a) (b)

(a) (b)

(a)    (b)

(a)

(b)

GAIT ANALYSIS METHOD AND GAIT ANALYSIS SYSTEM

TECHNICAL FIELD

The present invention relates to a gait analysis method and a gait analysis system using a body-worn sensor (also referred to as a "wearable sensor"), and particularly to a gait analysis method and a gait analysis system for calculating novel gait parameters useful for assessment of gait action.

BACKGROUND ART

Measurement of gait action is used to assess gait abilities, to plan treatments, and to assess treatments in a quantitative manner. Conventionally, examples of general systems for gait measurement with an instrument include an optical three-dimensional motion analysis system. The measurement environment is subject to restrictions, generally requiring a long time for analysis. Therefore, the optical three-dimensional motion analysis system is only used in the area of research, and it is difficult to say that the optical three-dimensional motion analysis system has been in clinical use sufficiently.

In recent years, development and research of a gait measurement system capable of easier measurement has drawn attention. In the past, gait measurement using an acceleration sensor attached to a human body was proposed by Morris (Non-Patent Literature 1). Since then, measurement methods using a small-sized sensor, e.g., an acceleration sensor or an angular velocity sensor, have been researched (Non-Patent Literature 1 to 3). Thus, restrictions on measurement environments and a long required time, which were the problems with the conventional system, have been overcome, and it can be said that the practicability in clinical use has been increased.

However, most of the reports about sensor systems such as those described above indicate a mere acceleration comparison or two-dimensional gait measurement in which gait is recognized as a plane motion. A three-dimensional gait measurement system using a small-sized sensor has not been achieved.

Given the above, the inventors of the present application have pursued the development of a three-dimensional gait analysis using an acceleration sensor and an angular velocity sensor (Non-Patent Literature 4 and 5). As a result, the inventors of the present application have succeeded to measure a three-dimensional motion considering rotation of a joint with high precision by means of an analysis method using quaternion calculation (Non-Patent Literature 6).

CITATION LIST

Non-Patent Literature

Non-Patent Literature 1: Morris, J. R. W.; Accelerometry—a technique for the measurement of human body movements, Journal of Biomechanics 6, 729-736, (1973)

Non-Patent Literature 2: Tao Liu, Yoshio Inoue, Kyoko Shibata: Development of a wearable sensor system for quantitative gait analysis, Measurement, Volume 42, Issue 7, 978-988, (2009)

Non-Patent Literature 3: Pietro Picerno, Andrea Cereatti, Aurelio Cappozzo: Joint kinematics estimate using wearable inertial and magnetic sensing modulues, Gait & Posture 28, 588-595, (2008)

Non-Patent Literature 4: Ryo Takeda, Shigeru Tadano, Masahiro Todoh, Manabu Morikawa, Minoru Nakayasu, Satoshi Yoshinari: Gait analysis using gravitational acceleration measured by wearable sensors, Journal of Biomechanics, Volume 42, Issue 3, 223-233, (2009)

Non-Patent Literature 5: Ryo Takeda, Shigeru Tadano, Akiko Natorigawa, Masahiro Todoh, Satoshi Yoshinari: Gait posture estimation using wearable acceleration and gyro sensors, Journal of Biomechanics, Volume 42, Issue 15, 2486-2494, (2009)

Non-Patent Literature 6: Hiroaki Miyagawa, Ryo Takeda, ShigeruTadano: *Kasokudo-Kakusokudo Sensa Ni Yoru Sanjigen Hoko Kaiseki* (Three-dimensional gait analysis using acceleration and angular velocity sensors), Proceedings of the Japan Society of Mechanical Engineers annular meeting of 2010, Vol. 5: 63-64, 2010

SUMMARY OF INVENTION

Technical Problem

It is an object of the present invention to develop the conventional three-dimensional gait analysis using an acceleration sensor and an angular velocity sensor to provide a gait analysis method and a gait analysis system that can obtain novel gait parameters useful for assessment of gait actions of a subject.

Solution to Problem

The present invention solves the aforementioned problem, and a gait analysis method of the present invention is characterized in that a tri-axial acceleration sensor and a tri-axial angular velocity sensor are attached to lower limb portions across at least one joint of joints constituting at least one of lower limbs of a subject, acceleration and angular velocity of each lower limb portion are respectively measured with the tri-axial acceleration sensor and the tri-axial angular velocity sensor during gait of the subject, the posture of each lower limb portion during the gait is calculated on the basis of the acceleration and the angular velocity measured, the lower limb portions in the calculated posture are coupled to one another to construct a three-dimensional model including a motion trajectory of the at least one joint, and an angle of an acceleration vector of the at least one joint at the time of heel contact with regard to the motion trajectory in a sagittal plane is calculated as a gait parameter.

A gait analysis system of the present invention is characterized by including a tri-axial acceleration sensor and a tri-axial angular velocity sensor attached to lower limb portions across at least one joint of joints constituting at least one of lower limbs of a subject to respectively measure acceleration and angular velocity of each lower limb portion during gait of the subject, a model construction means for calculating the posture of each lower limb portion during the gait on the basis of the acceleration and the angular velocity measured and constructing a three-dimensional model including a motion trajectory of the at least one joint by coupling the lower limb portions in the calculated posture to one another, and a gait parameter calculation means for calculating an angle of an acceleration vector of the at least one joint at the time of heel contact with regard to the motion trajectory in a sagittal plane as a gait parameter.

Advantageous Effect of Invention

With the gait analysis method and the gait analysis system according to the present invention, a three-dimensional model including a motion trajectory of at least one joint is constructed on the basis of acceleration data and angular velocity data of each lower limb portion during gait of a subject, and an angle formed by the motion trajectory and an acceleration vector of a joint at the time of heel contact is calculated, enabling determination of novel gait parameters useful for gait analysis.

In the gait analysis method of the present invention, the at least one joint may be a knee joint.

In addition, in the gait analysis method of the present invention, the three-dimensional model including the motion trajectory of at least one joint maybe constructed with respect to each of right and left lower limbs of the subject.

Furthermore, in the gait analysis method of the present invention, approximation straight lines may be formed with respect to the motion trajectories of right and left joints in a horizontal plane, and an angle formed between the approximation straight lines may be calculated as a gait parameter.

Furthermore, in the gait analysis method of the present invention, a Lissajous figure of a joint may be created from a three-dimensional model, and a gait parameter may be calculated on the basis of the Lissajous figure.

In addition, the gait analysis system of the present invention may be configured such that the tri-axial acceleration sensor and the tri-axial angular velocity sensor are attached to the right and left lower limbs of a subject, the gait parameter calculation means forms approximation straight lines with respect to the motion trajectories of the right and left joints in a horizontal plane, and calculates an angle formed between the approximation straight lines as a gait parameter.

Furthermore, the gait analysis system of the present invention may be configured such that the parameter calculation means creates a Lissajous figure of a joint from a three-dimensional model and calculates a gait parameter on the basis of the Lissajous figure.

BRIEF DESCRIPTION OF DRAWINGS

of a right leg in a sagittal plane, FIG. 31(c) is a graph illustrating motion trajectories of joints (great trochanter, knee joint, ankle joint) of a left leg in a sagittal plane, and FIG. 31(d) is a graph illustrating motion trajectories of knee joints in a horizontal plane.

FIG. 32(a) is a graph illustrating a knee flexion angle, FIG. 32(b) is a graph illustrating motion trajectories of joints (great trochanter, knee joint, ankle joint) of a right leg in a sagittal plane, FIG. 32(c) is a graph illustrating motion trajectories of joints (great trochanter, knee joint, ankle joint) of a left leg in a sagittal plane, and FIG. 32(d) is a graph illustrating motion trajectories of knee joints in a horizontal plane.

FIG. 33(a) is a graph illustrating a knee flexion angle, FIG. 33(b) is a graph illustrating motion trajectories of joints (great trochanter, knee joint, ankle joint) of a right leg in a sagittal plane, FIG. 33(c) is a graph illustrating motion trajectories of joints (great trochanter, knee joint, ankle joint) of a left leg in a sagittal plane, and FIG. 33(d) is a graph illustrating motion trajectories of knee joints in a horizontal plane.

FIG. 34(a) is a graph illustrating a knee flexion angle, FIG. 34(b) is a graph illustrating motion trajectories of joints (great trochanter, knee joint, ankle joint) of a right leg in a sagittal plane, FIG. 34(c) is a graph illustrating motion trajectories of joints (great trochanter, knee joint, ankle joint) of a left leg in a sagittal plane, and FIG. 34(d) is a graph illustrating motion trajectories of knee joints in a horizontal plane.

FIG. 35(a) is a graph illustrating a knee flexion angle, FIG. 35(b) is a graph illustrating motion trajectories of joints (great trochanter, knee joint, ankle joint) of a right leg in a sagittal plane, FIG. 35(c) is a graph illustrating motion trajectories of joints (great trochanter, knee joint, ankle joint) of a left leg in a sagittal plane, and FIG. 35(d) is a graph illustrating motion trajectories of knee joints in a horizontal plane.

FIG. 36(a) is a graph illustrating a knee flexion angle, FIG. 36(b) is a graph illustrating motion trajectories of joints (great trochanter, knee joint, ankle joint) of a right leg in a sagittal plane, FIG. 36(c) is a graph illustrating motion trajectories of joints (great trochanter, knee joint, ankle joint) of a left leg in a sagittal plane, and FIG. 36(d) is a graph illustrating motion trajectories of knee joints in a horizontal plane.

FIG. 37(a) is a graph illustrating a knee flexion angle, FIG. 37(b) is a graph illustrating motion trajectories of joints (great trochanter, knee joint, ankle joint) of a right leg in a sagittal plane, FIG. 37(c) is a graph illustrating motion trajectories of joints (great trochanter, knee joint, ankle joint) of a left leg in a sagittal plane, and FIG. 37(d) is a graph illustrating motion trajectories of knee joints in a horizontal plane.

FIG. 38(a) is a graph illustrating a knee flexion angle, FIG. 38(b) is a graph illustrating motion trajectories of joints (great trochanter, knee joint, ankle joint) of a right leg in a sagittal plane, FIG. 38(c) is a graph illustrating motion trajectories of joints (great trochanter, knee joint, ankle joint) of a left leg in a sagittal plane, and FIG. 38(d) is a graph illustrating motion trajectories of knee joints in a horizontal plane.

FIG. 39(a) is a graph illustrating a knee flexion angle, FIG. 39(b) is a graph illustrating motion trajectories of joints (great trochanter, knee joint, ankle joint) of a right leg in a sagittal plane, FIG. 39(c) is a graph illustrating motion trajectories of joints (great trochanter, knee joint, ankle joint) of a left leg in a sagittal plane, and FIG. 39(d) is a graph illustrating motion trajectories of knee joints in a horizontal plane.

DESCRIPTION OF EMBODIMENT

Figure 1:
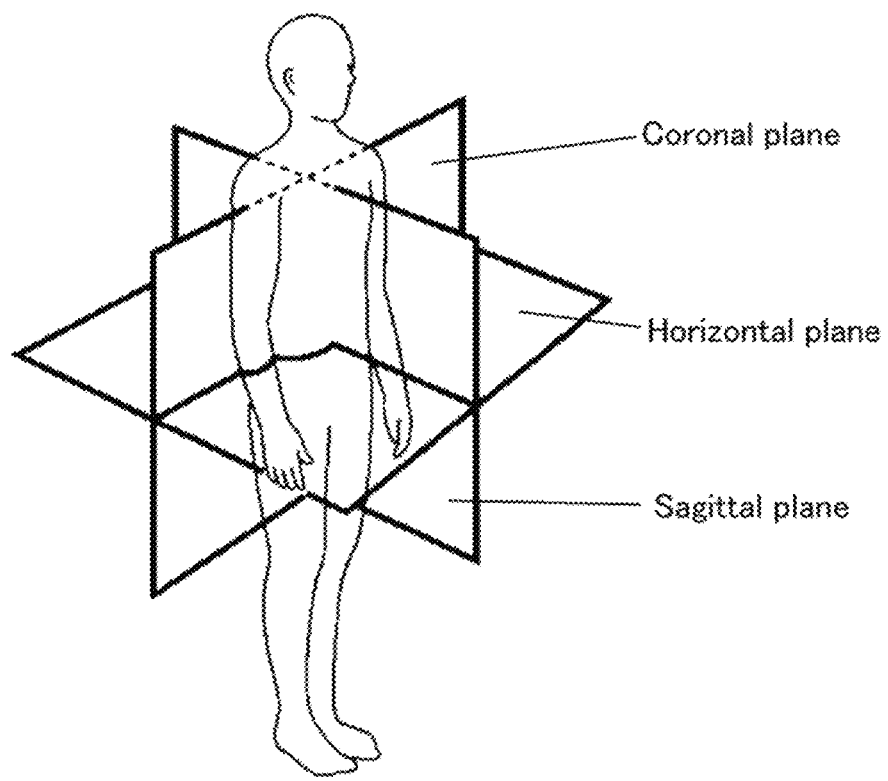
FIG. 1 is a view describing fundamental planes of a body motion.

First, terms and technical terms regarding gait used herein are described.
(1) Fundamental Planes of Body Motions
As illustrated in FIG. 1, there are three fundamental planes of a body motion as described below.
Horizontal plane
A plane dividing a body into upper and lower parts; also called a transverse plane.
Coronal plane
A plane dividing a body into front and rear parts.
Sagittal plane
A plane dividing a body into right and left parts.
(2) Axes of Body Motions
When a body motion is rotation, the body motion can be expressed with reference to an axis, not a plane. This is defined as follows:
   Median axis: A line segment common to a coronal plane and a sagittal plane.
   Frontal-horizontal axis: a line segment common to a coronal plane and a horizontal plane.
   Sagittal-horizontal axis: a line segment common to a sagittal plane and a horizontal plane.
(3) Motions of Lower Limb Joints
A motion of a lower limb joint and an average range of motion of a joint of a healthy person are described. (3-1) Motions of hip joints
A hip joint is a three-degree-of-freedom joint that enables flexion and extension motions, adduction and abduction motions, and internal rotation and external rotation motions.

Figure 2:
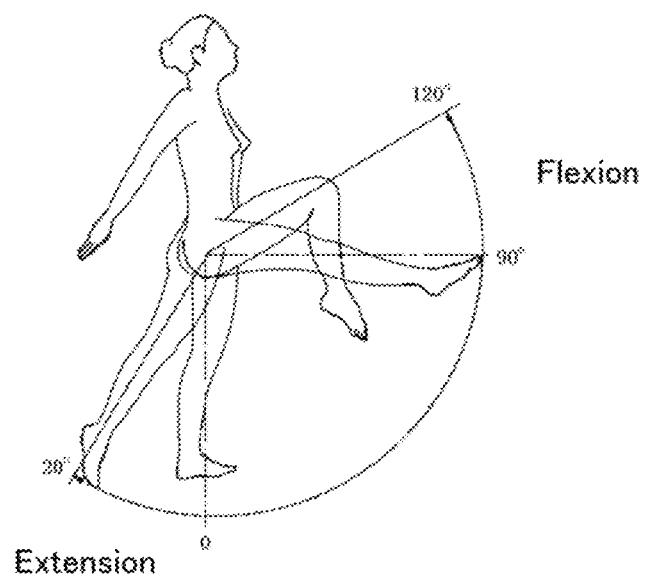
FIG. 2 is a view illustrating a direction of flexion and extension motions and a range of motion of a hip joint.

FIG. 2 illustrates a direction of flexion and extension motions and a range of motion of a hip joint. A direction in which a leg is swung forward is the flexion direction.

Figure 3:
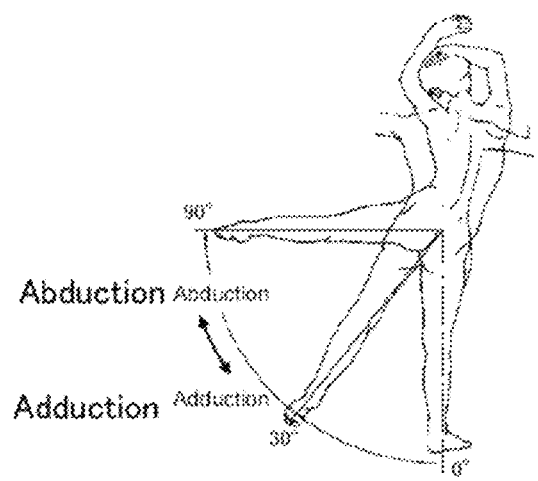
FIG. 3 is a view illustrating a direction of adduction and abduction motions and a range of motion of a hip joint.

FIG. 3 illustrates a direction of adduction and abduction motions and a range of motion of a hip joint. It is a rotation in the coronal plane in which a direction in which a foot approaches the median axis is the adduction and a direction in which a foot moves away from the median axis is the abduction.

Figure 4:
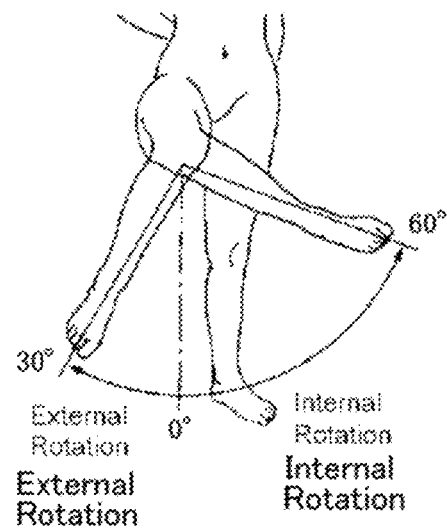
FIG. 4 is a view illustrating a direction of internal rotation and external rotation motions and a range of motion of a hip joint.

FIG. 4 illustrates a direction of internal rotation and external rotation motions and a range of motion of a hip joint. It is a rotation about an axis of a thigh. When a point is marked on a front surface of the thigh, a direction in which the point approaches the fundamental sagittal plane is the internal rotation and a direction in which the point moves away from the fundamental sagittal plane is the external rotation.

(3-2) Motions of Knee Joints

Figure 5:
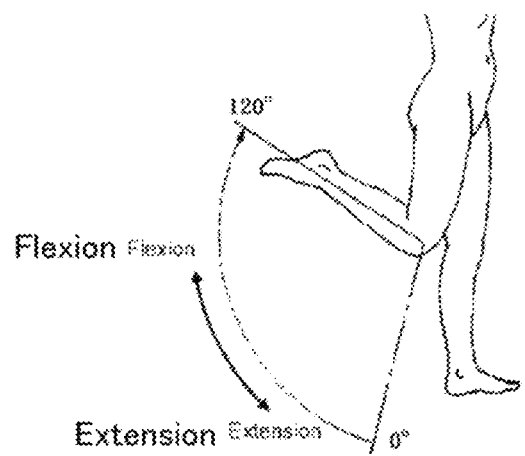
FIG. 5 is a view illustrating a direction of flexion and extension motions and a range of motion of a knee joint.

FIG. 5 illustrates a direction of flexion and extension and a range of motion. A direction in which a foot approaches buttocks is the flexion direction and a direction in which a foot moves away from buttocks is the extension direction. In the field of motion analysis, a knee joint is often considered a hinge joint. However, technically, the motion of a knee joint is not limited to flexion and extension, but the movable motion can be expanded in the adduction and abduction directions or in the internal rotation and external rotation directions due to impairment, e.g., damage to an anterior cruciate ligament. In the field of orthopedic surgery, the motion of a knee joint is generally treated three-dimensionally. Therefore, according to the present invention, a knee joint is treated as a spheroidal joint. A direction in which a knee joint has varus deformity (bowleg) is the adduction direction, and a direction in which a knee joint has valgus deformity (knock knee) is the abduction direction. A direction in which the front surface of a shank faces inward relative to the thigh is the internal rotation direction, and a direction in which the front surface of a shank faces outward is the external rotation direction.

(3-3) Motions of Ankle Joints

Figure 6:
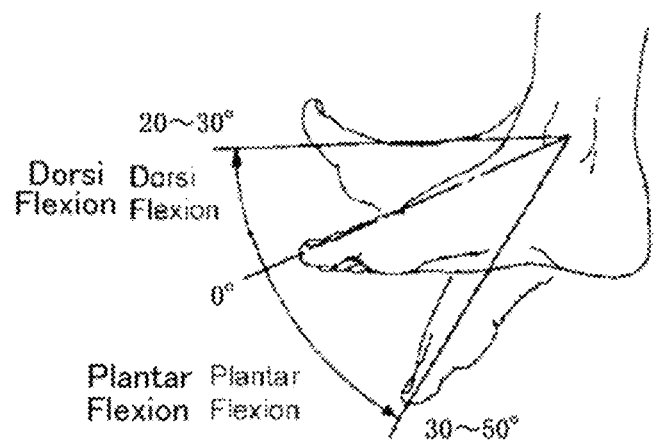
FIG. 6 is a view illustrating a direction of plantar flexion and dorsi flexion and a range of motion of an ankle joint.
Figure 7:
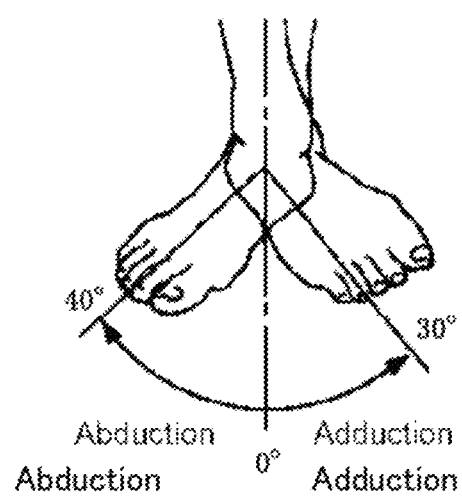
FIG. 7 is a view illustrating a direction of adduction and abduction and a range of motion of an ankle joint.

An ankle joint performs dorsi flexion and plantar flexion motions, and adduction and abduction motions. FIG. 6 illustrates a direction of plantar flexion and dorsi flexion, and a range of motion. A direction in which a toe is pressed down toward the sole is the plantar flexion direction, and an opposite direction is the dorsi flexion direction. FIG. 7 illustrates a direction of adduction and abduction and a range of motion. A direction in which a toe approaches the median axis is the adduction, and a direction in which a toe moves away from the median axis is the abduction.

(4) Time Factors of Gait

In the case of general gait, the heel contacts the ground first, and the toe leaves the ground last. In particular, an action in which a heel contacts the ground during gait is called heel contact or heel strike, and an action in which a toe leaves the ground is called toe off. A time required from the heel contact to the next heel contact of the same foot is called a gait cycle. The gait cycle is divided into a stance phase and a swing phase. The stance phase indicates a phase from the heel contact to the toe off, i.e., a state in which the foot is on the ground. The swing phase is a phase from the toe off to the heel contact, i.e., a state in which the foot is off the ground. In the case of healthy gait, the stance phase and the swing phase of the gait cycle account for about 60% and about 40%, respectively.

(5) Methods of Expressing Three-Dimensional Postures

Figure 8:
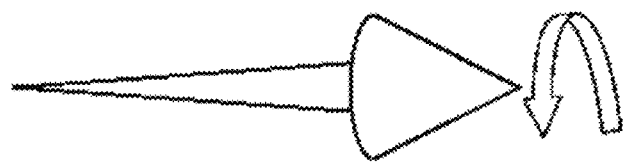
FIGS. 8(*a*) and (*b*) are views describing a method of expressing an orientation of an ordinate system of a three-dimensional space.
Figure 8:
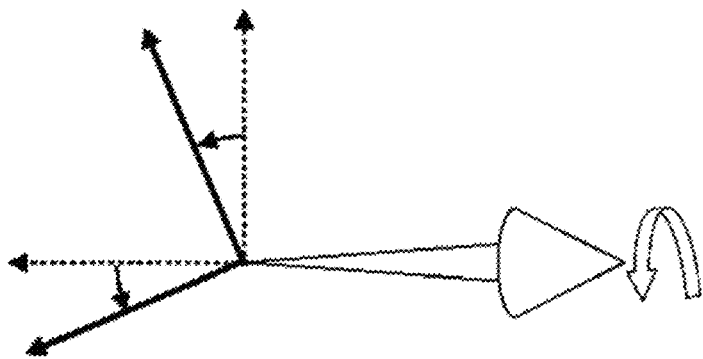

Herein, methods of expressing an "orientation (posture)" of a coordinate system in a three-dimensional space are described. Expressions of directions in a three-dimensional space include "direction" and "orientation". They differ, in short, in that the direction is the direction of a vector and the orientation is the posture of a coordinate system. For example, as illustrated in FIG. 8(*a*), a direction having a vector is illustrated. A rotation about the axis of the vector does not provide any apparent change. As illustrated in FIG. 8(*b*), an orientation having a coordinate system is illustrated. Even when a rotation is made about one basic axis therefrom, the rotation can be observed according to a change of the direction of another basic axis. When the relationship between the orientations of two coordinate systems can be expressed by conversion by means of a unit matrix E, the relationship between the two coordinate systems is said to be in an "identical state". In the identical state, the corresponding basic axes of the two coordinate systems are parallel to each other. An angular displacement from the identical state is called the orientation. The angular displacement indicates a quantity varying with rotation.

(6) Matrix

Figure 9:
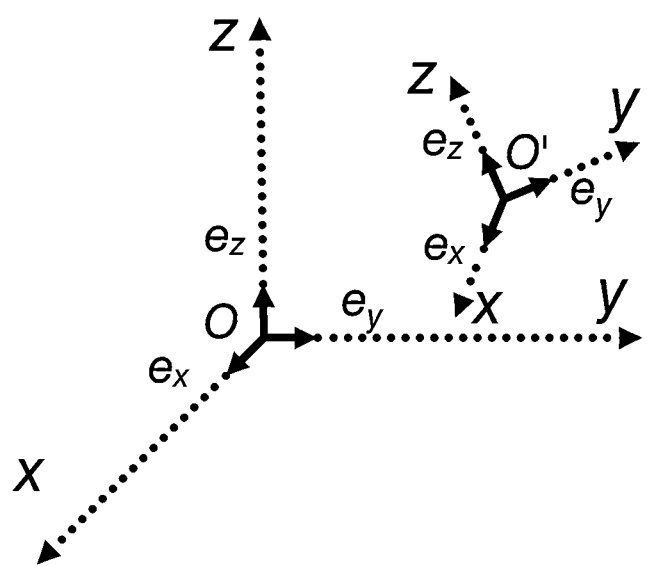
FIG. 9 is a view illustrating two coordinate systems in a three-dimensional space.

In a three-dimensional coordinate system, a general method of expressing the orientation in the field of mathematics is a matrix. A coordinate system O-XYZ and a coordinate system O'-xyz illustrated in FIG. 9 are considered in a three-dimensional space. The coordinate system O'-xyz can freely move in the coordinate system O-XYZ. At this time, the orientation of the coordinate system O'-xyz, which is observed from the coordinate system O-XYZ, is determined.

The coordinate system O'-xyz starts in the identical state with respect to the coordinate system O-XYZ, and predetermined rotation operation is performed. The orientation of the coordinate system O'-xyz as of the present time is illustrated. Now, when basic vectors $e_x$, $e_y$, $e_z$ of O'-xyz are known to be vectors of the coordinate system O-XYZ, a rotation matrix indicated in Equation (1) is determined from these three vectors.

[Equation 1]

$$R_{XYZ \to xyz} = [e_x e_y e_z] \tag{1}$$

By making use of the fact that Equation (1) is an orthogonal matrix, inverse conversion is determined by transposition of it.

[Equation 2]

$$R_{xyz \to XYZ} = [e_x e_y e_z] \tag{2}$$

(7) Euler Angles

As a general method of expressing the motion of a body, there is a concept called Euler angles. In the field of orthopedic surgery or biomechanics, the Euler angles are used with respect to the motion of a three-degree-of-freedom joint, e.g., a shoulder joint or a hip joint. The Euler angles are less used for those modeled as a joint with only flexion and extension motions, e.g., a knee joint.

Figure 10:
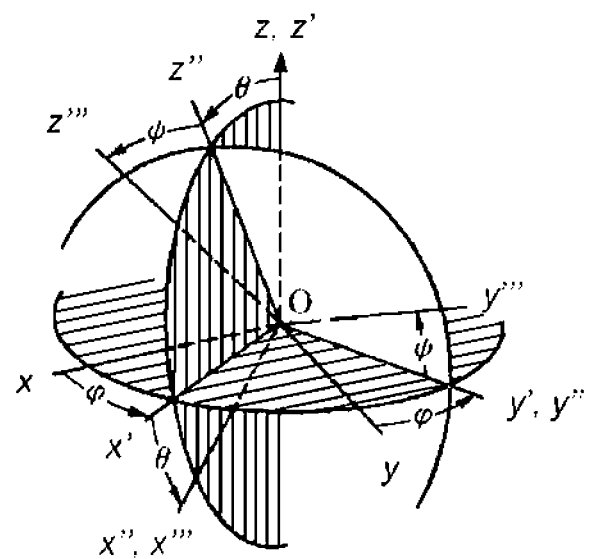
FIG. 10 is a view describing general Euler angles.

The Euler angles are named after Leonhard Euler, who proved that any orientation can be expressed by rotation of three different axes. There are many definitions of the Euler angles depending on the combination of an order of rotation. Three parameters expressing the amount of rotation depend on an order of rotation. For correct expression of the orientation, it is necessary to describe the definitions of the Euler angles to be used. The z-y-x Euler angles, general Euler angles, are introduced in conjunction with FIG. 10. First, a coordinate system in the identical state with the coordinate system O-xyz described in (6) above is considered. First, rotation at an angle φ about the z axis is performed. This is called a "heading angle". Next, rotation at an angle θ about the y axis after the rotation is performed. This is called a "pitch angle". Finally, rotation at an angle φ about the x axis after the above rotation is performed. This is called a "bank angle". Equation (3) indicates a rotation matrix of the z-y-x Euler angles.

[Equation 3]

$$R = R_z R_y R_x \tag{3}$$
$$= \begin{bmatrix} C\theta_z C\theta_y - S\theta_z S\theta_x S\theta_y & -S\theta_z C\theta_x & C\theta_z C\theta_y + S\theta_z S\theta_x S\theta_y \\ S\theta_z C\theta_y + C\theta_z S\theta_x S\theta_y & C\theta_z C\theta_x & S\theta_z C\theta_y - C\theta_z S\theta_x S\theta_y \\ -C\theta_z S\theta_y & S\theta_x & C\theta_x S\theta_y \end{bmatrix}$$

In Equation (3), symbols sin and cos are abbreviated as s and c, respectively. Symbols $R_x$, $R_y$ and $R_z$ are as described in Equations (4) to (6).

[Equation 4]
$$R_x = \begin{bmatrix} 1 & 0 & 0 \\ 0 & \cos\theta_x & -\sin\theta_x \\ 0 & \sin\theta_x & \cos\theta_x \end{bmatrix} \quad (4)$$

[Equation 5]
$$R_y = \begin{bmatrix} \cos\theta_y & 0 & \sin\theta_y \\ 0 & 1 & 0 \\ -\sin\theta_y & 0 & \cos\theta_y \end{bmatrix} \quad (5)$$

[Equation 6]
$$R_z = \begin{bmatrix} \cos\theta_z & -\sin\theta_z & 0 \\ \sin\theta_z & \cos\theta_z & 0 \\ 0 & 0 & 1 \end{bmatrix} \quad (6)$$

The rotations of the Euler angles in the case of inverse conversion, i.e., when rotation is performed in an order of x-y-z axes, are called a roll angle, a pitch angle, and a yaw angle, respectively. These are called Cardan angles, which are most frequently used in biomechanics.

The number of parameters minimally required for expression of a three-dimensional angular displacement is three. The Euler angles are expressed by minimally required three angles. In addition, such parameters are directly linked to angle data and are therefore very intuitive. However, the Euler angles are merely a forward kinematical "orientation expressing method", but are not a calculation method. Calculation is somewhat troublesome when an orientation indicated by certain Euler angles is changed to an orientation indicated by different Euler angles. In addition, there is also a problem called gimbal lock. Also from a viewpoint of algorithm construction, the Euler angles are not a preferable method because of conditional processing with regard to singularities and an increase in number of times of calculation as indicated by Equation (3).

(8) Quaternions

The quaternion is a type of "hypercomplex numbers", which is an extension of complex numbers. In recent years, the quaternion is applied to the field of 3D computer graphics and spacecraft attitude control.

The quaternion is formed of one scalar element and one vector element. As methods of expressing a quaternion, there are various methods including a method of expressing a quaternion as a matrix and a method of expressing a quaternion using an exponential map. Herein, the expression described below is used.

[Equation 7]
$$Q = W + X_i + Y_j + Z_k = (W; X, Y, Z) = (W; V) \quad (7)$$

Symbols W, X, Y and Z are quaternion parameters. Similar to V, symbols X, Y and Z can be expressed as vectors. When quaternions are used in an orientation expressing method, the quaternions are easier to understand as they are expressed as vectors. Symbols i, j and k are called quaternion units that are similar in property to imaginary numbers.

[Equation 8]
$$i^2 = j^2 = k^2 = ijk = -1 \quad (8)$$

The quaternion has a norm, which is defined in Equation (9).

[Equation 9]
$$|Q| = \sqrt{W^2 + X^2 + Y^2 + Z^2} \quad (9)$$

The quaternion having $\|Q\| = 1$ is particularly called a unit quaternion, which is indicated by Equation (10).

[Equation 10]
$$q = Q/\|Q\| = (w; x, y, z) \quad (10)$$

The quaternion is a type of hypercomplex numbers. Therefore, similar to complex numbers, there is a concept called a conjugate quaternion, which is indicated by Equation (11).

[Equation 11]
$$Q^* = (W; -V) \quad (11)$$

In the case of $q = (w_1; v_1)$ and $q_2 = (w_2; v_2)$, a product of the unit quaternions is indicated by Equation (12).

[Equation 12]
$$q_1 \otimes q_2 = (w_1; v_1) \otimes (w_2; v_2) = (w_1 w_2 - v_1 v_2;\ w_1 v_2 + w_2 v_1 + v_1 \times v_2) \quad (12)$$

A geometric significance of the quaternion is described. The unit quaternion indicating rotation can be indicated by Equation (13) using cos and sin.

[Equation 13]
$$q = \left(\cos\frac{\theta}{2};\ n\sin\frac{\theta}{2}\right) \quad (13)$$

Here, symbol n is a unit vector. Now, a vector r in a three-dimensional space is considered. This vector is indicated as $r = (0;\ r_x,\ r_y,\ r_z)$ in quaternion notation. A real component may be any value and here is zero for the sake of simplicity.

The rotation in a three-dimensional space can be expressed in conjunction with the description given heretofore. When r defined above is rotated to be r', this phenomenon can be expressed by Equation (14).

[Equation 14]
$$r' = q \otimes r \otimes q^* \quad (14)$$

In this case, the unit quaternions n and θ used for rotation indicated in Equation (13) indicate a vector indicating an axis of rotation and the amount of rotation about the axis, respectively.

According to the present invention, as will be described below, the quaternions are used for computation of angular displacement.

In view of the above, an embodiment of the present invention is described in detail on the basis of the drawings. A gait analysis system and a gait analysis method according to the embodiment measure acceleration and angular velocity of a body part during gait of a subject, estimates a lower limb posture on the basis of the measurement data, and calculates a gait parameter required for assessment of gait.

Figure 11:
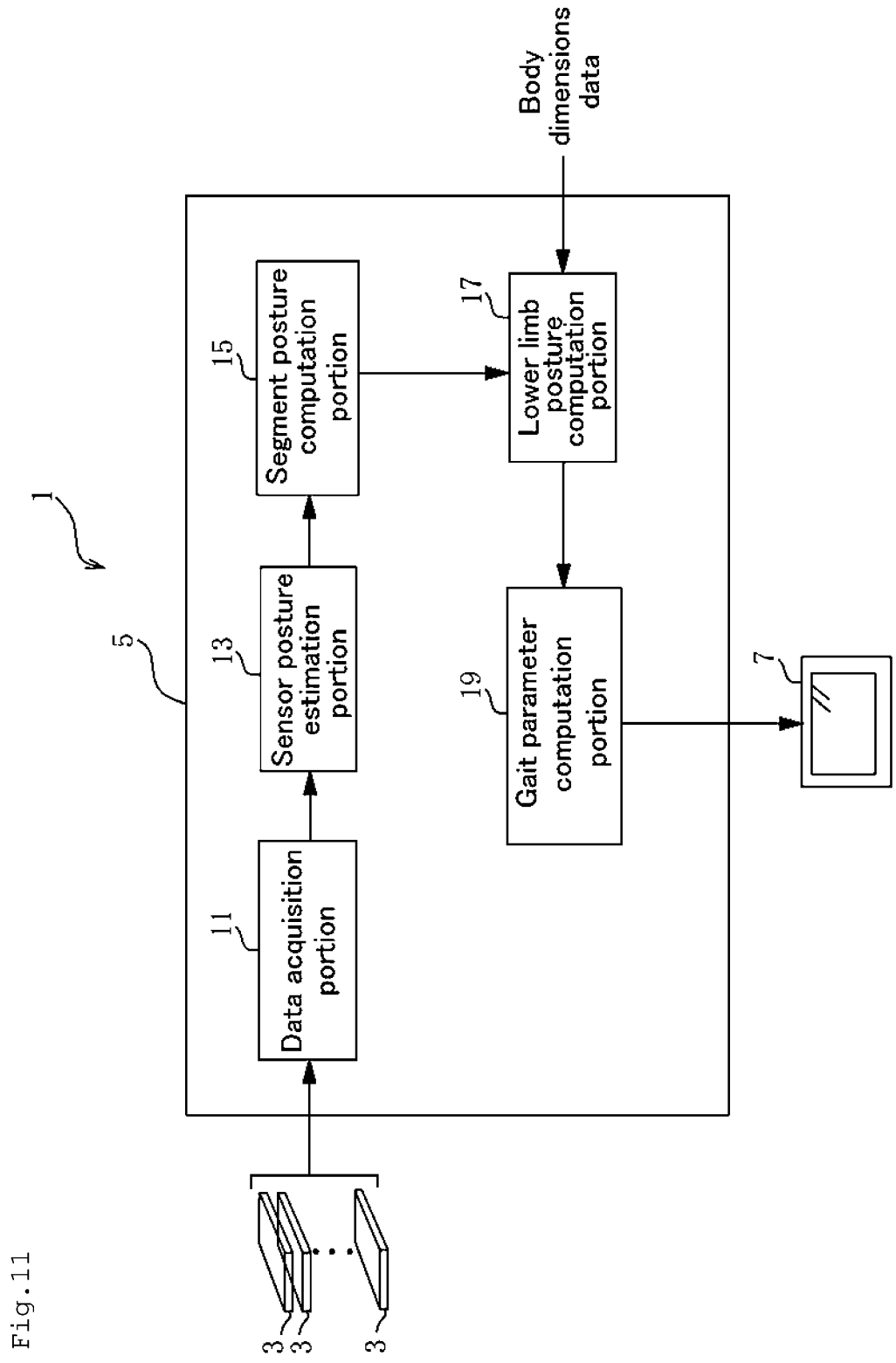
FIG. 11 is a block configurational diagram of a processing device of a gait analysis system according to an embodiment of the present invention.

As illustrated in FIG. 11, a gait analysis system 1 includes sensor units 3 for measuring acceleration and angular velocity of a body part during gait, a processing device 5 for acquiring acceleration data and angular velocity data from the sensor units 3 and executing processing of calculating a parameter for gait assessment, and a monitor screen 7 for displaying results of gait assessment.

(Sensor Units)

Each sensor unit 3 is formed as one tri-axial acceleration sensor, one bi-axial angular velocity sensor, and one uni-axial angular velocity sensor are configured as a unit. The sensor unit 3 detects acceleration of perpendicular three axial directions and angular velocity about the axes. The acceleration sensor and the angular velocity sensor may not be configured as a unit. As the sensor unit 3, for example, WAA-00 6 manufactured by Wireless Technologies, Inc. may be used. In the present embodiment, seven sensor units 3 are used. The attachment locations and the method will be described later.

Each sensor unit 3 is configured to transmit acceleration data and angular velocity data detected by the acceleration sensor and the angular velocity sensor, respectively, to the processing device 5 in real time via wireless communication. Each sensor unit 3 includes a software timer. At the timing of measurement of acceleration and angular velocity with the internal sensors, a timer value is stored together. Thus, all the sensor units are synchronized. A sampling frequency is set to 100 Hz.

Figure 12:
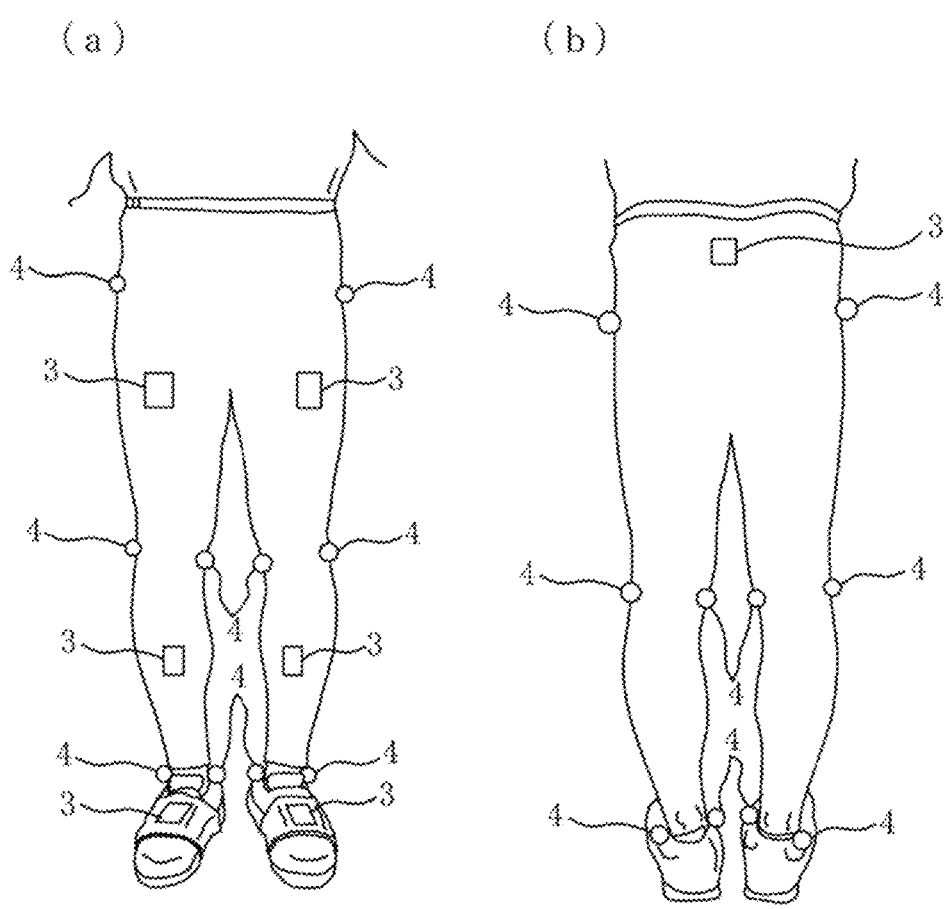
FIG. 12 is views illustrating a sensor attachment arrangement of a gait analysis system according to the aforementioned embodiment and a gait analysis method according to an embodiment of the present invention using the same, FIG. 12(*a*) is a front view, and FIG. 12(*b*) is a rear view.

FIGS. 12($a$) and ($b$) illustrate attachment positions and an attachment method for the sensor units 3 with respect to a subject (testee) at the time of data measurement. A total of seven sensor units 3 are attached to the pelvis, the right and left thighs, the right and left shanks, and the right and left feet, respectively. The sensor units 3 may be fixed in a predetermined position by being housed in pockets formed on sports tights or pockets formed on a sports band worn by a subject during gait. The sensor units 3 are not subjected to any particular limitation regarding fixing position, but may be arranged at any location on the aforementioned portions. However, in order to minimize the angular velocity that can be generated on the sensors by the muscle activity, it is preferable that the sensor unit 3 on the pelvis be fixed to the midpoint of the right and left posterior iliac crests, the sensor units 3 on the thighs be fixed to the quadriceps muscle middle portions, and the sensor units 3 on the shanks be attached to the inner sides of the front parts of the tibiae. The sensor units 3 on the feed can be fixed to the surfaces of shoes by means of a sports band or the like. However, it is preferable to avoid the vicinity of the metatarsal joint and to select proper locations to be free of influences by plantar and dorsi flexion. The directions of the sensor units 3 when fixed may be arbitrary because the directions are corrected by a method that will be described later. Incidentally, reference numeral 4 in the drawings indicates markers that will be described later.

(Modeling of Lower Limbs)

Figure 13:
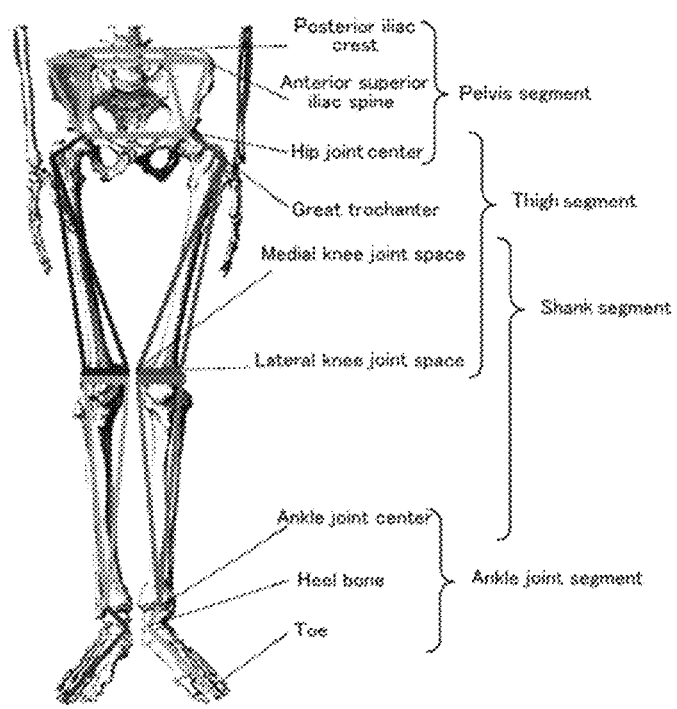
FIG. 13 is a view describing a wire-frame model of lower limbs according to the aforementioned embodiment.

Next, modeling of lower limbs is described. In the present embodiment, a three-dimensional wire-frame model such as that illustrated in FIG. 13 is constructed to express the posture of a body part during gait. This is an extension of a method of expressing a part of a body as a rigid body link model, and a plane is formed of wires. This enables expression of not only the directions, but also the posture (orientation) of a body part. Parts expressed by wires are regarded as rigid bodies, which are called segments for the sake of convenience. Each of the segments is capable of independent motion. The lower limb model is formed of a total of seven segments: a pelvis segment, right and left thigh segments, right and left shank segments, and right and left foot segments. The details are described below.

The pelvis segment is formed of six points: right and left anterior superior iliac spines, right and left posterior iliac crests, and right and left hip joint centers.

The thigh segment is formed of four points: a hip joint center, a great trochanter, a medial knee joint space, and a lateral knee joint space.

The shank segment is formed of a lateral condyle of tibia, a medial knee joint space, a lateral knee joint space, and an ankle joint center. The ankle joint center is a midpoint of the lateral malleolus and the medial malleolus.

The ankle joint segment is formed of three points: an ankle joint center, a heel bone, and a toe.

(Measurement of Body Dimensions)

The construction of a wire-frame model requires body dimensions. The body dimensions measured at the time of gait measurement are described below. In this system, the body dimensions may be input with an input means, e.g., a keyboard connected to the processing device.

Intertrochanteric distance: A straight-line distance between right and left great trochanters Thigh length: A distance from a great trochanter to a lateral epicondyle of femur Shank length: A distance from a lateral condyle of tibia to an ankle joint lateral malleolus The pelvis segment is modeled such that the pelvis segment has an average shape consistently and the size varies in proportion to the intertrochanteric distance.

(Definition of Coordinate Systems)

Figure 14:
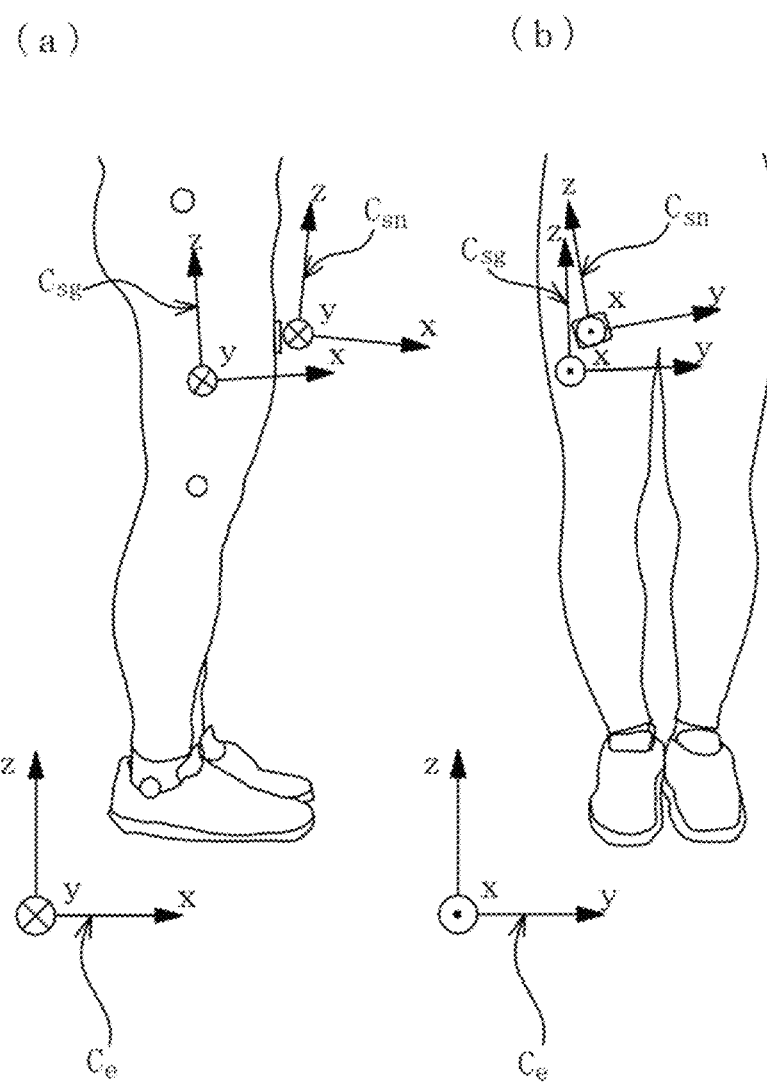
FIG. 14 is views describing a sensor coordinate system, a ground coordinate system, and a segment coordinate system according to the aforementioned embodiment, FIG. 14(*a*) is a side view, and FIG. 14(*b*) is a front view.

In the present embodiment, for calculation and expression of gait postures, three types of coordinate systems: a sensor coordinate system, a ground coordinate system, and a segment coordinate system are used. A right thigh is taken as an example, and three coordinate systems are illustrated in FIGS. 14($a$) and ($b$). In these drawings only, the sensor coordinate system is indicated by reference symbol $C_{sn}$, the ground coordinate system is indicated by reference symbol $C_e$, and the segment coordinate system is indicated by reference symbol $C_{sg}$.

The ground coordinate system is a stationary system for observation of motion, and is defined such that the z-axis is taken vertically upward and the x-axis is taken parallel to the initial sagittal-horizontal axis of a subject and anteriorly from the subject. The y-axis is taken to be perpendicular to both of them to form a right-handed system.

Figure 15:
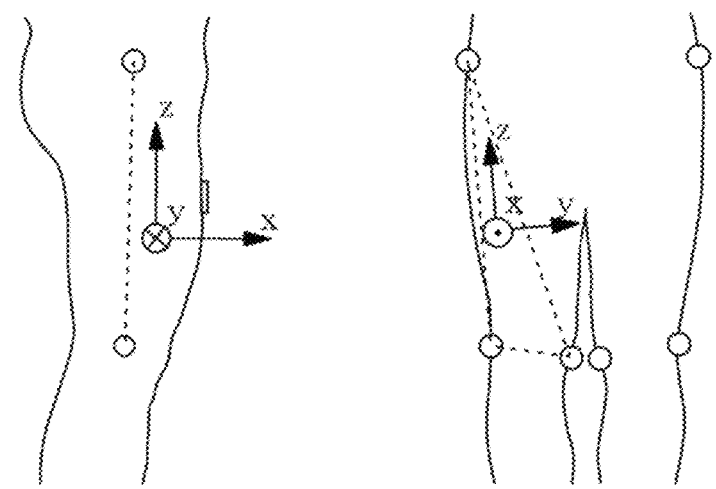
FIG. 15 illustrates a definition of a coordinate system of a right thigh segment according to the aforementioned embodiment, FIG. 15(*a*) is aside view, and FIG. 15(*b*) is a front view.

FIGS. 15($a$) and ($b$) illustrate the definition of the coordinate system of the thigh segment. The z-axis is taken parallel to a line connecting the great trochanter and the lateral knee joint space, and the sagittal-horizontal axis (front direction, walking direction) is taken as the x-axis.

Figure 16:
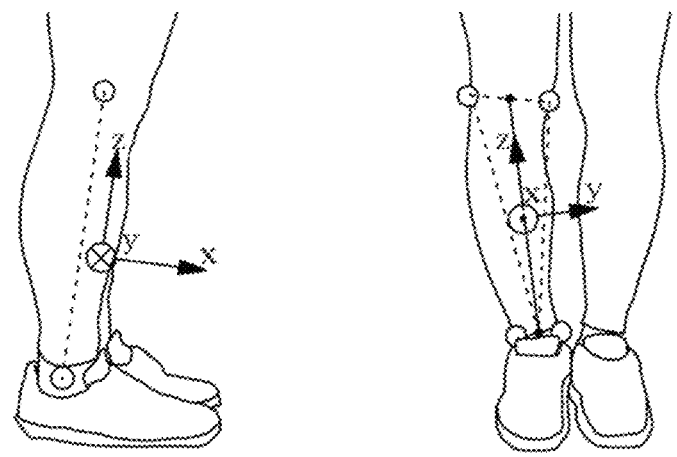
FIG. 16 illustrates a definition of a coordinate system of a right shank segment according to the aforementioned embodiment, FIG. 16(*a*) is aside view, and FIG. 16(*b*) is a front view.

FIGS. 16($a$) and ($b$) illustrate the definition of the coordinate system of the shank segment. The z-axis is taken parallel to a line connecting the knee joint center and the ankle joint center, and the sagittal-horizontal axis (front direction, walking direction) is taken as the x-axis. The knee joint center is a midpoint of the lateral knee joint space and the medial knee joint space, and the ankle joint center is a midpoint of the ankle joint lateral malleolus and the ankle joint medial malleolus.

The coordinate systems of the pelvis segment and the foot segments are defined to correspond to the ground coordinate system in a standing posture. When the standing posture is assumed, the toes are directed forward and the feet are aligned.

(Processing Device)

Figure 17:
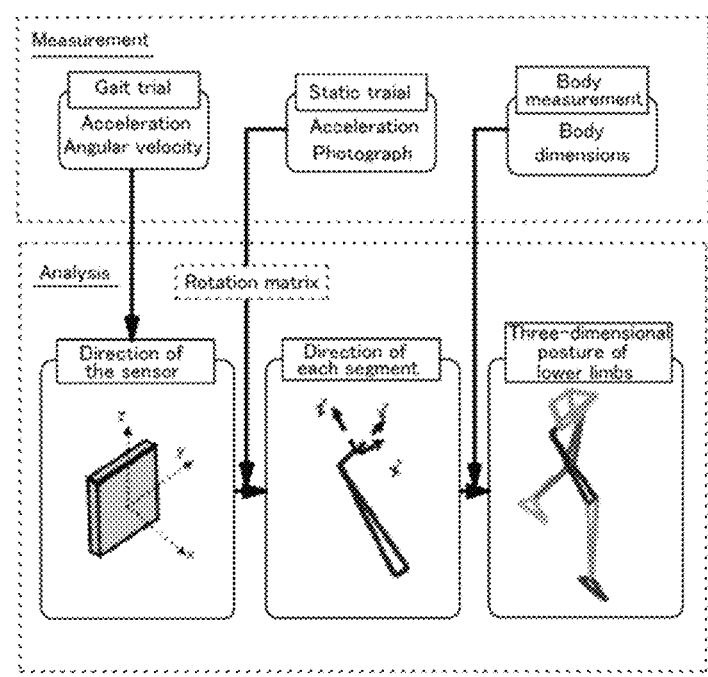
FIG. 17 is a diagram illustrating an analysis flow according to the gait analysis system and the gait analysis method according to the aforementioned embodiment.

Next, returning to FIG. 11, the processing device 5 of the gait analysis system is described. Additionally, a processing flow with the system is illustrated in FIG. 17. In the present embodiment, the processing device 5 uses a personal computer, but may be anything insofar as it can acquire acceleration data and angular velocity data from the sensor units 3 and perform predetermined computation processing to indicate a predetermined gait parameter on the monitor screen 7 or output or record a predetermined gait parameter on a different device.

As illustrated in FIG. 11, the processing device 5 includes a data acquisition portion 11 for acquiring acceleration data and angular velocity data from each sensor unit 3, a sensor posture estimation portion 13 for estimating the posture (orientation) of the sensor coordinate system on the basis of the acceleration data and the angular velocity data of each body part, the acceleration data and the angular velocity data being acquired by the data acquisition portion 11, a segment posture computation portion 15 for computing the posture of each segment by converting the posture estimated by the sensor posture estimation portion 13 into the posture (orientation) of the segment coordinate system, a lower limb posture computation portion 17 for creating each segment on the basis of the posture of each segment computed by the segment posture computation portion 15 and body dimensions input and coupling the created segments in a predetermined posture so as to compute a lower limb posture (three-dimensional wire-frame model) during gait, and a gait parameter computation portion 19 for calculating a gait parameter on the basis of the lower limb posture computed by the lower limb posture computation portion 17. The data acquisition portion 11, the sensor posture estimation portion 13, the segment posture computation portion 15, and the lower limb posture computation portion 17 described above constitute the model construction means of the present invention. In addition, the aforementioned gait parameter computation portion 19 constitutes the gait parameter calculation means of the present invention.

The sensor posture estimation portion 13 estimates the posture of the sensor during gait in the manner described below.

First, in the case of plane rotation, an angular displacement $\theta$ can be calculated by Equation (15).

[Equation 15]

$$\theta = \theta_0 + \int_0^t \omega dt \tag{15}$$

In Equation (15), the first term of the right-hand side indicates an initial posture (orientation), and the second term indicates an angular displacement from the initial posture. In the present embodiment, the initial posture is estimated through the use of the acceleration data obtained by the acceleration sensor. Furthermore, the angular displacement is estimated through the use of the angular velocity data obtained from the angular velocity sensor.

Figure 18:
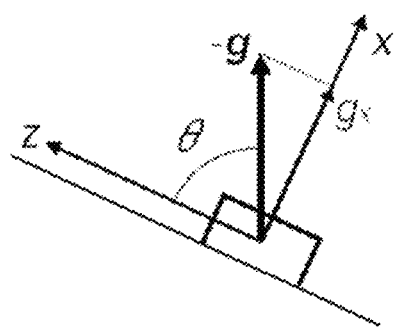
FIG. 18 is a view describing a principle of calculating an initial posture (initial orientation) of a sensor from acceleration data.

The principle of determining the initial posture of the sensor from the acceleration data is described with reference to FIG. 18. The acceleration sensor detects a motion acceleration a and a gravitational acceleration g simultaneously.

[Equation 16]

$$S = a - g \tag{16}$$

In particular, for example, at rest or in constant velocity motion, when motion acceleration does not apply with respect to the acceleration sensor, the acceleration sensor detects a gravitational acceleration component only.

[Equation 17]

$$S = -g \tag{17}$$

Accordingly, an angle formed by the vertical axis (gravity direction) and the detection axes of the acceleration sensor can be calculated from the proportion of the detection axes of the acceleration sensor and the vector sum.

[Equation 18]

$$\theta = \sin^{-1} \frac{g_x}{\|g\|} \tag{18}$$

In the case of three dimensions, in principle, even when rotation occurs about the gravity axis, it is impossible for the acceleration sensor to detect the acceleration, and only the initial posture is detected by the acceleration sensor. Therefore, the heading angle of the aforementioned Euler angles at a time when a subject assumes the initial posture may be defined to be 0°.

Next, the angular displacement is determined. Parameters input to unit quaternions indicating rotation include the axis of rotation and the amount of rotation about the axis. The quaternion is used to calculate the angular displacement because it is easy to match up with the angular velocity data obtained by the angular velocity sensor. An axis of rotation n and an amount of rotation $\theta$ are indicated by Equations (19) and (20) described below, respectively.

[Equation 19]

$$n = \frac{\omega}{\|\omega\|} \tag{19}$$

[Equation 20]

$$\theta = \|\omega\| \Delta t_s \tag{20}$$

Symbol $\omega$ indicates an angular velocity vector obtained from the detected acceleration of each axis of the angular sensor, and symbol $\Delta t_s$ indicates a sampling period. They are substituted into the aforementioned Equation (13), and the result is described below.

[Equation 21]

$$q = \left( \cos \frac{\|\omega\| \Delta t_s}{2} ; \frac{\omega}{\|\omega\|} \sin \frac{\|\omega\| \Delta t_s}{2} \right) \tag{21}$$

As a result of the input, a micro angular displacement per sampling period in which the angular velocity vector is the axis of rotation is obtained. Then, as this is integrated in time domain, the angular displacement from the initial posture is determined. In this way, the sensor posture estimation portion 13 estimates the posture of the sensor units 3.

Next, conversion of coordinate systems by the segment posture computation portion 15 is described. According to the present invention, the sensor units 3 are attached to body parts corresponding to the respective segments and measurement is performed to determine the posture of each body part (segment). However, it is difficult or impossible to attach the sensor units 3 such that the sensor coordinate system corresponds to the segment coordinate system. Therefore, for estimation of the motion of the segments, it is necessary that an experiment different from the gait experiment be performed to determine the relative postures between the sensor coordinate system and the segment coordinate system, and the posture of the sensor coordinate system be converted into the posture of the segment coordinate system.

Under conditions that factors including muscle contraction, clothing, and skin displacement are negligible, the sensor unit 3 and the segment exhibit a similar angular motion. Therefore, when the posture of the sensor unit 3 is determined, the posture of the segment can be determined as a result of rotation operation.

In reality, the following two processes are taken to determine the rotation matrix from the sensor coordinate system to the segment coordinate system.

Figure 19:
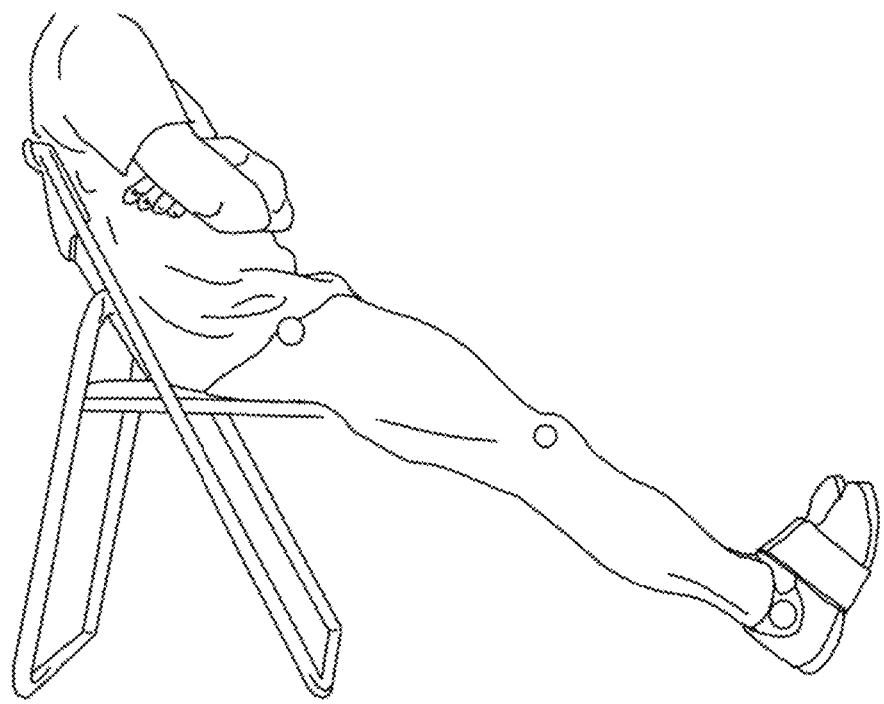
FIG. 19 is a view illustrating a seated posture for measurement of acceleration data at rest.

Rotation matrix from the sensor coordinate system to the ground coordinate system Rotation matrix from the ground coordinate system to the segment coordinate system The manner of determining the rotation matrix from the sensor coordinate system to the ground coordinate system is described. The acceleration data is measured when a subject is at rest in a standing posture or at rest in a seated posture. The standing posture is a state that a subject upstands on a horizontal ground where both toes are aligned as illustrated in FIG. 16. The seated posture is as illustrated in FIG. 19. The toes are also aligned in the seated posture. Thus, the gravitational accelerations in the case of the two postures: the standing posture and the seated posture can be obtained.

Figure 20:
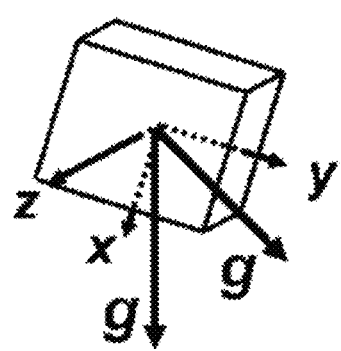
FIG. 20 is views illustrating two gravitational acceleration vectors for use in defining a sensor coordinate system.
Figure 20:
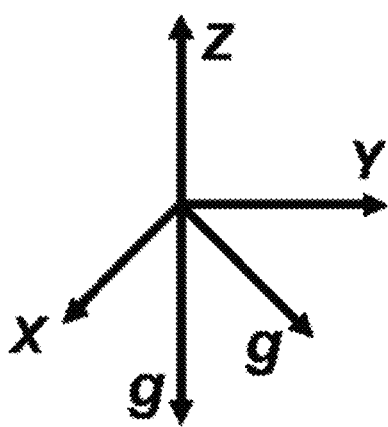

The manner of determining the rotation matrix from the sensor coordinate system to the ground coordinate system on the basis of the above is described in conjunction with FIG. 20. An arrow g positioned at the middle indicates the gravitational acceleration in the standing position, and an arrow g positioned on the right side indicates the gravitational acceleration in the seated position. The z-axis of the ground coordinate system is defined to be the direction opposite to that of the gravitational acceleration in the standing position. The y-axis is defined by a cross product of the gravitational acceleration in the standing position and the gravitational acceleration in the seated position. The x-axis is defined by a cross product of the y-axis and the z-axis.

Thus, the basic vector of the ground coordinate system with respect to the sensor coordinate system can be acquired.

The rotation from the ground coordinate system to the segment coordinate system provides the segment coordinate system with respect to the ground coordinate system from a front view photograph and a side view photograph in the standing posture as illustrated in FIG. 14, and the rotation matrix from the ground coordinate system to the segment coordinate system can be obtained.

Figure 21:
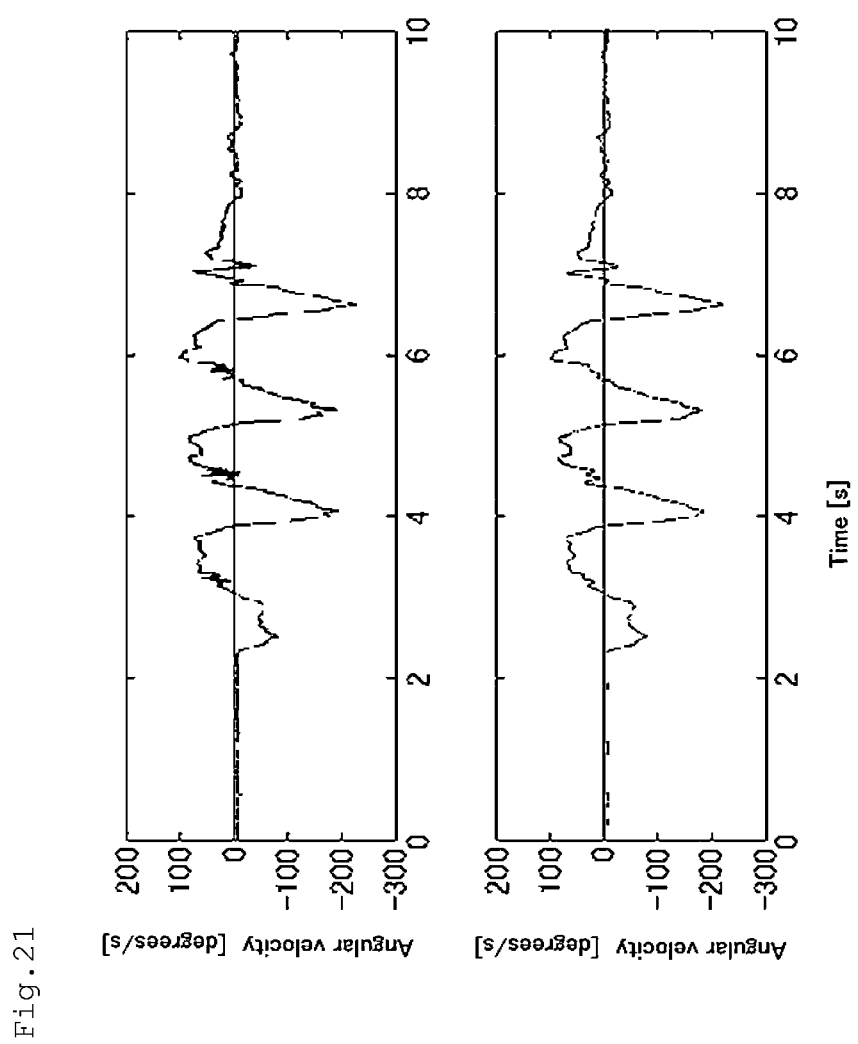
FIG. 21 is graphs illustrating states before and after low-pass filter processing with respect to data obtained from an angular velocity sensor, the upper illustrates a state before the processing, and the lower illustrates a state after the processing.

In addition, the system of the present embodiment includes a filtering means. The data obtained by the angular velocity sensor includes noise. Because the noise is high frequency, the noise can be removed by a low-pass filter. As the low-pass filter, for example, a Butterworth filter of an IIR digital filter may be used. In this case, the cutoff frequency can be 12 Hz. However, the use of this filter results in generation of a phase delay, but the filtering processing with the same property is performed twice in total: one before the data and the other after the data to eliminate the phase delay. FIG. 21 illustrates results of the low-pass filter processing by comparing the states before and after the filtering processing.

Figure 22:
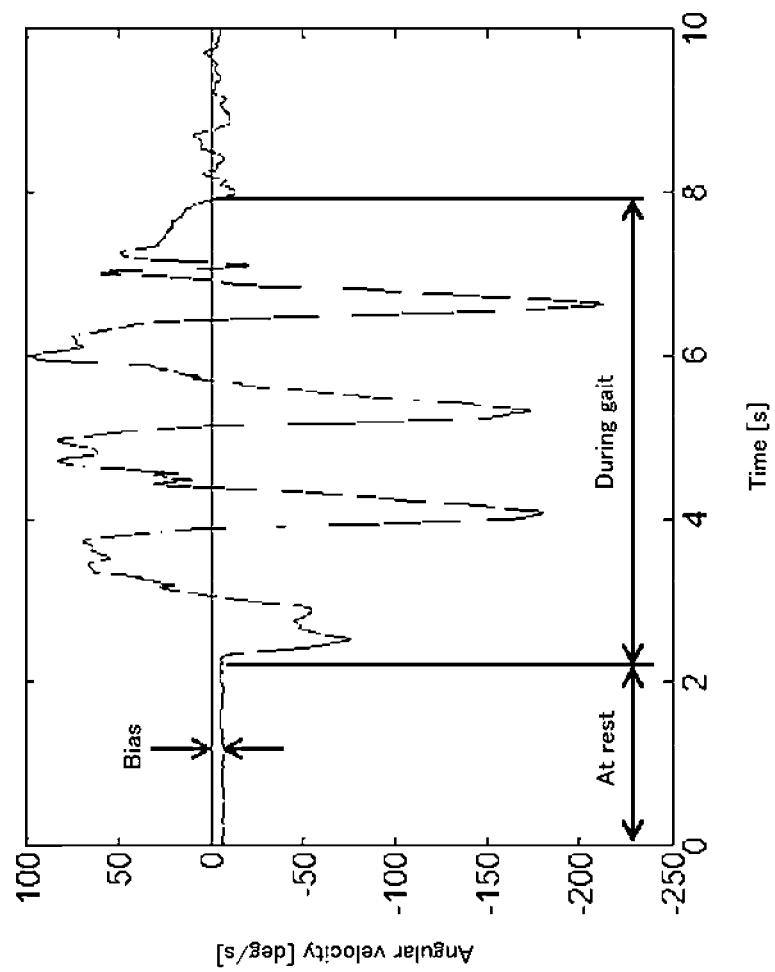
FIG. 22 is a graph illustrating a gyro bias included in data obtained from an angular velocity sensor.

In addition, the data obtained from the angular velocity sensor contain bias. This is described in conjunction with an angular velocity waveform at the time of gait measurement illustrated in FIG. 22. The horizontal axis indicates the time elapsed from beginning of measurement, and the vertical axis indicates the angular velocity about the y-axis of the sensor arranged on the right thigh. The angular velocity sensor records a non-zero value as a detected value even at rest. This is a bias of the angular velocity. As described above, in the present embodiment, the method of calculating the angular displacement includes an integration element. Therefore, biases are accumulated during numerical integration, which directly leads to errors. Thus, it is necessary that the amount of bias be estimated and be subtracted from the original data before integration calculation. There are various bias estimation methods. Here, for bias estimation, the mode of raw data is estimated to be bias.

The gait parameter computation portion 19 calculates various types of parameters required for gait assessment from the lower limb posture computed by the lower limb posture computation portion with a predetermined program and the timings of the heel contact and the toe off. The timings of the heel contact and the toe off can easily be determined by means of an optical system or a floor reaction force gauge. However, in the present embodiment, only the acceleration and angular velocity data are used for detection. Specifically, as described below, the timing of the heel contact is detected from the angular velocity data of the shank, and the timing of the toe off is detected from the relative positions of the right and left toes.

Figure 23:
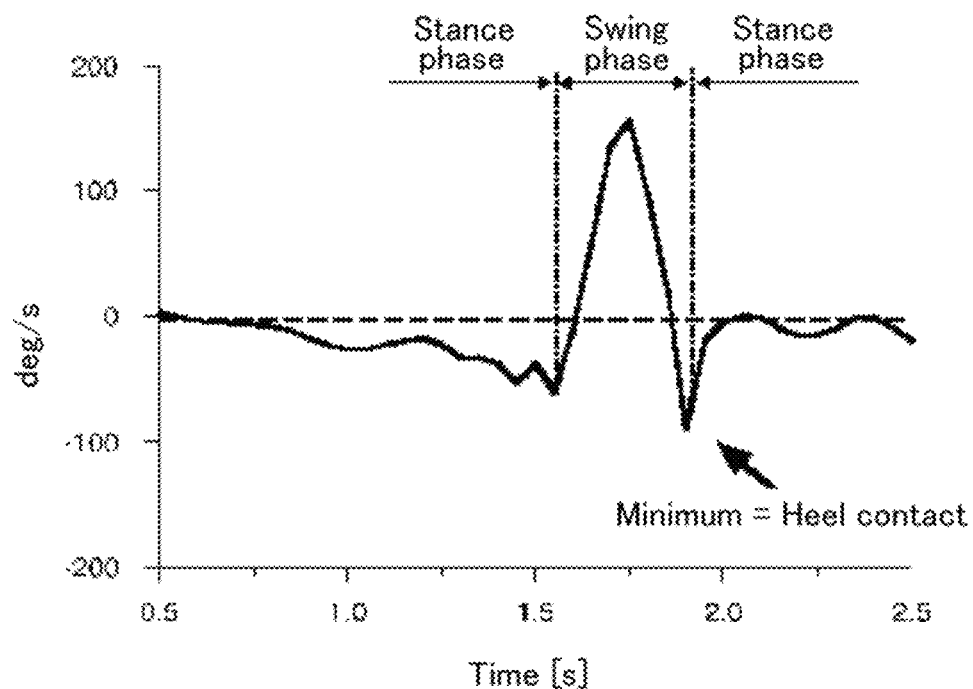
FIG. 23 is a graph illustrating a change of an angular velocity of a shank during gait.

As illustrated in FIG. 23, the angular velocity of the shank during gait is close to 0 degrees/second in the stance phase, and a relatively large angular velocity is generated in the swing phase because the shank is swung forward. Immediately before the heel contact, the shank swung forward is slightly pulled backward. Therefore, the peak value of the angular velocity appears in the direction opposite to that of the swing phase. This peak position is used for detection of the heel contact.

Figure 24:
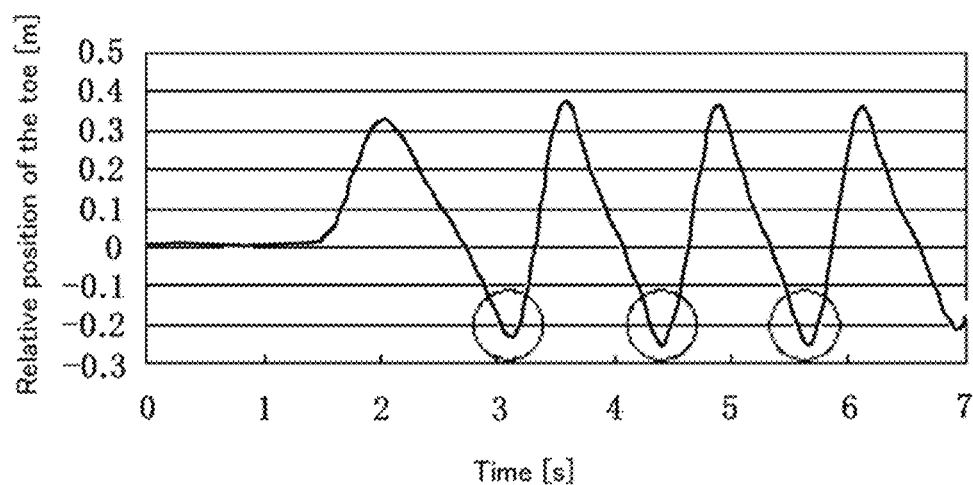
FIG. 24 is a graph illustrating a distance in a walking direction from an original point (midpoint of right and left hip joint centers) to a right toe.

FIG. 24 illustrates a distance in walking direction from the original point (midpoint of the right and left hip joint centers) to the right toe. This is a graph indicating a standing state at rest at the onset and the beginning of gait at the point near 1.5 seconds. When the gait begins, first, the right leg is swung forward, and the distance from the original point increases in a positive direction. The heel contact is made slightly after the positive peak position. Upon entry into the stance phase, the distance from the original point decreases, and subsequently the toe is shifted backward beyond the original point. Therefore, the distance from the original point increases in a negative direction. Then, the toe off is made, and the right leg again begins to swing forward, and the distance from the original point starts increasing in the positive direction. Until the toe off is made, the distance from the original point monotonically increases in the negative direction. Therefore, the negative peak position presumably corresponds to the timing of the toe off. In the present embodiment, the relative position of the toe is calculated from the lower limb posture obtained by the lower limb posture computation portion 17, and the timing at which the relative distance from the original point assumes the negative peak position is the timing of the toe off.

Next, gait parameters calculated by the gait parameter computation portion 19 from the lower limb posture computed by the lower limb posture computation portion 17 and the timings of the heel contact and the toe off are described below. These gait parameters are commonly used for diagnosis of a patient with knee osteoarthritis (knee OA), for example, in gait analysis through observation by a doctor or a physical therapist.

(a) Step Length: Step Length

The distance between the heel in heel contact and the heel of the opposite leg (b) Maximum Knee Flexion Angle: Max Knee Flexion in Swing The maximum value of a knee flexion angle observed in the swing phase (c) Maximum Knee Extension Angle: Max Knee Extension in Stance The maximum value of a knee extension angle observed in the stance phase (minimum value of knee flexion angle)

(d) Range of Motion of Knee Joint:ROM of Knee

The value obtained as the maximum knee extension angle is subtracted from the maximum knee flexion angle (e) Knee Flexion Angle (Immediately After Heel Contact): Max Knee Flexion in Stance The knee flexion angle at the time of an increase in the flexion angle observed immediately after the heel contact (f) Knee Flexion Angle (At the Time of Toe Off):Knee Flexion at Toe Off The knee flexion angle at the time of the toe off (g) Ankle Abduction Angle: Ankle Abduction in Stance The direction of the toe with respect to the walking direction in stance (h) Thigh and Shank Angle: FTA in Stance The maximum value of an angle formed by the z-axis of the thigh and the z-axis of the shank in the coronal plane in the stance phase (i) Lower Limb Functional Axis Inclination Angle (Abduction Direction): Maximum Inclination of Functional Axis of Lower Extremity in Stance The maximum value of an angle formed by a line connecting the hip joint center and the ankle joint center and the vertical axis in the sagittal plane in the stance phase (maximum abduction)

(j) Lower Limb Functional Axis Inclination Angle (Adduction Direction): Minimum Inclination of Functional Axis of Lower Extremity in Stance The minimum value of an angle formed by a line connecting the hip joint center and the ankle joint center and the vertical axis in the sagittal plane in the stance phase (maximum adduction)

(k) Gait Cycle:Gait Cycle

The time from the heel contact to the toe off and to the next heel contact (l) Stance Ratio: Stance Phase The quotient obtained by dividing the time (stance time) from the heel contact to the toe off by the gait cycle In addition to the aforementioned gait parameters, the gait parameter computation portion 19 calculates two further novel gait parameters. The novel assessment parameters can be obtained through the use of a Lissajous figure. The Lissajous figure is a "plane figure obtained on an orthogonal coordinate as two simple harmonic motions are combined". In the field of gait measurement, the Lissajous figure indicates a motion trajectory of a joint or a gravity center position in the sagittal plane, the horizontal plane, or the coronal plane. Regarding the Lissajous figure, currently, only the motion trajectory in the coronal plane is used, for example, in the field of gait research. This is because gait is a motion involving movement, and therefore in the case of an optical system or the like, a motion trajectory in the sagittal plane or the horizontal plane does not draw a closed curve, but forms a single wave-like trajectory, which renders it difficult to handle. Meanwhile, with the gait analysis system including the property in which a lower limb posture is calculated as the midpoint of the right and left hip joint centers is used as the original point, and the Lissajous figure of each joint can be obtained as a closed curve in all the planes : the sagittal plane, the horizontal plane, and the coronal plane. In the present embodiment, the Lissajous figure is drawn by the gait parameter calculation portion 19.

Figure 25:
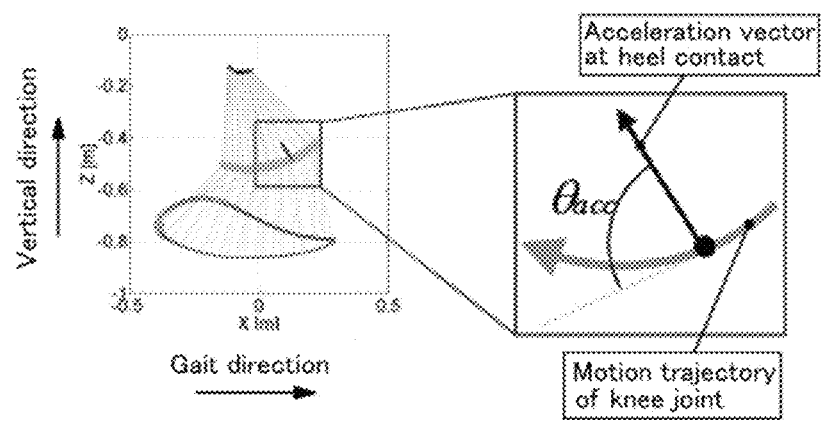
FIG. 25 is a view illustrating motion trajectories of joints in a sagittal plane and an acceleration vector at the time of heel contact.

The first novel gait parameter is a knee acceleration vector direction. FIG. 25 illustrates motion trajectories of joints (great trochanter, knee joint, ankle joint) in the sagittal plane. The original point is the midpoint of the right and left hip joint centers, and the rightward direction in the plane of paper is the walking direction. The arrow line supplementary indicated on the motion trajectory of the knee joint indicates the acceleration vector at the time of the heel contact. The parameter calculation portion 19 calculates an angle $\theta_{acc}$ of the acceleration vector with regard to the knee joint trajectory as an assessment parameter.

Figure 26:
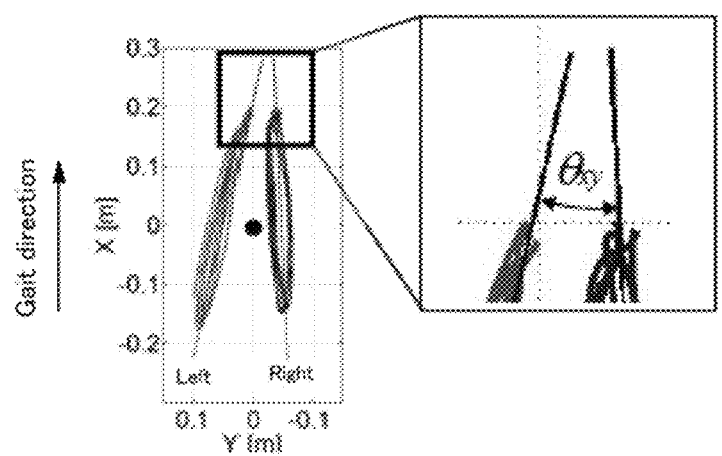
FIG. 26 is a view illustrating motion trajectories of knee joints in a horizontal plane and a trajectory angle of knee joints in a horizontal plane.

The other novel gait parameter is a trajectory angle in a knee joint horizontal plane. FIG. 26 illustrates motion trajectories of knee joints in the horizontal plane. The original point is the midpoint of the right and left hip joint centers, and the upward direction in the plane of paper is the walking direction. The left closed curve is the motion trajectory of the left knee joint, and the right closed curve is the motion trajectory of the right knee joint. In the drawing, straight lines extending substantially up and down in the motion trajectories are obtained as the motion trajectories are approximated to a straight line. The parameter calculation portion calculates an angle $\theta_{xy}$ formed by the two straight lines as an assessment parameter.

Figure 27:
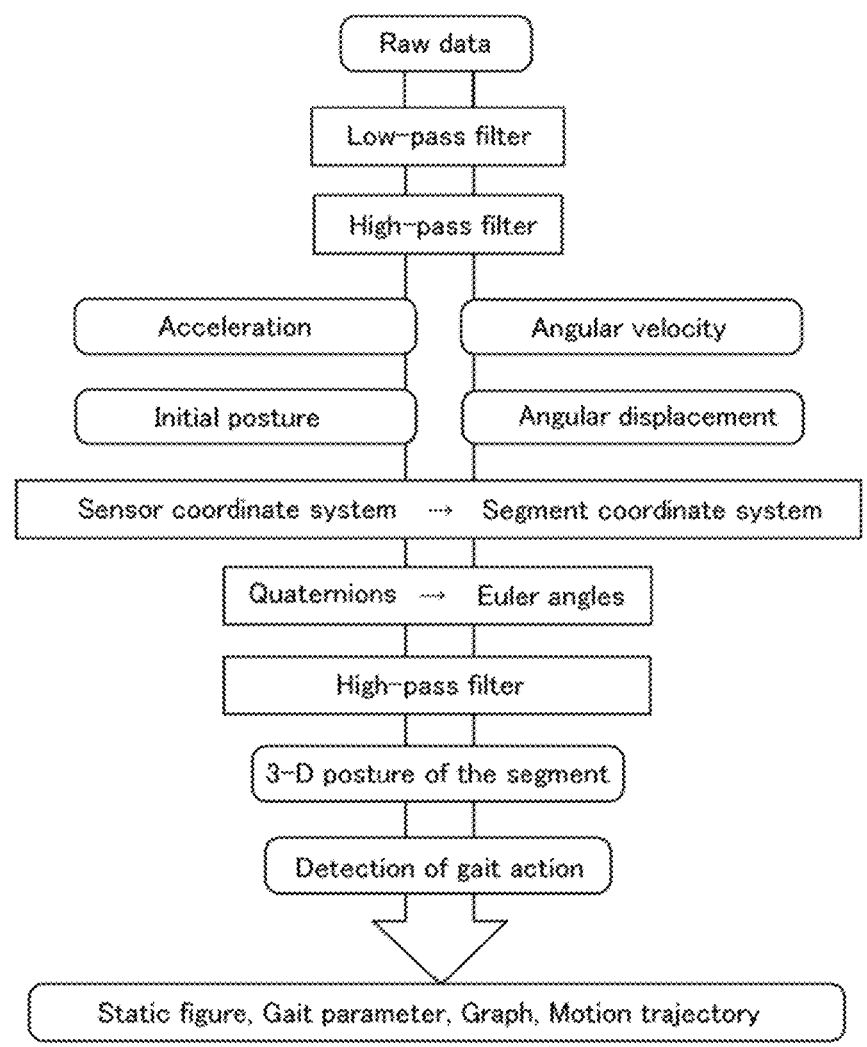
FIG. 27 is a flowchart indicating a data flow of a gait analysis system according to the aforementioned embodiment.

FIG. 27 illustrates a method of data processing using the gait analysis system configured in the aforementioned manner. First, raw data obtained in a gait experiment passes through a low-pass filter and a high-pass filter. Next, the initial posture and the angular displacement of each segment are calculated through the calculation of the posture of the sensor unit 3 during gait and the conversion of coordinate systems from the sensor coordinate system to the segment coordinate system. The calculation uses quaternions, and therefore in this stage the initial posture and the angular displacement are expressed in terms of quaternions. As described above, the mode is used to estimate an angular velocity bias. Therefore, the bias estimation precision depends on resolution. Accordingly, the angular displacement, a result of its integration, includes integration drift of estimation errors. Because drift cannot be removed by a high-pass filter while the quaternions are left as they are. Therefore, first, the quaternions are converted to Euler angles and the integration drift is removed with respect to the resultant three Euler angles. Thus, when the posture of each segment is determined, next, each segment is created on the basis of body dimensions and the segments are coupled together to construct the lower limb posture during gait. The aforementioned various types of gait parameters can be calculated on the basis of the lower limb posture.

Next, an experiment conducted to confirm the effect of the gait analysis method and the gait analysis system according to the present invention is described. The present invention is not limited to the scope of the experiment described below.

(Experimental Procedure)

Figure 28:
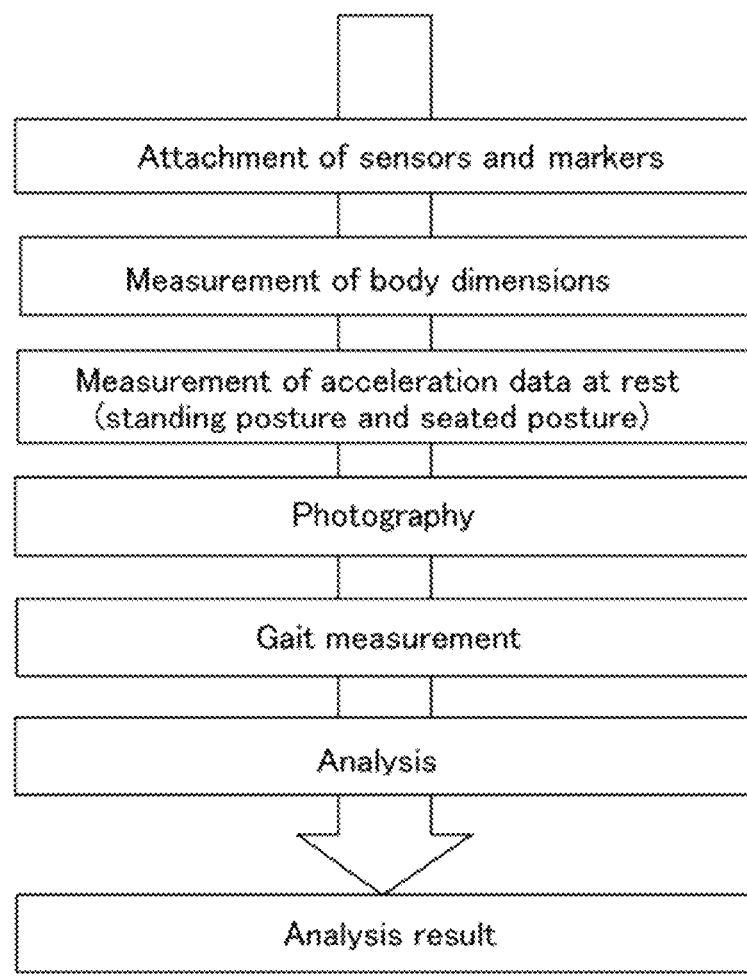
FIG. 28 is a flowchart indicating a procedure of an experiment according to the gait analysis system and the gait analysis method according to the aforementioned embodiment.

First, a procedure of an experiment conducted is briefly illustrated in FIG. 28. First, the seven sensor units 3 were attached to parts, and ten markers 4 (see FIG. 12) were attached to the right and left great trochanters, the medial and lateral knee joint spaces, ankle joint medial malleolus and lateral malleolus, respectively. Next, body dimensions (intertrochanteric distance, thigh length, shank length) were measured. Next, acceleration data for use in conversion of coordinate systems from the sensor coordinate system to the segment coordinate system was measured. In this case, the standing posture of a subject was photographed from the front side, the left side, and the right side. Then, gait was measured (measurement of acceleration and angular velocity). Conditions of gait will be described later. The various types of gait parameters, the graphs, and the motion trajectories described above were obtained through analysis using a program on the basis of the acceleration and angular velocity data obtained by the measurement up to this point, and the photographs.

(Reproducibility Study Experiment)

On the assumption of operation at clinical site, measurement using the gait analysis method and the gait analysis system according to the present embodiment has to be reproducible. As used herein, the reproducibility of measurement indicates the following two meanings: reproducibility at a time when different measurers measure the same subject, and reproducibility at a time when the same subject is measured on different days (day-to-day reproducibility). Specifically, it is required that measurement can be done by any measurer and follow-up after treatment of a subject can be understood correctly.

The subjects included eight healthy males without lower limb history. The averages and the standard deviations of age, weight, height, BMI, and body dimensions are indicated in Table 1 together with values of a knee OA patient group to be described later.

TABLE 1

| | Healthy group Average (Standard deviation) | Knee OA group Average (Standard deviation) |
|---|---|---|
| Age [years] | 22.9 (0.8) | 68.7 (4.1) |
| Weight [kg] | 69.1 (5.4) | 54.2 (5.9) |
| Height [m] | 1.74 (0.05) | 1.52 (0.05) |
| BMI [kg/m$^2$] | 23.0 (1.6) | 23.5 (2.5) |
| Thigh length [cm] | 38.0 (2.3) | 32.4 (2.7) |
| Shank length [cm] | 40.8 (1.6) | 35.6 (1.7) |
| Distance between the greater trochanters [cm] | 35.6 (1.5) | 34.5 (1.5) |

Figure 29:
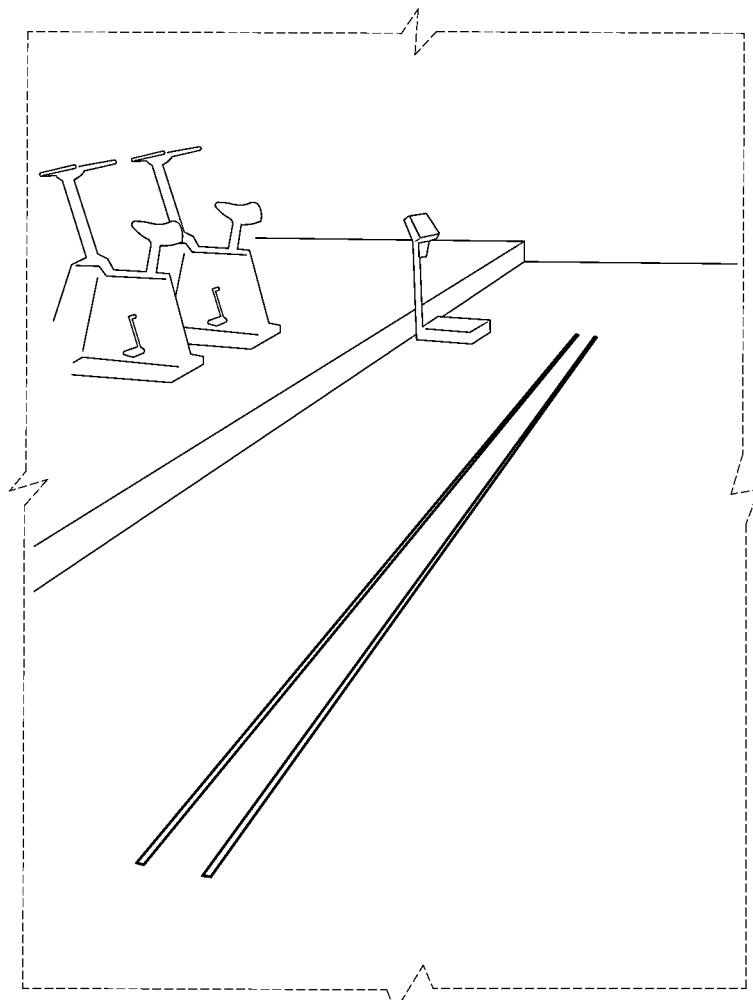
FIG. 29 is photographs illustrating a walkway employed in the aforementioned experiment, FIG. 29(*a*) is a straight flat way of 7 m, and FIG. 29(*b*) is a treadmill.
Figure 29:
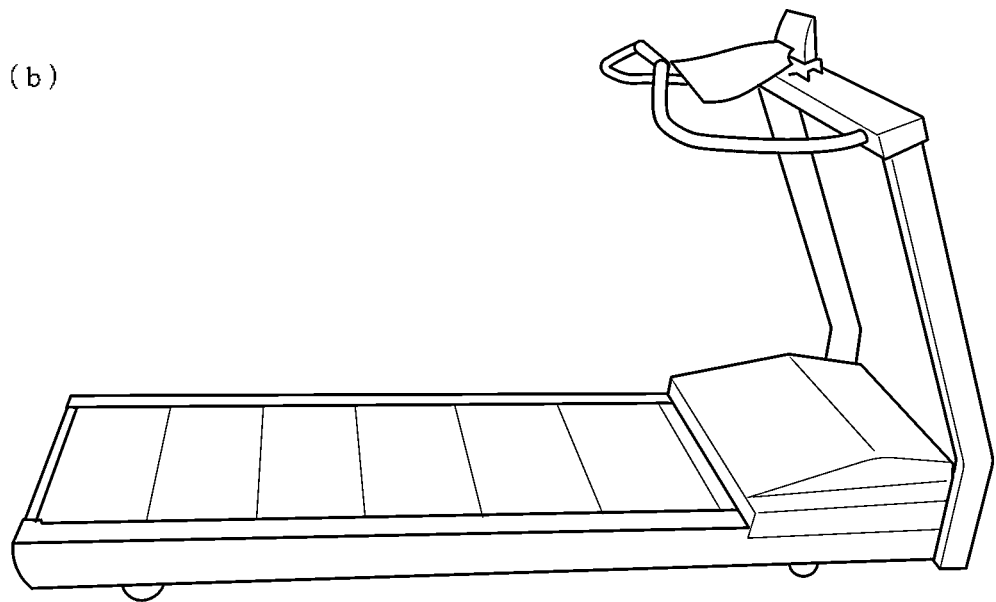

Next, experimental conditions are described. Two types of gait experiments were conducted: on a straight flat way of 7 m and on a treadmill (Gait Trainer 2™ manufactured by BIODEX Inc.) illustrated in FIGS. 29(a) and (b), respectively.

The gait measurement on the straight flat way started from a standing resting state illustrated in FIG. 16. The subjects walked at given velocity and then again assumed a standing resting state.

The gait measurement on the treadmill started from a standing resting state on the belt at rest. The belt velocity was gradually increased to 3 km per hour, and after gait at a steady velocity, the belt was again stopped, and the subjects assumed a standing state. The duration from the start to the end was consistently about 20 seconds.

In order to study a difference between measurement results depending on the measurer, two measurers (indicated as Measurers $A_{1st}$ and $B_{1st}$) separately conducted the same experiment on the same day to perform measurement on each subject. In addition, in order to study a difference between measurement results depending on the measurement date, Measurer A performed the same trial on each subject about one week after the first measurement to again conduct measurement (indicated as Measurer $A_{2nd}$). The measurement was performed once with respect to each gait condition and measurement condition, and a total of six measurement results were obtained per person.

For calculation of the gait parameters, which were measurement results, data excluding the beginning and the end of the gait was used. In the case of level ground gait, data including a total of four steps: two right steps and two left steps was used, and in the case of treadmill gait, data including a total of ten steps: five right steps and five left steps was used.

(Gait Measurement Experiment on Knee OA Patients)

The subjects of a gait measurement experiment on knee OA patients include ten medial knee OA patients. The averages and the standard deviations of age, weight, height, BMI, and body dimensions are indicated in Table 1 described above, and information regarding symptoms is indicated in Table 2. In Table 2, Patient B is male and the other patients are female. In the Table, symbol "-" indicates that no diagnosis has been conducted, not indicating absence of symptoms.

TABLE 2

| Patient | Severity of condition | Pain during gait | Kellgren-Lawrence grade Right knee | Kellgren-Lawrence grade Left knee |
|---|---|---|---|---|
| A | R < L | Mild | Moderate | Severe |
| B | R < L | None | Moderate | Moderate |
| C | R = L | None | Suspicious | Moderate |
| D | R < L | None | — | Moderate |
| E | R = L | Mild | — | Moderate |
| F | R < L | Mild | — | Mild |
| G | R > L | None | Moderate | — |
| H | R = L | None | — | Moderate |
| I | R > L | Mild | — | Moderate |
| J | R > L | Mild | Moderate | — |

The gait measurement experiment on the knee OA patients was conducted in the same manner as the reproducibility study experiment. However, because gait on a treadmill requires getting used to and from a safety perspective, the walkway included a straight flat way of 7 m only. The measurement was conducted once by Measurer A on each subject. For calculation of the gait parameters, which were measurement results, data including a total of six steps: three right steps and three left steps excluding the beginning and the end of the gait was used.

(Results of Reproducibility Study)

Results of the reproducibility study experiment are indicated in Tables 3 to 6. The Tables respectively indicate results of a comparison between measurement dates in the case of level ground gait, results of a comparison between measurers in the case of level ground gait, results of a comparison between measurement dates in the case of treadmill gait, and results of a comparison between measurers in the case of treadmill gait. The parameters of the eight healthy persons under each condition, and the average values and the standard deviations of absolute differences between the conditions are described in the Tables. In addition, a paired t-test was conducted as a significance test between the results of the conditions. It was a two-tailed test with a significance level of 5%. The p values at this time are described in the Tables. The gait of the healthy persons did not exhibit a difference in parameter between the right and left legs. Therefore, the average values and the standard deviations in the Tables are calculated on the basis of the average values of the right and the left of each subject.

TABLE 3

| | Measurer | | Absolute | |
| --- | --- | --- | --- | --- |
| | $A_{1st}$ Average (Standard deviation) | $A_{2nd}$ Average (Standard deviation) | difference Average (Standard deviation) | p-value |
| Step length [cm] | 57.8 (5.0) | 58.5 (4.6) | 3.8 (2.0) | 0.580 |
| Max knee flexion angle in swing [°] | 87.8 (5.0) | 85.6 (6.4) | 5.6 (4.6) | 0.240 |
| Max knee extension angle in stance [°] | 14.7 (6.4) | 14.2 (6.9) | 3.5 (2.3) | 0.675 |
| Range of motion of knee joint [°] | 72.6 (8.1) | 70.8 (6.6) | 4.1 (3.3) | 0.165 |
| Knee flexion angle (immediately after heel contact) [°] | 29.3 (9.8) | 28.6 (8.2) | 3.8 (3.4) | 0.598 |
| Knee flexion angle (at the time of toe off) [°] | 61.7 (5.6) | 61.9 (6.5) | 5.3 (3.7) | 0.911 |
| Ankle abduction angle [°] | 7.4 (7.9) | 6.6 (9.5) | 2.8 (2.5) | 0.391 |
| Thigh and shank angle [°] | 184.6 (5.6) | 185.3 (9.4) | 3.7 (2.8) | 0.590 |
| Lower limb functional axis inclination angle (abduction direction) [°] | −1.7 (2.4) | −2.4 (2.9) | 1.9 (1.2) | 0.197 |
| Lower limb functional axis inclination angle (adduction direction) [°] | −7.9 (1.7) | −7.8 (1.2) | 1.3 (0.9) | 0.807 |
| Gait cycle [s] | 1.19 (0.07) | 1.19 (0.08) | 0.05 (0.02) | 0.816 |
| Stance ratio [%] | 55.5 (2.0) | 55.3 (1.9) | 0.9 (0.7) | 0.521 |
| Angle between right and left knee joint tranjectory [°] | 4.7 (7.6) | 6.4 (7.4) | 4.2 (3.6) | 0.416 |
| Direction of knee acceleration vector (at heel contact) [°] | 62.3 (11.3) | 63.2 (7.4) | 5.3 (2.0) | 0.681 |

TABLE 4

| | Measurer | | Absolute | |
| --- | --- | --- | --- | --- |
| | $A_{1st}$ Average (Standard deviation) | $B_{1st}$ Average (Standard deviation) | difference Average (Standard deviation) | p-value |
| Step length [cm] | 57.8 (5.0) | 60.0 (4.8) | 3.2 (2.4) | 0.071 |
| Max knee flexion angle in swing [°] | 87.8 (5.0) | 82.7 (4.7) | 6.2 (4.0) | 0.002 |
| Max knee extension angle in stance [°] | 14.7 (6.4) | 12.1 (4.7) | 3.7 (3.1) | 0.027 |
| Range of motion of knee joint [°] | 72.6 (8.1) | 70.1 (5.0) | 5.1 (3.1) | 0.098 |
| Knee flexion angle (immediately after heel contact) [°] | 29.3 (9.8) | 25.8 (6.4) | 5.6 (4.8) | 0.056 |
| Knee flexion angle (at the time of toe off) [°] | 61.7 (5.6) | 58.5 (5.2) | 4.3 (2.8) | 0.008 |
| Ankle abduction angle [°] | 7.4 (7.9) | 6.8 (6.3) | 3.4 (2.7) | 0.578 |
| Thigh and shank angle [°] | 184.6 (5.6) | 182.7 (6.2) | 2.5 (1.9) | 0.077 |
| Lower limb functional axis inclination angle (abduction direction) [°] | −1.7 (2.4) | −2.1 (2.3) | 1.0 (1.1) | 0.348 |
| Lower limb functional axis inclination angle (adduction direction) [°] | −7.9 (1.7) | −7.6 (1.4) | 1.2 (1.2) | 0.440 |
| Gait cycle [s] | 1.19 (0.07) | 1.21 (0.09) | 0.05 (0.04) | 0.167 |
| Stance ratio [%] | 55.5 (2.0) | 56.1 (2.1) | 1.1 (1.1) | 0.107 |
| Angle between right and left knee joint tranjectory [°] | 4.7 (7.6) | 1.8 (2.1) | 5.8 (4.3) | 0.288 |
| Direction of knee acceleration vector (at heel contact) [°] | 62.3 (11.3) | 62.5 (10.5) | 5.3 (3.4) | 0.937 |

TABLE 5

| | Measurer | | Absolute | |
| --- | --- | --- | --- | --- |
| | $A_{1st}$ Average (Standard deviation) | $A_{2nd}$ Average (Standard deviation) | difference Average (Standard deviation) | p-value |
| Step length [cm] | 44.6 (5.9) | 44.7 (5.4) | 2.8 (1.8) | 0.970 |
| Max knee flexion angle in swing [°] | 80.6 (10.4) | 81.4 (7.1) | 7.9 (8.0) | 0.767 |
| Max knee extension angle in stance [°] | 11.6 (6.8) | 12.7 (4.9) | 3.0 (3.2) | 0.360 |
| Range of motion of knee joint [°] | 68.3 (9.5) | 68.1 (8.5) | 6.6 (6.8) | 0.943 |
| Knee flexion angle (immediately after heel contact) [°] | 26.6 (8.5) | 25.5 (7.1) | 5.8 (4.7) | 0.596 |
| Knee flexion angle (at the time of toe off) [°] | 57.1 (9.0) | 58.7 (10.6) | 7.9 (7.5) | 0.563 |
| Ankle abduction angle [°] | 7.7 (9.5) | 6.7 (10.1) | 2.2 (1.6) | 0.159 |
| Thigh and shank angle [°] | 185.5 (7.5) | 184.6 (6.7) | 4.5 (3.6) | 0.570 |
| Lower limb functional axis inclination angle (abduction direction) [°] | −3.9 (1.8) | −3.0 (2.7) | 1.3 (1.9) | 0.127 |
| Lower limb functional axis inclination angle (adduction direction) [°] | −8.2 (1.4) | −7.8 (1.1) | 1.2 (1.0) | 0.329 |
| Gait cycle [s] | 1.28 (0.11) | 1.33 (0.09) | 0.07 (0.04) | 0.016 |
| Stance ratio [%] | 56.4 (3.5) | 56.5 (2.3) | 1.9 (1.8) | 0.967 |
| Angle between right and left knee joint tranjectory [°] | 1.4 (4.7) | 3.0 (5.3) | 6.0 (3.3) | 0.543 |
| Direction of knee acceleration vector (at heel contact) [°] | 64.7 (14.8) | 79.3 (16.3) | 17.8 (11.4) | 0.040 |

TABLE 6

| | Measurer | | Absolute | |
| --- | --- | --- | --- | --- |
| | $A_{1st}$ Average (Standard deviation) | $B_{1st}$ Average (Standard deviation) | difference Average (Standard deviation) | p-value |
| Step length [cm] | 44.6 (5.9) | 45.8 (4.8) | 3.2 (2.9) | 0.316 |
| Max knee flexion angle in swing [°] | 80.6 (10.4) | 81.1 (7.7) | 5.8 (5.4) | 0.789 |
| Max knee extension angle in stance [°] | 11.6 (6.8) | 10.9 (5.6) | 4.3 (4.7) | 0.636 |
| Range of motion of knee joint [°] | 68.3 (9.5) | 69.1 (10.0) | 5.2 (3.5) | 0.594 |
| Knee flexion angle (immediately after heel contact) [°] | 26.6 (8.5) | 24.5 (8.0) | 5.1 (4.5) | 0.231 |
| Knee flexion angle (at the time of toe off) [°] | 57.1 (9.0) | 56.7 (8.8) | 7.3 (5.7) | 0.895 |
| Ankle abduction angle [°] | 7.7 (9.5) | 7.8 (8.9) | 2.9 (2.2) | 0.945 |
| Thigh and shank angle [°] | 185.5 (7.5) | 185.0 (8.4) | 4.7 (4.3) | 0.769 |
| Lower limb functional axis inclination angle (abduction direction) [°] | −3.9 (1.8) | −3.3 (2.1) | 1.6 (1.3) | 0.225 |
| Lower limb functional axis inclination angle (adduction direction) [°] | −8.2 (1.4) | −7.9 (1.5) | 1.1 (0.7) | 0.412 |
| Gait cycle [s] | 1.28 (0.11) | 1.31 (0.13) | 0.05 (0.05) | 0.079 |
| Stance ratio [%] | 56.4 (3.5) | 56.1 (2.6) | 1.9 (1.4) | 0.566 |
| Angle between right and left knee joint tranjectory [°] | 1.4 (4.7) | 3.9 (4.7) | 3.7 (2.9) | 0.147 |
| Direction of knee acceleration vector (at heel contact) [°] | 64.7 (14.8) | 71.1 (13.4) | 12.2 (6.6) | 0.215 |

(Results of Gait Measurements on Knee OA Patients)

Figure 30:
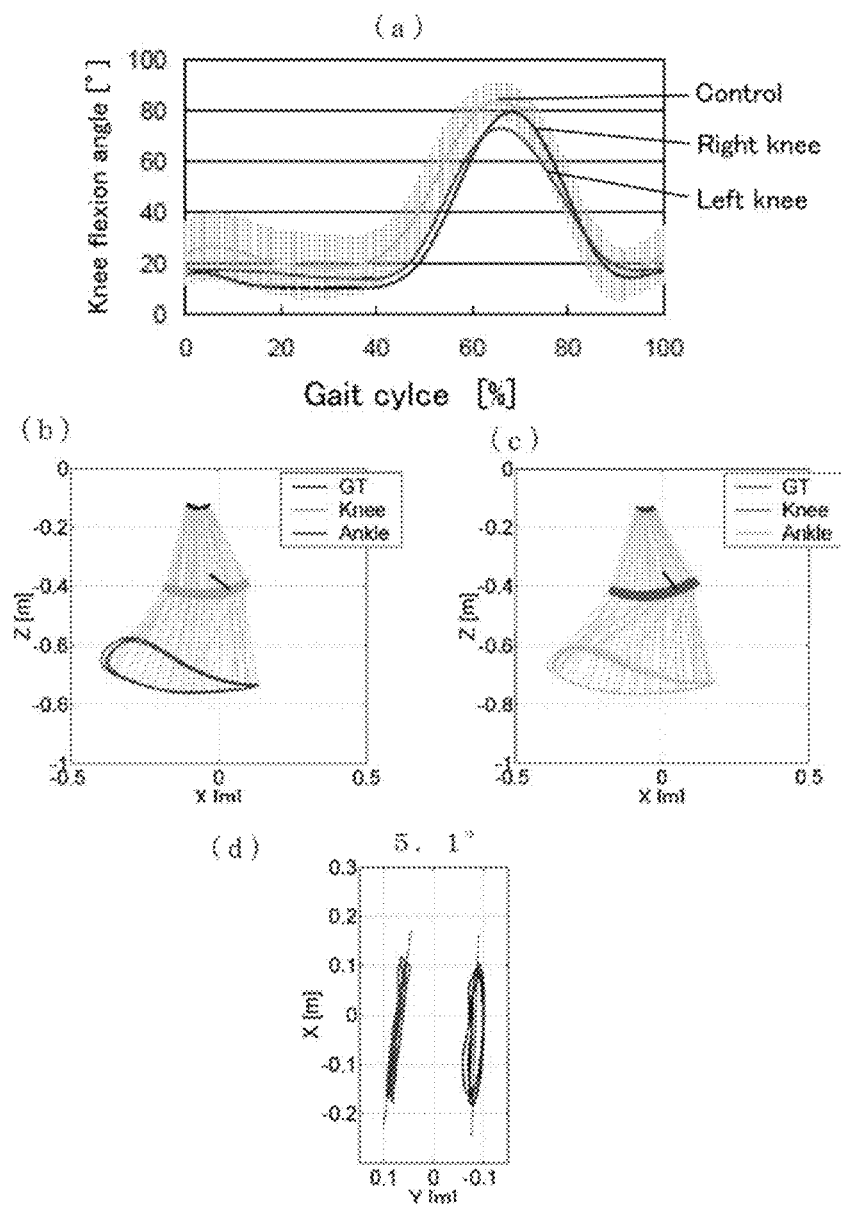
FIG. 30 is graphs illustrating results of measurement of gait of Patient A, FIG. 30(*a*) is a graph illustrating a knee flexion angle, FIG. 30(*b*) is a graph illustrating motion trajectories of joints (great trochanter, knee joint, ankle joint) of a right leg in a sagittal plane, FIG. 30(*c*) is a graph illustrating motion trajectories of joints (great trochanter, knee joint, ankle joint) of a left leg in a sagittal plane, and FIG. 30(*d*) is a graph illustrating motion trajectories of knee joints in a horizontal plane.
Figure 31:
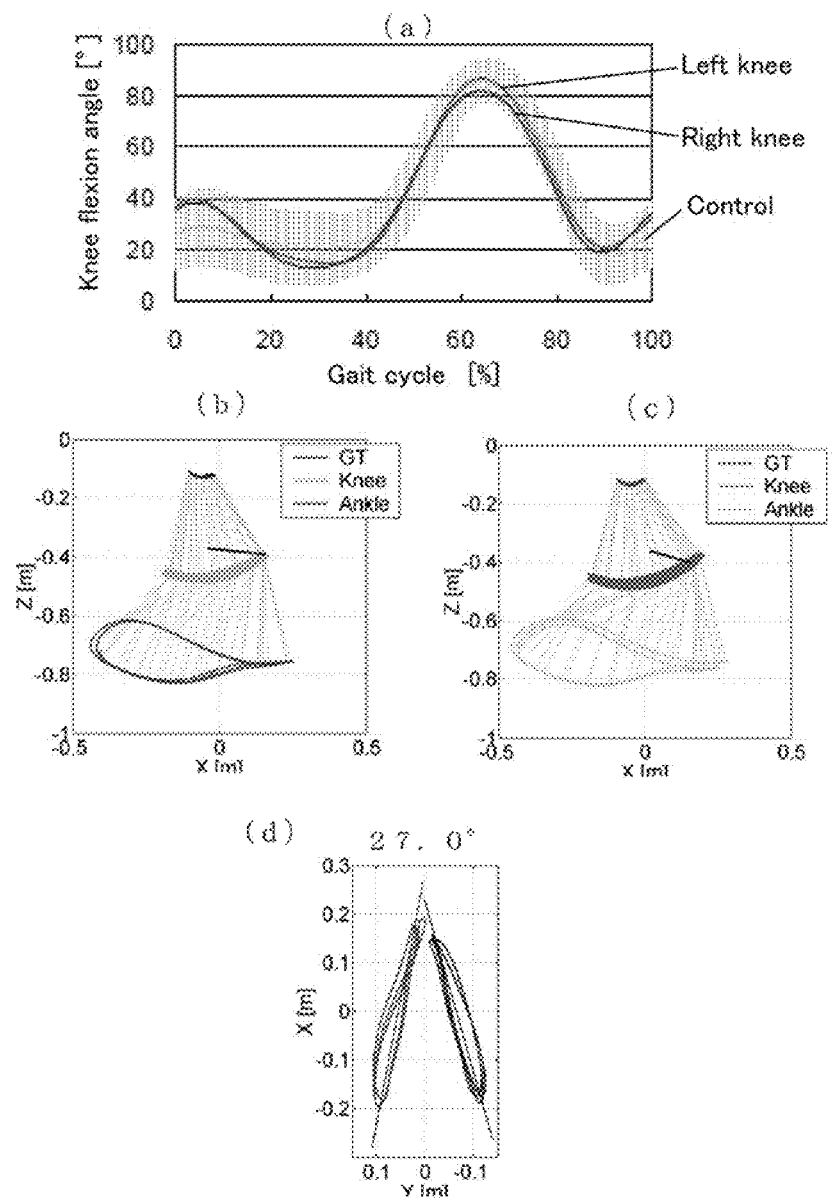
FIG. 31 is graphs illustrating results of measurement of a gait of Patient B, FIG. 31(*a*) is a graph illustrating a knee flexion angle, FIG. 31(*b*) is a graph illustrating motion trajectories of joints (great trochanter, knee joint, ankle joint)
Figure 32:
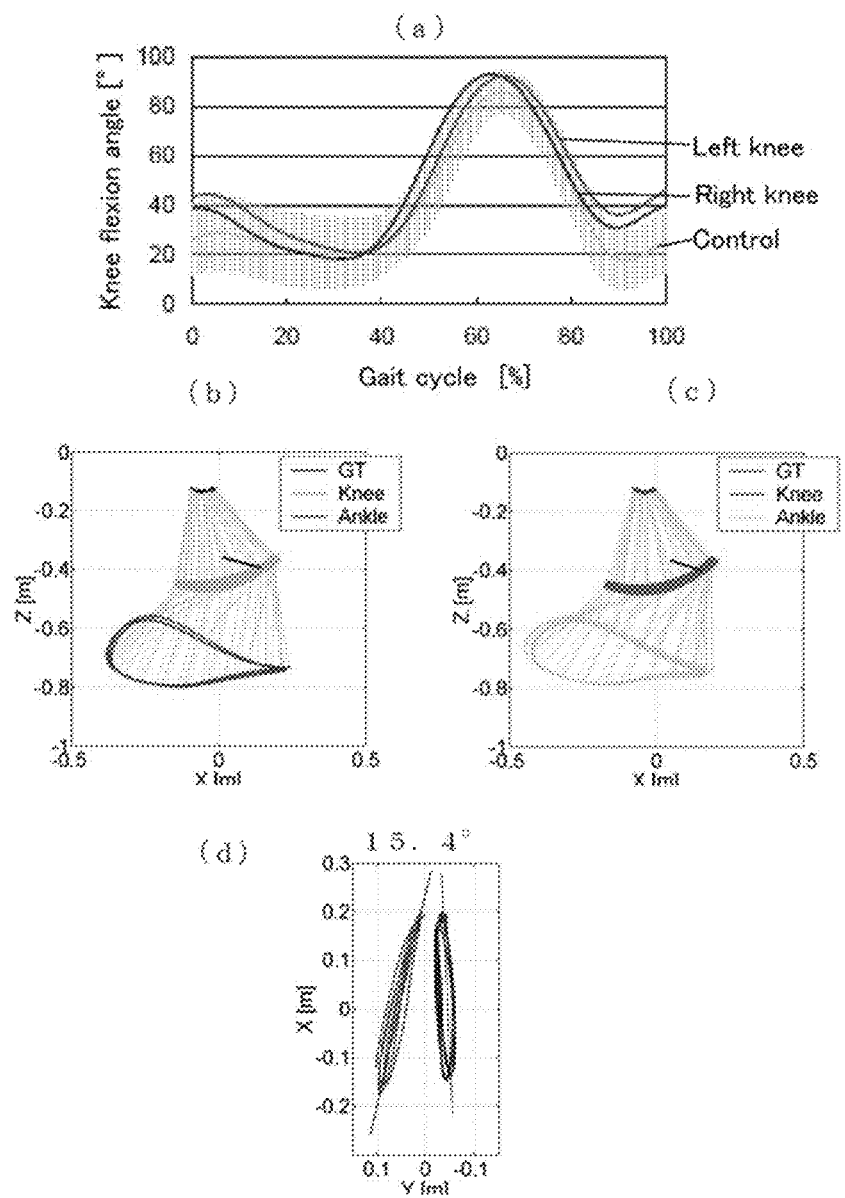
FIG. 32 is graphs illustrating results of measurement of gait of Patient C.
Figure 33:
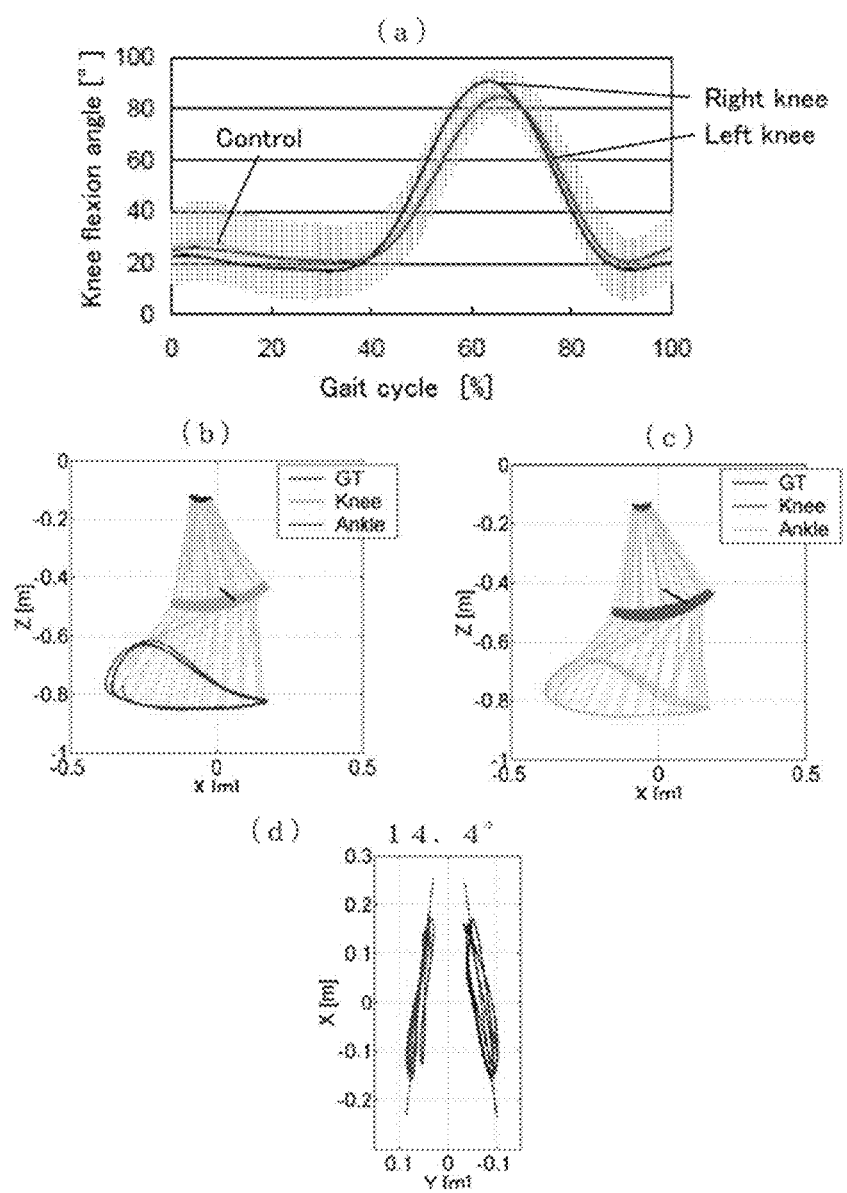
FIG. 33 is graphs illustrating results of measurement of gait of Patient D.
Figure 34:
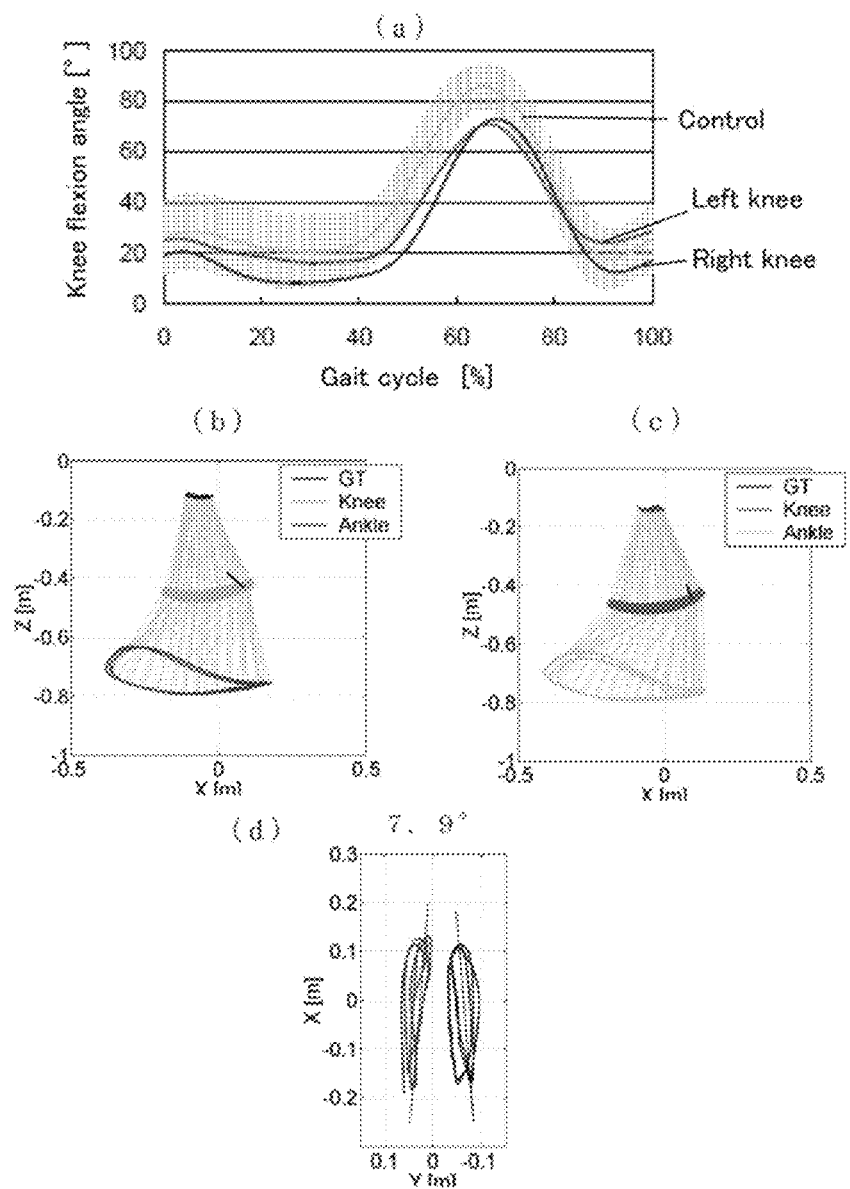
FIG. 34 is graphs illustrating results of measurement of gait of Patient E.
Figure 35:
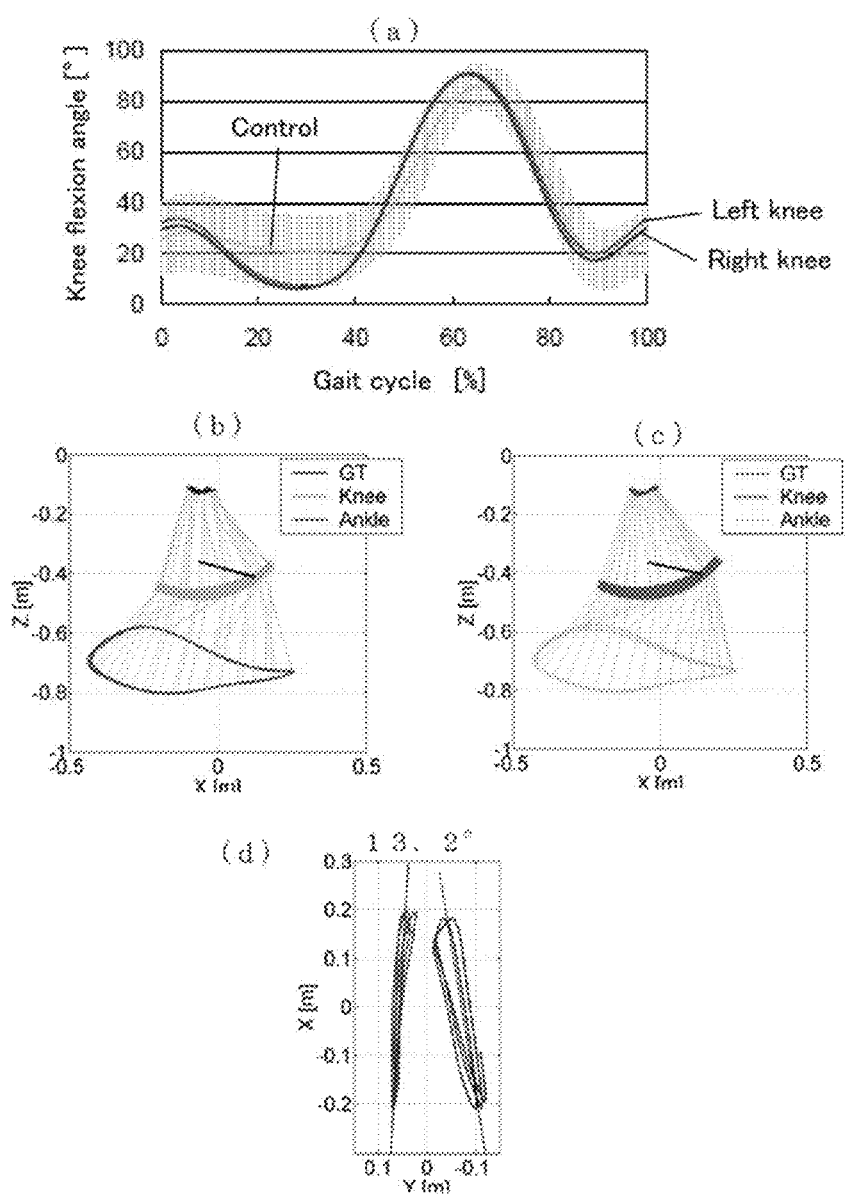
FIG. 35 is graphs illustrating results of measurement of gait of Patient F.
Figure 36:
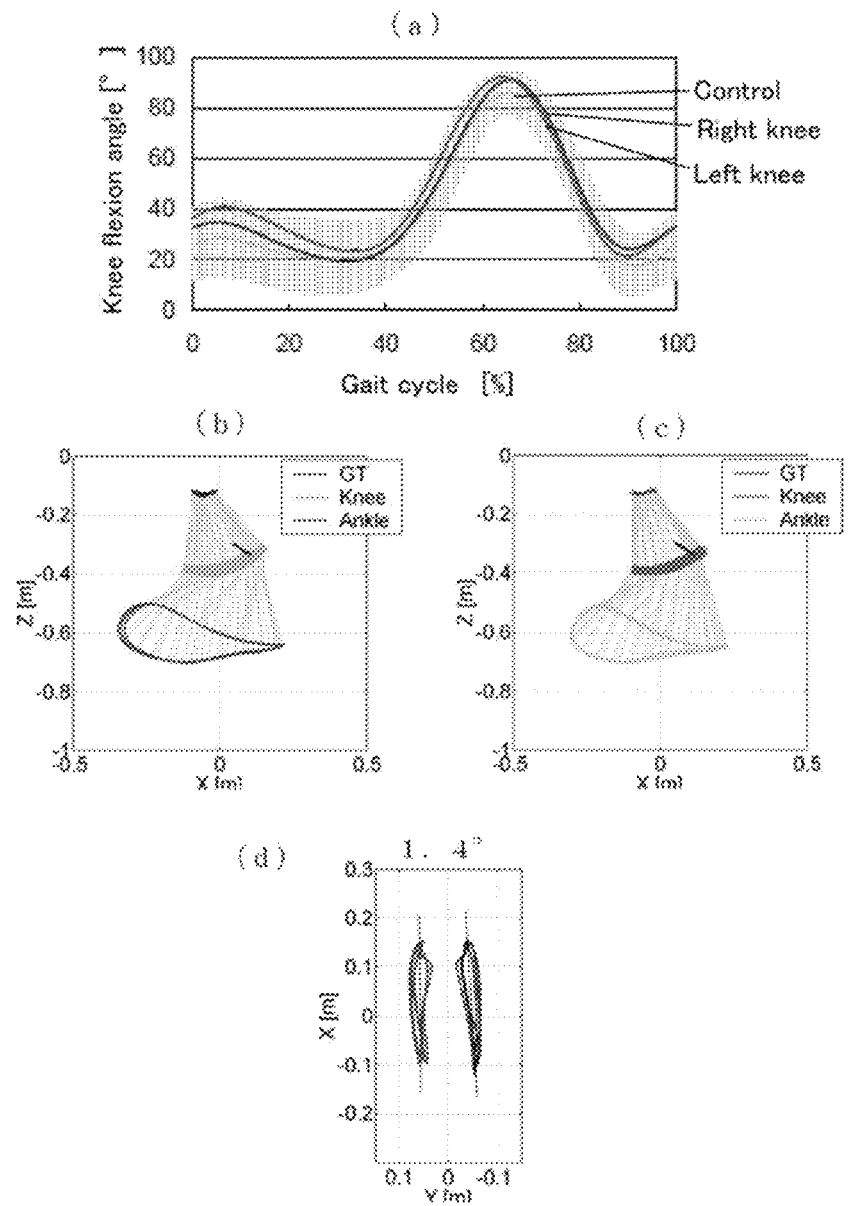
FIG. 36 is graphs illustrating results of measurement of gait of Patient G.
Figure 37:
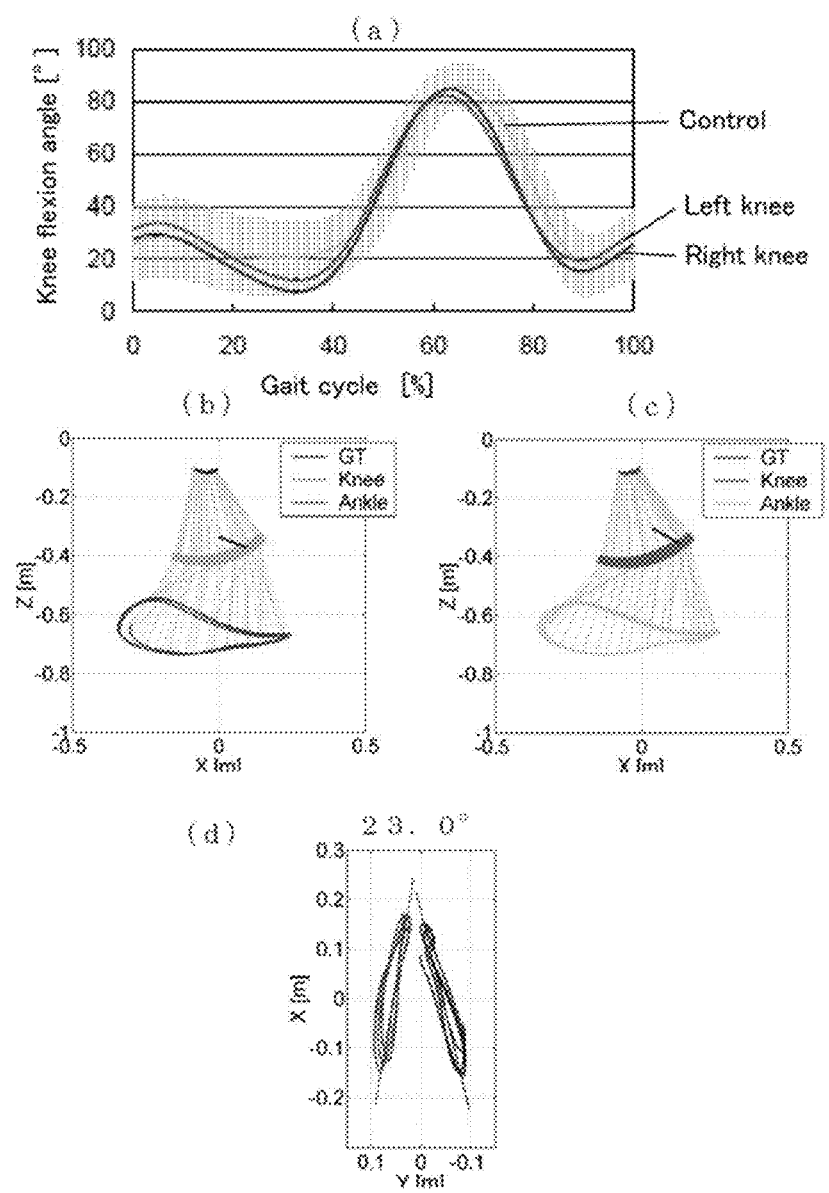
FIG. 37 is graphs illustrating results of measurement of gait of Patient H.
Figure 38:
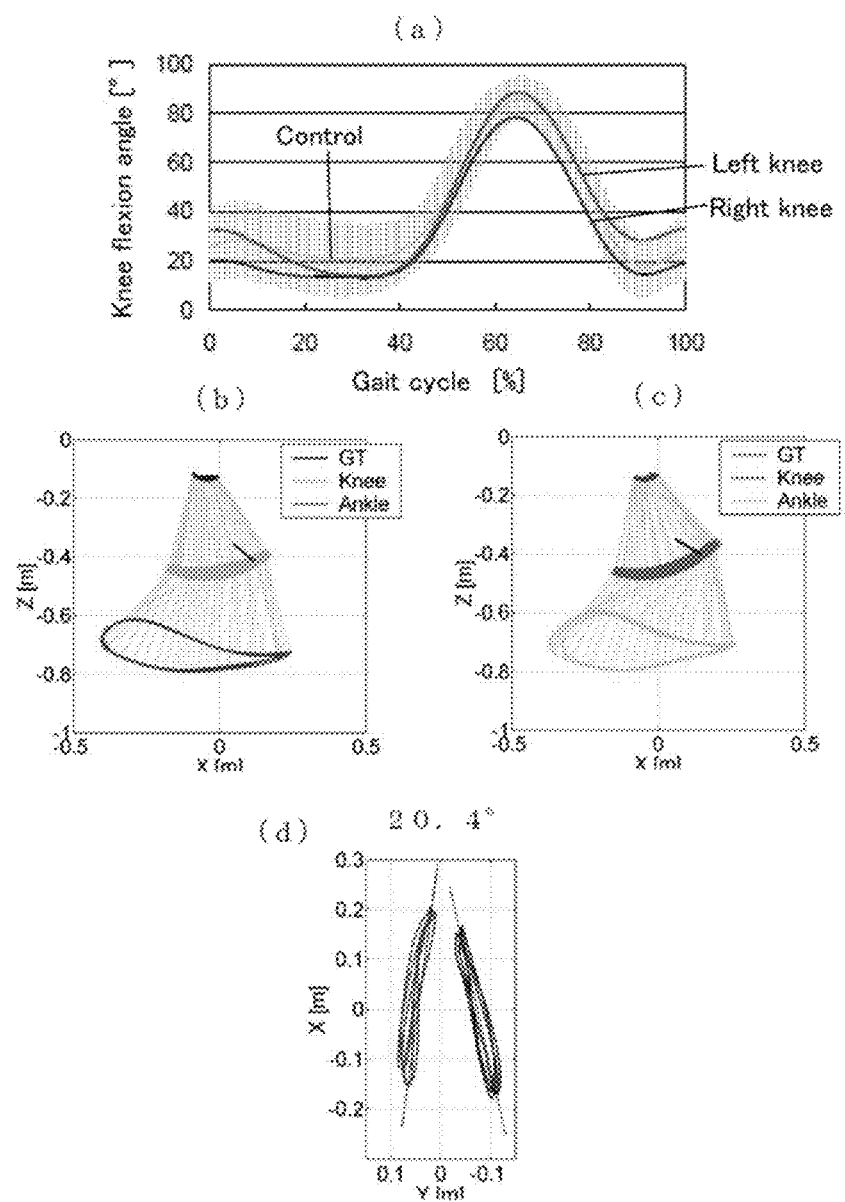
FIG. 38 is graphs illustrating results of measurement of gait of Patient I.
Figure 39:
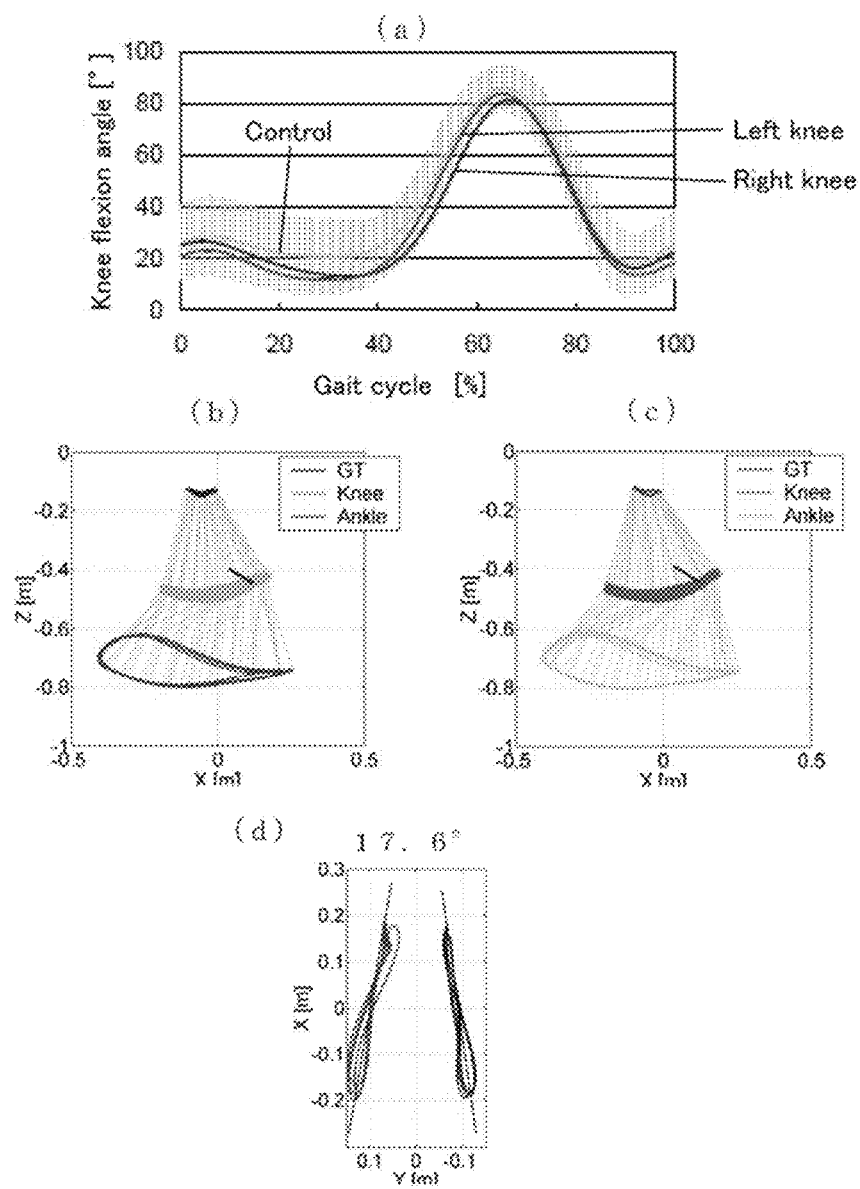
FIG. 39 is graphs illustrating results of measurement of gait of Patient J.
Figure 40:
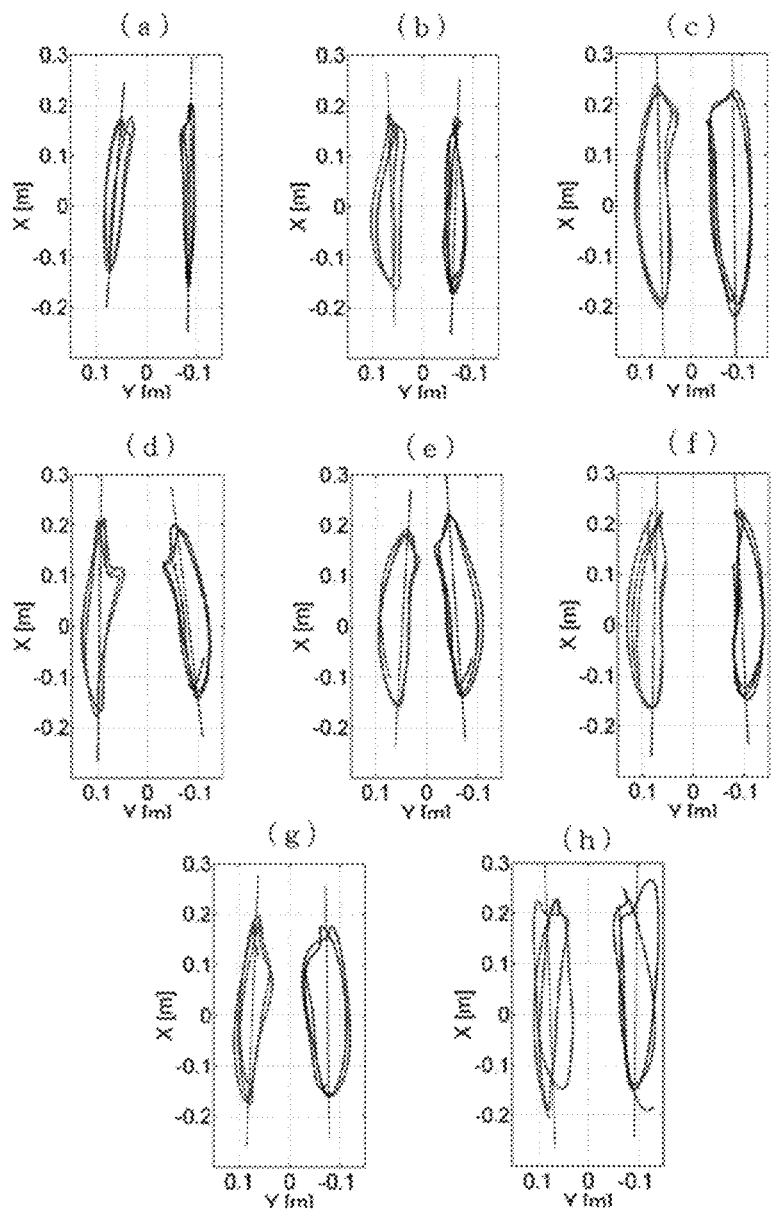
FIGS. 40(a) to (h) are graphs illustrating motion trajectories of knee joints of healthy persons in a horizontal plane.
Figure 41:
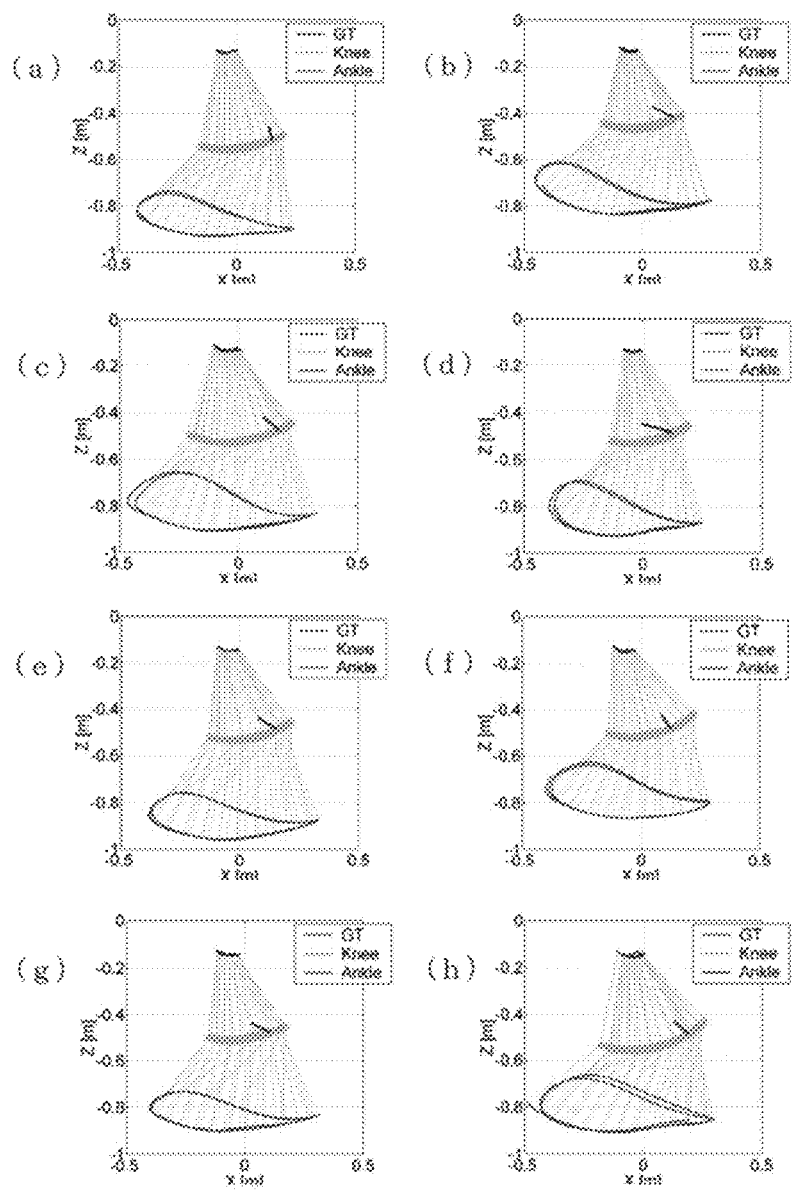
FIGS. 41(a) to (h) are graphs illustrating motion trajectories of joints of right legs of healthy persons in a sagittal plane and acceleration vectors at the time of heel contact.

The measurement results obtained by the gait measurements on the knee OA patients are indicated in Tables 7 to 16 and FIGS. 30 to 39. The Tables describe the parameters of three steps of each of the right leg and the left leg and their average values and standard deviations. Knee horizontal plane trajectory angles are calculated not for each gait cycle, but from the Lissajous figures of gait cycles, and therefore not described in the Tables. FIG. 30(*a*) is a graph of knee flexion angle. The vertical axis indicates the knee flexion angle, and the horizontal axis indicates the gait cycle. Gait cycles 0% and 100% are the timing of the heel contact. In addition to the right knee flexion angle and the left knee flexion angle, the Tables describe, in the light-colored lines and region, the average values of the healthy persons measured by Measurer $A_{1st}$ and its 95% confidence interval. The graphs are the average value of three gait cycles. FIGS. 30(*b*) and (*c*) illustrate the sagittal plane trajectory of the three gait cycles and the acceleration vector of the second step out of the three steps at the time of the heel contact. FIG. 30(*d*) indicates the knee joint horizontal plane trajectories of the three gait cycles. A knee horizontal plane trajectory angle $\theta_{xy}$ is described in the upper part of the drawing. Subsequently, similar drawings are illustrated regarding each patient up to FIG. 39. For reference, the sagittal plane trajectories and the knee horizontal plane trajectories of two gait cycles of the eight healthy persons are illustrated in FIGS. 40 and 41.

TABLE 7

|  |  | Number of steps | | | | Standard |
|---|---|---|---|---|---|---|
|  |  | 1st step | 2nd step | 3rd step | Average | deviation |
| Right leg | Step length [cm] | 38.9 | 34.0 | 39.8 | 37.6 | 3.2 |
|  | Max knee flexion angle in swing [°] | 76.3 | 79.2 | 79.8 | 78.5 | 1.9 |
|  | Max knee extension angle in stance [°] | 7.8 | 8.6 | 8.4 | 8.3 | 0.4 |
|  | Range of motion of knee joint [°] | 68.5 | 70.6 | 71.4 | 70.2 | 1.5 |
|  | Knee flexion angle (immediately after heel contact) [°] | 14.1 | 15.2 | 15.5 | 14.9 | 0.7 |
|  | Knee flexion angle (at the time of toe off) [°] | 51.7 | 54.3 | 58.1 | 54.7 | 3.2 |
|  | Ankle abduction angle [°] | −0.9 | 1.2 | 4.0 | 1.4 | 2.5 |
|  | Thigh and shank angle [°] | 175.5 | 176.7 | 174.5 | 175.6 | 1.1 |
|  | Lower limb functional axis inclination angle (abduction direction) [°] | −2.1 | −2.3 | −2.0 | −2.1 | 0.2 |
|  | Lower limb functional axis inclination angle (adduction direction) [°] | −5.0 | −5.4 | −4.3 | −4.9 | 0.6 |
|  | Gait cycle [s] | 1.11 | 1.13 | 1.16 | 1.13 | 0.02 |
|  | Stance ratio [%] | 59.0 | 59.8 | 56.7 | 58.5 | 1.6 |
|  | Direction of knee acceleration vector (at heel contact) [°] | 32.8 | 34.9 | 35.7 | 34.5 | 1.2 |
| Left leg | Step length [cm] | 46.1 | 49.3 | 47.6 | 47.7 | 1.6 |
|  | Max knee flexion angle in swing [°] | 70.9 | 72.4 | 73.9 | 72.4 | 2.6 |
|  | Max knee extension angle in stance [°] | 7.5 | 7.7 | 8.9 | 8.0 | 0.7 |
|  | Range of motion of knee joint [°] | 63.4 | 64.8 | 67.0 | 65.1 | 1.8 |
|  | Knee flexion angle (immediately after heel contact) [°] | 10.8 | 12.7 | 13.5 | 12.4 | 1.4 |
|  | Knee flexion angle (at the time of toe off) [°] | 51.6 | 52.8 | 50.2 | 51.5 | 1.3 |
|  | Ankle abduction angle [°] | −0.7 | −2.9 | −1.3 | −1.6 | 1.2 |
|  | Thigh and shank angle [°] | 176.7 | 177.8 | 178.3 | 177.6 | 0.8 |
|  | Lower limb functional axis inclination angle (abduction direction) [°] | −0.4 | −0.9 | −2.3 | −1.2 | 1.0 |
|  | Lower limb functional axis inclination angle (adduction direction) [°] | −5.4 | −5.7 | −5.4 | −5.5 | 0.2 |
|  | Gait cycle [s] | 1.12 | 1.10 | 1.18 | 1.13 | 0.04 |
|  | Stance ratio [%] | 54.5 | 54.5 | 55.7 | 54.9 | 0.7 |
|  | Direction of knee acceleration vector (at heel contact) [°] | 72.4 | 64.0 | 83.1 | 73.2 | 7.8 |

TABLE 8

|  |  | Number of steps | | | | Standard |
|---|---|---|---|---|---|---|
|  |  | 1st step | 2nd step | 3rd step | Average | deviation |
| Right leg | Step length [cm] | 63.4 | 60.7 | 62.5 | 62.2 | 1.9 |
|  | Max knee flexion angle in swing [°] | 81.7 | 81.6 | 81.7 | 81.7 | 0.1 |
|  | Max knee extension angle in stance [°] | 10.1 | 15.8 | 12.0 | 12.6 | 4.0 |
|  | Range of motion of knee joint [°] | 71.7 | 65.8 | 69.7 | 69.1 | 4.1 |
|  | Knee flexion angle (immediately after heel contact) [°] | 35.9 | 40.6 | 37.5 | 38.0 | 3.4 |
|  | Knee flexion angle (at the time of toe off) [°] | 57.4 | 59.9 | 58.2 | 58.5 | 1.8 |
|  | Ankle abduction angle [°] | 11.2 | 11.0 | 11.1 | 11.1 | 0.1 |
|  | Thigh and shank angle [°] | 187.1 | 187.8 | 187.3 | 187.4 | 0.5 |
|  | Lower limb functional axis inclination angle (abduction direction) [°] | 0.5 | 0.9 | 0.6 | 0.7 | 0.3 |

TABLE 8-continued

|  |  | 1st step | 2nd step | 3rd step | Average | Standard deviation |
|---|---|---|---|---|---|---|
|  | Lower limb functional axis inclination angle (adduction direction) [°] | −10.3 | −11.0 | −10.5 | −10.6 | 0.5 |
|  | Gait cycle [s] | 1.06 | 1.08 | 1.06 | 1.07 | 0.02 |
|  | Stance ratio [%] | 54.7 | 52.6 | 54.0 | 53.8 | 1.5 |
|  | Direction of knee acceleration vector (at heel contact) [°] | 43.6 | 38.7 | 46.6 | 43.0 | 3.3 |
| Left leg | Step length [cm] | 59.9 | 57.1 | 59.0 | 58.6 | 1.9 |
|  | Max knee flexion angle in swing [°] | 87.3 | 85.2 | 86.6 | 86.4 | 1.5 |
|  | Max knee extension angle in stance [°] | 14.4 | 14.7 | 14.5 | 14.5 | 0.2 |
|  | Range of motion of knee joint [°] | 72.9 | 70.5 | 72.1 | 71.9 | 1.7 |
|  | Knee flexion angle (immediately after heel contact) [°] | 41.4 | 37.1 | 39.9 | 39.4 | 3.0 |
|  | Knee flexion angle (at the time of toe off) [°] | 56.3 | 55.8 | 56.2 | 56.1 | 0.4 |
|  | Ankle abduction angle [°] | 2.6 | 3.5 | 2.9 | 3.0 | 0.6 |
|  | Thigh and shank angle [°] | 189.8 | 190.4 | 190.0 | 190.1 | 0.4 |
|  | Lower limb functional axis inclination angle (abduction direction) [°] | −2.3 | −2.7 | −2.5 | −2.5 | 0.3 |
|  | Lower limb functional axis inclination angle (adduction direction) [°] | −11.2 | −10.5 | −11.0 | −10.9 | 0.5 |
|  | Gait cycle [s] | 1.04 | 1.13 | 1.07 | 1.08 | 0.06 |
|  | Stance ratio [%] | 53.2 | 52.9 | 53.1 | 53.1 | 0.2 |
|  | Direction of knee acceleration vector (at heel contact) [°] | 49.4 | 47 | 49.3 | 48.6 | 1.1 |

TABLE 9

|  |  | 1st step | 2nd step | 3rd step | Average | Standard deviation |
|---|---|---|---|---|---|---|
| Right leg | Step length [cm] | 57.8 | 60.7 | 54.6 | 57.7 | 3.0 |
|  | Max knee flexion angle in swing [°] | 94.0 | 92.6 | 96.6 | 94.4 | 2.1 |
|  | Max knee extension angle in stance [°] | 18.0 | 18.3 | 17.5 | 17.9 | 0.4 |
|  | Range of motion of knee joint [°] | 76.0 | 74.2 | 79.1 | 76.5 | 2.5 |
|  | Knee flexion angle (immediately after heel contact) [°] | 38.0 | 39.4 | 41.2 | 39.5 | 1.6 |
|  | Knee flexion angle (at the time of toe off) [°] | 70.8 | 70.2 | 67.2 | 69.4 | 2.0 |
|  | Ankle abduction angle [°] | 13.1 | 16.9 | 16.2 | 15.4 | 2.0 |
|  | Thigh and shank angle [°] | 171.9 | 171.8 | 171.7 | 171.8 | 0.1 |
|  | Lower limb functional axis inclination angle (abduction direction) [°] | −0.7 | −1.2 | −2.2 | −1.4 | 0.7 |
|  | Lower limb functional axis inclination angle (adduction direction) [°] | −6.9 | −7.0 | −8.6 | −7.5 | 0.9 |
|  | Gait cycle [s] | 1.03 | 0.98 | 0.99 | 1.00 | 0.03 |
|  | Stance ratio [%] | 53.8 | 52.3 | 52.8 | 52.9 | 0.8 |
|  | Direction of knee acceleration vector (at heel contact) [°] | 46.4 | 44.1 | 41.2 | 43.9 | 2.1 |
| Left leg | Step length [cm] | 45.8 | 47.3 | 51.6 | 48.3 | 3.0 |
|  | Max knee flexion angle in swing [°] | 91.0 | 94.1 | 91.4 | 92.2 | 1.7 |
|  | Max knee extension angle in stance [°] | 20.1 | 21.8 | 21.9 | 21.3 | 1.0 |
|  | Range of motion of knee joint [°] | 70.9 | 72.3 | 69.5 | 70.9 | 1.4 |
|  | Knee flexion angle (immediately after heel contact) [°] | 41.8 | 47.0 | 47.3 | 45.4 | 3.1 |
|  | Knee flexion angle (at the time of toe off) [°] | 60.8 | 62.5 | 65.1 | 62.8 | 2.2 |
|  | Ankle abduction angle [°] | 4.8 | 4.9 | 3.1 | 4.3 | 1.0 |
|  | Thigh and shank angle [°] | 183.4 | 183.5 | 182.8 | 183.2 | 0.4 |
|  | Lower limb functional axis inclination angle (abduction direction) [°] | −0.6 | 0.0 | −2.1 | −0.9 | 1.1 |
|  | Lower limb functional axis inclination angle (adduction direction) [°] | −8.9 | −8.5 | −10.3 | −9.2 | 0.9 |
|  | Gait cycle [s] | 0.99 | 1.00 | 0.99 | 0.99 | 0.01 |
|  | Stance ratio [%] | 53.9 | 53.3 | 53.9 | 53.7 | 0.3 |
|  | Direction of knee acceleration vector (at heel contact) [°] | 40 | 43.8 | 53 | 45.6 | 5.5 |

TABLE 10

|  |  | Number of steps | | | | Standard |
|---|---|---|---|---|---|---|
|  |  | 1st step | 2nd step | 3rd step | Average | deviation |
| Right leg | Step length [cm] | 45.8 | 41.7 | 39.5 | 42.3 | 3.2 |
|  | Max knee flexion angle in swing [°] | 89.5 | 92.5 | 88.5 | 90.2 | 2.1 |
|  | Max knee extension angle in stance [°] | 15.9 | 14.2 | 16.8 | 15.6 | 1.3 |
|  | Range of motion of knee joint [°] | 73.6 | 78.4 | 71.7 | 74.5 | 3.4 |
|  | Knee flexion angle (immediately after heel contact) [°] | 26.8 | 19.6 | 22.5 | 23.0 | 3.6 |
|  | Knee flexion angle (at the time of toe off) [°] | 66.7 | 70.1 | 70.0 | 69.0 | 1.9 |
|  | Ankle abduction angle [°] | −1.3 | 4.9 | 5.3 | 3.0 | 3.7 |
|  | Thigh and shank angle [°] | 172.8 | 174.4 | 175.2 | 174.2 | 1.2 |
|  | Lower limb functional axis inclination angle (abduction direction) [°] | 0.6 | −0.5 | 0.0 | 0.1 | 0.5 |
|  | Lower limb functional axis inclination angle (adduction direction) [°] | −5.3 | −6.5 | −5.9 | −5.9 | 0.6 |
|  | Gait cycle [s] | 1.09 | 1.07 | 1.07 | 1.07 | 0.01 |
|  | Stance ratio [%] | 53.1 | 55.2 | 54.2 | 54.1 | 1.1 |
|  | Direction of knee acceleration vector (at heel contact) [°] | 39 | 54.6 | 37.3 | 43.6 | 7.8 |
| Left leg | Step length [cm] | 43.4 | 42.2 | 44.5 | 43.4 | 1.2 |
|  | Max knee flexion angle in swing [°] | 84.0 | 85.1 | 83.7 | 84.3 | 0.8 |
|  | Max knee extension angle in stance [°] | 19.5 | 20.9 | 22.7 | 21.0 | 1.6 |
|  | Range of motion of knee joint [°] | 64.6 | 64.3 | 61.0 | 63.3 | 2.0 |
|  | Knee flexion angle (immediately after heel contact) [°] | 25.2 | 26.8 | 27.3 | 26.4 | 1.1 |
|  | Knee flexion angle (at the time of toe off) [°] | 61.5 | 61.2 | 63.6 | 62.1 | 1.3 |
|  | Ankle abduction angle [°] | 3.1 | 1.6 | 0.4 | 1.7 | 1.4 |
|  | Thigh and shank angle [°] | 179.2 | 177.6 | 177.7 | 178.2 | 0.9 |
|  | Lower limb functional axis inclination angle (abduction direction) [°] | −2.8 | −2.5 | −5.5 | −3.6 | 1.7 |
|  | Lower limb functional axis inclination angle (adduction direction) [°] | −6.3 | −6.6 | −8.0 | −7.0 | 0.9 |
|  | Gait cycle [s] | 1.08 | 1.08 | 1.06 | 1.07 | 0.01 |
|  | Stance ratio [%] | 55.7 | 55.7 | 56.8 | 56.1 | 0.7 |
|  | Direction of knee acceleration vector (at heel contact) [°] | 39.6 | 47.9 | 53.6 | 47.0 | 5.7 |

TABLE 11

|  |  | Number of steps | | | | Standard |
|---|---|---|---|---|---|---|
|  |  | 1st step | 2nd step | 3rd step | Average | deviation |
| Right leg | Step length [cm] | 47.4 | 46.9 | 41.1 | 45.1 | 3.5 |
|  | Max knee flexion angle in swing [°] | 73.2 | 74.0 | 75.1 | 74.1 | 1.0 |
|  | Max knee extension angle in stance [°] | 7.3 | 8.7 | 9.0 | 8.3 | 0.9 |
|  | Range of motion of knee joint [°] | 65.9 | 65.3 | 66.1 | 65.8 | 0.4 |
|  | Knee flexion angle (immediately after heel contact) [°] | 19.4 | 22.0 | 14.8 | 18.8 | 3.7 |
|  | Knee flexion angle (at the time of toe off) [°] | 56.9 | 52.2 | 57.3 | 55.5 | 2.8 |
|  | Ankle abduction angle [°] | 4.8 | 2.8 | 9.3 | 5.6 | 3.3 |
|  | Thigh and shank angle [°] | 175.4 | 171.4 | 175.3 | 174.0 | 2.3 |
|  | Lower limb functional axis inclination angle (abduction direction) [°] | −2.0 | −1.1 | −3.5 | −2.2 | 1.2 |
|  | Lower limb functional axis inclination angle (adduction direction) [°] | −7.3 | −6.2 | −8.6 | −7.4 | 1.2 |
|  | Gait cycle [s] | 1.22 | 1.29 | 1.37 | 1.29 | 0.07 |
|  | Stance ratio [%] | 59.1 | 61.2 | 62.6 | 61.0 | 1.8 |
|  | Direction of knee acceleration vector (at heel contact) [°] | 59.8 | 59.8 | 54.1 | 57.9 | 2.7 |
| Left leg | Step length [cm] | 39.3 | 34.1 | 35.7 | 36.3 | 2.7 |
|  | Max knee flexion angle in swing [°] | 78.2 | 73.3 | 71.9 | 74.5 | 3.3 |
|  | Max knee extension angle in stance [°] | 13.9 | 16.7 | 17.2 | 15.9 | 1.8 |
|  | Range of motion of knee joint [°] | 64.3 | 56.6 | 54.7 | 58.6 | 5.1 |
|  | Knee flexion angle (immediately after heel contact) [°] | 20.6 | 31.2 | 28.5 | 26.8 | 5.5 |
|  | Knee flexion angle (at the time of toe off) [°] | 51.5 | 47.2 | 53.9 | 50.9 | 3.4 |
|  | Ankle abduction angle [°] | −7.5 | −19.1 | −17.7 | −14.8 | 6.3 |
|  | Thigh and shank angle [°] | 177.3 | 172.4 | 172.7 | 174.2 | 2.8 |

TABLE 11-continued

|  | 1st step | 2nd step | 3rd step | Average | Standard deviation |
|---|---|---|---|---|---|
| Lower limb functional axis inclination angle (abduction direction) [°] | −6.3 | −5.9 | −4.4 | −5.6 | 1.0 |
| Lower limb functional axis inclination angle (adduction direction) [°] | −10.6 | −9.0 | −11.4 | −10.3 | 1.3 |
| Gait cycle [s] | 1.22 | 1.43 | 1.33 | 1.33 | 0.11 |
| Stance ratio [%] | 60.9 | 52.7 | 55.0 | 56.2 | 4.2 |
| Direction of knee acceleration vector (at heel contact) [°] | 58.6 | 76.9 | 18.1 | 51.2 | 24.6 |

TABLE 12

| | | 1st step | 2nd step | 3rd step | Average | Standard deviation |
|---|---|---|---|---|---|---|
| Right leg | Step length [cm] | 68.7 | 62.4 | 66.6 | 65.5 | 4.4 |
| | Max knee flexion angle in swing [°] | 90.9 | 91.0 | 90.9 | 91.0 | 0.1 |
| | Max knee extension angle in stance [°] | 6.1 | 6.4 | 6.2 | 6.2 | 0.2 |
| | Range of motion of knee joint [°] | 84.8 | 84.7 | 84.8 | 84.7 | 0.1 |
| | Knee flexion angle (immediately after heel contact) [°] | 31.0 | 31.5 | 31.2 | 31.2 | 0.3 |
| | Knee flexion angle (at the time of toe off) [°] | 56.6 | 51.6 | 54.9 | 54.1 | 3.5 |
| | Ankle abduction angle [°] | 9.2 | 9.7 | 9.4 | 9.5 | 0.4 |
| | Thigh and shank angle [°] | 178.8 | 179.8 | 179.1 | 179.3 | 0.7 |
| | Lower limb functional axis inclination angle (abduction direction) [°] | 3.1 | 4.8 | 3.7 | 3.9 | 1.2 |
| | Lower limb functional axis inclination angle (adduction direction) [°] | −10.1 | −9.2 | −9.8 | −9.7 | 0.6 |
| | Gait cycle [s] | 0.90 | 0.88 | 0.89 | 0.89 | 0.02 |
| | Stance ratio [%] | 51.9 | 49.4 | 51.0 | 50.6 | 1.8 |
| | Direction of knee acceleration vector (at heel contact) [°] | 38.5 | 38.3 | 39.7 | 38.8 | 0.6 |
| Left leg | Step length [cm] | 62.1 | 65.9 | 63.4 | 64.0 | 2.7 |
| | Max knee flexion angle in swing [°] | 93.1 | 90.0 | 92.1 | 91.6 | 2.2 |
| | Max knee extension angle in stance [°] | 7.0 | 7.5 | 7.2 | 7.3 | 0.3 |
| | Range of motion of knee joint [°] | 86.1 | 82.5 | 84.9 | 84.3 | 2.5 |
| | Knee flexion angle (immediately after heel contact) [°] | 33.9 | 33.9 | 33.9 | 33.9 | 0.0 |
| | Knee flexion angle (at the time of toe off) [°] | 52.3 | 54.6 | 53.1 | 53.5 | 1.6 |
| | Ankle abduction angle [°] | 8.3 | 2.0 | 6.2 | 5.2 | 4.4 |
| | Thigh and shank angle [°] | 170.9 | 170.7 | 170.9 | 170.8 | 0.2 |
| | Lower limb functional axis inclination angle (abduction direction) [°] | 2.8 | 2.3 | 2.6 | 2.6 | 0.4 |
| | Lower limb functional axis inclination angle (adduction direction) [°] | −6.2 | −6.2 | −6.2 | −6.2 | 0.0 |
| | Gait cycle [s] | 0.88 | 0.89 | 0.88 | 0.88 | 0.01 |
| | Stance ratio [%] | 49.4 | 51.3 | 50.0 | 50.3 | 1.3 |
| | Direction of knee acceleration vector (at heel contact) [°] | 44.6 | 46.6 | 44.6 | 45.3 | 0.9 |

TABLE 13

| | | 1st step | 2nd step | 3rd step | Average | Standard deviation |
|---|---|---|---|---|---|---|
| Right leg | Step length [cm] | 43.8 | 44.1 | 44.8 | 44.2 | 0.5 |
| | Max knee flexion angle in swing [°] | 91.4 | 91.9 | 91.5 | 91.6 | 0.3 |
| | Max knee extension angle in stance [°] | 19.8 | 19.3 | 15.9 | 18.3 | 2.1 |
| | Range of motion of knee joint [°] | 71.6 | 72.6 | 75.6 | 73.3 | 2.1 |
| | Knee flexion angle (immediately after heel contact) [°] | 33.5 | 35.7 | 34.5 | 34.6 | 1.1 |
| | Knee flexion angle (at the time of toe off) [°] | 74.9 | 75.7 | 71.1 | 73.9 | 2.4 |
| | Ankle abduction angle [°] | −2.3 | −3.3 | 0.5 | −1.7 | 2.0 |
| | Thigh and shank angle [°] | 170.9 | 172.9 | 173.1 | 172.3 | 1.2 |
| | Lower limb functional axis inclination angle (abduction direction) [°] | −2.9 | −5.4 | −4.5 | −4.3 | 1.2 |

TABLE 13-continued

| | | Number of steps | | | | Standard deviation |
|---|---|---|---|---|---|---|
| | | 1st step | 2nd step | 3rd step | Average | |
| | Lower limb functional axis inclination angle (adduction direction) [°] | −7.8 | −8.2 | −7.2 | −7.7 | 0.5 |
| | Gait cycle [s] | 1.16 | 1.08 | 1.07 | 1.10 | 0.05 |
| | Stance ratio [%] | 59.6 | 56.7 | 55.2 | 57.2 | 2.2 |
| | Direction of knee acceleration vector (at heel contact) [°] | 61.3 | 71.8 | 66 | 66.4 | 4.3 |
| Left leg | Step length [cm] | 43.3 | 46.4 | 49.0 | 46.2 | 2.8 |
| | Max knee flexion angle in swing [°] | 92.1 | 93.0 | 90.4 | 91.8 | 1.3 |
| | Max knee extension angle in stance [°] | 21.4 | 21.8 | 21.5 | 21.5 | 0.2 |
| | Range of motion of knee joint [°] | 70.7 | 71.2 | 69.0 | 70.3 | 1.2 |
| | Knee flexion angle (immediately after heel contact) [°] | 44.0 | 37.6 | 35.5 | 39.0 | 4.4 |
| | Knee flexion angle (at the time of toe off) [°] | 71.8 | 75.6 | 72.7 | 73.4 | 2.0 |
| | Ankle abduction angle [°] | −8.1 | −6.4 | −5.7 | −6.7 | 1.3 |
| | Thigh and shank angle [°] | 174.9 | 174.4 | 174.2 | 174.5 | 0.3 |
| | Lower limb functional axis inclination angle (abduction direction) [°] | −1.7 | −3.4 | −3.9 | −3.0 | 1.1 |
| | Lower limb functional axis inclination angle (adduction direction) [°] | −4.2 | −4.5 | −5.8 | −4.9 | 0.9 |
| | Gait cycle [s] | 1.09 | 1.07 | 1.10 | 1.09 | 0.02 |
| | Stance ratio [%] | 56.1 | 55.2 | 55.6 | 55.6 | 0.5 |
| | Direction of knee acceleration vector (at heel contact) [°] | 60 | 59.5 | 61.9 | 60.5 | 1.0 |

TABLE 14

| | | Number of steps | | | | Standard deviation |
|---|---|---|---|---|---|---|
| | | 1st step | 2nd step | 3rd step | Average | |
| Right leg | Step length [cm] | 53.5 | 53.2 | 53.9 | 53.5 | 0.4 |
| | Max knee flexion angle in swing [°] | 83.5 | 87.3 | 87.8 | 86.2 | 2.4 |
| | Max knee extension angle in stance [°] | 5.5 | 9.2 | 8.9 | 7.8 | 2.0 |
| | Range of motion of knee joint [°] | 78.0 | 78.1 | 78.9 | 78.3 | 0.5 |
| | Knee flexion angle (immediately after heel contact) [°] | 30.7 | 28.5 | 27.8 | 29.0 | 1.5 |
| | Knee flexion angle (at the time of toe off) [°] | 59.2 | 59.8 | 60.9 | 60.0 | 0.8 |
| | Ankle abduction angle [°] | −2.9 | −1.1 | −2.0 | −2.0 | 0.9 |
| | Thigh and shank angle [°] | 176.7 | 177.5 | 177.3 | 177.2 | 0.4 |
| | Lower limb functional axis inclination angle (abduction direction) [°] | 1.5 | 1.3 | 2.6 | 1.8 | 0.7 |
| | Lower limb functional axis inclination angle (adduction direction) [°] | −8.0 | −8.0 | −7.7 | −7.9 | 0.1 |
| | Gait cycle [s] | 0.99 | 0.94 | 0.97 | 0.97 | 0.02 |
| | Stance ratio [%] | 55.1 | 51.8 | 51.7 | 52.8 | 1.9 |
| | Direction of knee acceleration vector (at heel contact) [°] | 67.1 | 47.5 | 55.3 | 56.6 | 8.1 |
| Left leg | Step length [cm] | 49.1 | 54.8 | 55.5 | 53.1 | 3.5 |
| | Max knee flexion angle in swing [°] | 82.0 | 83.0 | 84.9 | 83.3 | 1.5 |
| | Max knee extension angle in stance [°] | 10.5 | 13.2 | 14.9 | 12.9 | 2.2 |
| | Range of motion of knee joint [°] | 71.5 | 69.7 | 70.0 | 70.4 | 1.0 |
| | Knee flexion angle (immediately after heel contact) [°] | 33.3 | 34.4 | 33.0 | 33.6 | 0.7 |
| | Knee flexion angle (at the time of toe off) [°] | 61.3 | 63.2 | 61.0 | 61.8 | 1.2 |
| | Ankle abduction angle [°] | 2.7 | −0.4 | 0.5 | 0.9 | 1.6 |
| | Thigh and shank angle [°] | 183.4 | 183.7 | 185.4 | 184.2 | 1.1 |
| | Lower limb functional axis inclination angle (abduction direction) [°] | −0.4 | −2.1 | −3.6 | −2.0 | 1.6 |
| | Lower limb functional axis inclination angle (adduction direction) [°] | −6.5 | −7.3 | −7.2 | −7.0 | 0.4 |
| | Gait cycle [s] | 0.96 | 0.96 | 0.97 | 0.96 | 0.01 |
| | Stance ratio [%] | 53.5 | 53.5 | 52.9 | 53.3 | 0.4 |
| | Direction of knee acceleration vector (at heel contact) [°] | 55.3 | 62.6 | 55.7 | 57.9 | 3.4 |

TABLE 15

|  |  | Number of steps | | | | Standard |
|---|---|---|---|---|---|---|
|  |  | 1st step | 2nd step | 3rd step | Average | deviation |
| Right leg | Step length [cm] | 50.3 | 51.4 | 46.9 | 49.5 | 2.4 |
|  | Max knee flexion angle in swing [°] | 78.1 | 78.9 | 79.4 | 78.8 | 0.6 |
|  | Max knee extension angle in stance [°] | 13.8 | 12.8 | 12.6 | 13.0 | 0.6 |
|  | Range of motion of knee joint [°] | 64.4 | 66.1 | 66.8 | 65.8 | 1.2 |
|  | Knee flexion angle (immediately after heel contact) [°] | 18.4 | 22.5 | 17.4 | 19.4 | 2.7 |
|  | Knee flexion angle (at the time of toe off) [°] | 54.5 | 56.9 | 54.0 | 55.1 | 1.5 |
|  | Ankle abduction angle [°] | 4.5 | 7.9 | 3.2 | 5.2 | 2.4 |
|  | Thigh and shank angle [°] | 180.1 | 178.3 | 178.0 | 178.8 | 1.1 |
|  | Lower limb functional axis inclination angle (abduction direction) [°] | 2.1 | 2.2 | 1.4 | 1.9 | 0.5 |
|  | Lower limb functional axis inclination angle (adduction direction) [°] | −9.9 | −9.7 | −10.7 | −10.1 | 0.6 |
|  | Gait cycle [s] | 1.04 | 1.04 | 1.04 | 1.04 | 0.00 |
|  | Stance ratio [%] | 55.3 | 54.3 | 54.3 | 54.6 | 0.6 |
|  | Direction of knee acceleration vector (at heel contact) [°] | 54 | 64.3 | 59.5 | 59.3 | 4.2 |
| Left leg | Step length [cm] | 57.8 | 55.2 | 60.7 | 57.9 | 2.8 |
|  | Max knee flexion angle in swing [°] | 87.8 | 89.6 | 86.7 | 88.0 | 1.5 |
|  | Max knee extension angle in stance [°] | 13.6 | 14.5 | 19.1 | 15.7 | 3.0 |
|  | Range of motion of knee joint [°] | 74.2 | 75.1 | 67.6 | 72.3 | 4.1 |
|  | Knee flexion angle (immediately after heel contact) [°] | 33.2 | 32.0 | 34.9 | 33.4 | 1.4 |
|  | Knee flexion angle (at the time of toe off) [°] | 60.5 | 58.6 | 62.7 | 60.6 | 2.1 |
|  | Ankle abduction angle [°] | 3.1 | 1.0 | 1.1 | 1.7 | 1.2 |
|  | Thigh and shank angle [°] | 180.1 | 179.5 | 180.4 | 180.0 | 0.5 |
|  | Lower limb functional axis inclination angle (abduction direction) [°] | −4.4 | −3.8 | −4.1 | −4.1 | 0.3 |
|  | Lower limb functional axis inclination angle (adduction direction) [°] | −9.1 | −7.7 | −9.0 | −8.6 | 0.8 |
|  | Gait cycle [s] | 1.02 | 1.06 | 1.08 | 1.05 | 0.03 |
|  | Stance ratio [%] | 55.4 | 53.7 | 52.6 | 53.9 | 1.4 |
|  | Direction of knee acceleration vector (at heel contact) [°] | 60.8 | 60.4 | 65.1 | 62.1 | 2.1 |

TABLE 16

|  |  | Number of steps | | | | Standard |
|---|---|---|---|---|---|---|
|  |  | 1st step | 2nd step | 3rd step | Average | deviation |
| Right leg | Step length [cm] | 50.3 | 54.2 | 54.0 | 52.8 | 2.2 |
|  | Max knee flexion angle in swing [°] | 82.9 | 80.6 | 82.4 | 82.0 | 1.2 |
|  | Max knee extension angle in stance [°] | 13.1 | 12.5 | 13.3 | 13.0 | 0.4 |
|  | Range of motion of knee joint [°] | 69.8 | 68.1 | 69.1 | 69.0 | 0.9 |
|  | Knee flexion angle (immediately after heel contact) [°] | 28.9 | 25.6 | 26.1 | 26.9 | 1.8 |
|  | Knee flexion angle (at the time of toe off) [°] | 55.1 | 55.1 | 56.6 | 55.6 | 0.9 |
|  | Ankle abduction angle [°] | −0.2 | −0.6 | −0.4 | −0.4 | 0.2 |
|  | Thigh and shank angle [°] | 178.7 | 180.9 | 181.2 | 180.2 | 1.4 |
|  | Lower limb functional axis inclination angle (abduction direction) [°] | 2.2 | 1.5 | 1.8 | 1.9 | 0.4 |
|  | Lower limb functional axis inclination angle (adduction direction) [°] | −8.2 | −8.2 | −8.8 | −8.4 | 0.3 |
|  | Gait cycle [s] | 1.07 | 1.06 | 1.04 | 1.06 | 0.01 |
|  | Stance ratio [%] | 58.3 | 56.8 | 55.3 | 56.8 | 1.5 |
|  | Direction of knee acceleration vector (at heel contact) [°] | 65.1 | 54.8 | 46.5 | 55.5 | 7.6 |
| Left leg | Step length [cm] | 53.4 | 55.6 | 56.4 | 55.1 | 1.5 |
|  | Max knee flexion angle in swing [°] | 82.5 | 86.5 | 84.5 | 84.5 | 2.0 |
|  | Max knee extension angle in stance [°] | 13.3 | 10.3 | 11.8 | 11.8 | 1.5 |
|  | Range of motion of knee joint [°] | 69.2 | 76.1 | 72.7 | 72.7 | 3.5 |
|  | Knee flexion angle (immediately after heel contact) [°] | 26.0 | 22.5 | 22.0 | 23.5 | 2.2 |
|  | Knee flexion angle (at the time of toe off) [°] | 60.2 | 57.0 | 59.1 | 58.7 | 1.6 |
|  | Ankle abduction angle [°] | 0.5 | −0.3 | −1.9 | −0.6 | 1.3 |
|  | Thigh and shank angle [°] | 185.3 | 184.3 | 185.7 | 185.1 | 0.7 |
|  | Lower limb functional axis inclination angle (abduction direction) [°] | 4.0 | 3.1 | 2.9 | 3.3 | 0.5 |

TABLE 16-continued

|  | Number of steps | | | | Standard |
|---|---|---|---|---|---|
|  | 1st step | 2nd step | 3rd step | Average | deviation |
| Lower limb functional axis inclination angle (adduction direction) [°] | −7.0 | −7.8 | −8.3 | −7.7 | 0.7 |
| Gait cycle [s] | 1.03 | 1.04 | 1.08 | 1.05 | 0.02 |
| Stance ratio [%] | 53.8 | 56.4 | 55.7 | 55.3 | 1.4 |
| Direction of knee acceleration vector (at heel contact) [°] | 42.9 | 54.9 | 55.5 | 51.1 | 5.8 |

(Reproducibility of Measurement)

Regarding reproducibility of measurement, referring to Table 3, a comparison of level ground gait between measurement dates, there can be seen no significant difference in any of the parameters, and reproducibility can be recognized. Referring to Table 4, a comparison between the measurers, it can be seen that there are significant differences between the maximum knee flexion angles, the minimum knee flexion angles, and the knee flexions at the time of the toe off. This is presumably because of a difference in attachment position of the markers for use in determining the segment coordinate system. In particular, the marker of the great trochanter is technically attached to the outermost point of the great trochanter. However, because the great trochanter is a relatively large landmark, misalignment tends to occur. However, this problem is not specific to the system of the present invention, but is a problem that can similarly occur in a different system using a marker, e.g., an optical system.

(Quantitative Assessment of Knee OA Symptoms)

Next, the results of measurement of Patient A are taken as an example to describe the quantitative assessment of knee OA symptoms. Referring to FIG. 30(a), first, it can be seen that the peak value of the flexion angle of the left knee the severity of which is higher is significantly smaller than that of the healthy persons. This indicates restrictions on knee flexion due to knee pain. While the average value of the maximum knee flexion angles of the healthy persons is 84.9°, the left knee of Patient A is 72.4°. In addition, there is a large difference in step length between the right and left due to knee pain in the left knee. While the ratio of the right and left step lengths (right step length/left step length) of the healthy group is 1.02±0.08, almost the same between the right and the left, the right and left ratio of Patient A is 0.79. In addition, similarly due to knee pain in the left knee, there is also a difference in stance ratio between the right and the left, and its value is also obtained as a measurement result.

(Comparison Between the Patient Group and the Healthy Group)

Tables 17 to 20 described below indicate results of comparisons between the gait parameters of the patient group and the healthy group. The Tables respectively indicate comparisons of the parameters of the right leg, the left leg, the side with higher severity, and the side with lower severity. Table 2 described above indicates which leg has higher severity. Regarding the patients and the healthy persons whose severity is comparable between the right and the left, the average values of the right and left legs were used for both the side with higher severity and the side with lower severity. The p values in the Tables are values obtained when an unpaired t-test was conducted.

TABLE 17

| Right leg | Knee OA group Average (Standard deviation) | Healthy group Average (Standard deviation) | p-value |
|---|---|---|---|
| Step length [cm] | 50.7 (8.6) | 59.3 (4.0) | 0.025 |
| Max knee flexion angle in swing [°] | 86.4 (6.5) | 85.3 (6.8) | 0.758 |
| Max knee extension angle in stance [°] | 11.2 (3.7) | 14.1 (5.6) | 0.228 |
| Range of motion of knee joint [°] | 74.3 (5.8) | 71.0 (6.6) | 0.305 |
| Knee flexion angle (immediately after heel contact) [°] | 29.8 (7.6) | 27.8 (6.2) | 0.563 |
| Knee flexion angle (at the time of toe off) [°] | 62.4 (6.8) | 61.1 (4.9) | 0.668 |
| Ankle abduction angle [°] | 6.4 (5.4) | 8.5 (7.9) | 0.520 |
| Thigh and shank angle [°] | 177.1 (4.5) | 182.0 (8.1) | 0.145 |
| Lower limb functional axis inclination angle (abduction direction) [°] | −0.3 (2.0) | −1.7 (2.4) | 0.224 |
| Lower limb functional axis inclination angle (adduction direction) [°] | −8.5 (1.9) | −7.4 (1.5) | 0.207 |
| Gait cycle [s] | 1.07 (0.10) | 1.19 (0.08) | 0.018 |
| Stance ratio [%] | 55.4 (2.8) | 54.7 (2.0) | 0.569 |
| Angle between right and left knee joint tranjectory [°] | 7.4 (5.3) | 1.6 (2.8) | 0.018 |
| Direction of knee acceleration vector (at heel contact) [°] | 49.9 (9.9) | 61.7 (13.1) | 0.058 |

TABLE 18

| Left leg | Knee OA group Average (Standard deviation) | Healthy group Average (Standard deviation) | p-value |
|---|---|---|---|
| Step length [cm] | 50.8 (7.1) | 57.5 (5.1) | 0.048 |
| Max knee flexion angle in swing [°] | 87.0 (5.4) | 84.5 (5.1) | 0.366 |
| Max knee extension angle in stance [°] | 13.5 (4.7) | 12.6 (3.9) | 0.672 |
| Range of motion of knee joint [°] | 72.4 (6.2) | 70.9 (6.2) | 0.651 |
| Knee flexion angle (immediately after heel contact) [°] | 33.6 (9.0) | 27.7 (7.0) | 0.171 |
| Knee flexion angle (at the time of toe off) [°] | 61.1 (5.7) | 60.7 (4.9) | 0.858 |
| Ankle abduction angle [°] | 1.5 (5.0) | 5.1 (10.1) | 0.360 |
| Thigh and shank angle [°] | 180.1 (4.8) | 183.0 (9.6) | 0.392 |
| Lower limb functional axis inclination angle (abduction direction) [°] | −0.8 (2.7) | −3.1 (2.5) | 0.092 |

TABLE 18-continued

| Left leg | Knee OA group Average (Standard deviation) | Healthy group Average (Standard deviation) | p-value |
|---|---|---|---|
| Lower limb functional axis inclination angle (adduction direction) [°] | −8.4 (2.1) | −8.2 (1.2) | 0.805 |
| Gait cycle [s] | 1.06 (0.11) | 1.19 (0.09) | 0.020 |
| Stance ratio [%] | 54.3 (1.8) | 55.6 (1.8) | 0.181 |
| Angle between right and left knee joint tranjectory [°] | 7.2 (3.9) | 1.0 (2.4) | 0.002 |
| Direction of knee acceleration vector (at heel contact) [°] | 54.2 (8.5) | 60.3 (9.1) | 0.190 |

TABLE 19

| Higher severity side | Knee OA group Average (Standard deviation) | Healthy group Average (Standard deviation) | p-value |
|---|---|---|---|
| Step length [cm] | 50.3 (6.1) | 58.4 (3.9) | 0.007 |
| Max knee flexion angle in swing [°] | 85.5 (6.1) | 84.9 (5.5) | 0.843 |
| Max knee extension angle in stance [°] | 12.7 (3.8) | 13.3 (4.7) | 0.766 |
| Range of motion of knee joint [°] | 71.8 (6.4) | 71.0 (6.0) | 0.795 |
| Knee flexion angle (immediately after heel contact) [°] | 31.1 (8.4) | 27.7 (6.5) | 0.389 |
| Knee flexion angle (at the time of toe off) [°] | 60.9 (6.1) | 60.9 (4.0) | 0.991 |
| Ankle abduction angle [°] | 3.9 (4.2) | 6.8 (8.9) | 0.398 |
| Thigh and shank angle [°] | 178.8 (5.0) | 184.5 (8.0) | 0.100 |
| Lower limb functional axis inclination angle (abduction direction) [°] | −0.7 (2.1) | −2.4 (2.0) | 0.126 |
| Lower limb functional axis inclination angle (adduction direction) [°] | −8.6 (1.7) | −7.8 (1.0) | 0.292 |

TABLE 19-continued

| Higher severity side | Knee OA group Average (Standard deviation) | Healthy group Average (Standard deviation) | p-value |
|---|---|---|---|
| Gait cycle [s] | 1.06 (0.11) | 1.19 (0.08) | 0.020 |
| Stance ratio [%] | 54.9 (2.4) | 55.1 (1.4) | 0.833 |
| Angle between right and left knee joint tranjectory [°] | 7.4 (3.0) | 1.3 (2.1) | 0.000 |
| Direction of knee acceleration vector (at heel contact) [°] | 55.2 (8.9) | 61.0 (10.5) | 0.251 |

TABLE 20

| Lower severity side | Knee OA group Average (Standard deviation) | Healthy group Average (Standard deviation) | p-value |
|---|---|---|---|
| Step length [cm] | 51.1 (8.9) | 58.4 (3.9) | 0.059 |
| Max knee flexion angle in swing [°] | 87.8 (5.5) | 84.9 (5.5) | 0.308 |
| Max knee extension angle in stance [°] | 12.0 (4.7) | 13.3 (4.7) | 0.577 |
| Range of motion of knee joint [°] | 74.9 (5.1) | 71.0 (6.0) | 0.178 |
| Knee flexion angle (immediately after heel contact) [°] | 32.3 (8.4) | 27.7 (6.5) | 0.247 |
| Knee flexion angle (at the time of toe off) [°] | 62.7 (5.9) | 60.9 (4.0) | 0.502 |
| Ankle abduction angle [°] | 3.9 (5.2) | 6.8 (8.9) | 0.417 |
| Thigh and shank angle [°] | 178.4 (4.2) | 184.5 (8.0) | 0.068 |
| Lower limb functional axis inclination angle (abduction direction) [°] | −0.3 (2.4) | −2.4 (2.0) | 0.088 |
| Lower limb functional axis inclination angle (adduction direction) [°] | −8.3 (2.1) | −7.8 (1.0) | 0.513 |
| Gait cycle [s] | 1.07 (0.10) | 1.19 (0.08) | 0.019 |
| Stance ratio [%] | 54.8 (2.2) | 55.1 (1.4) | 0.737 |
| Angle between right and left knee joint tranjectory [°] | 7.2 (5.4) | 1.3 (2.1) | 0.014 |
| Direction of knee acceleration vector (at heel contact) [°] | 49.0 (8.9) | 61.0 (10.5) | 0.024 |

TABLE 21

| | | $a_x$ (m/sec$^2$) Average (Standard deviation) | p-value | $a_z$ (m/sec$^2$) Average (Standard deviation) | p-value | $a_{xz}$ (m/sec$^2$) Average (Standard deviation) | p-value |
|---|---|---|---|---|---|---|---|
| | Healthy group | 3.28 (0.73) | | 2.14 (0.43) | | 4.03 (0.54) | |
| Knee OA group | Leg with higher severity | 4.18 (1.88) | 0.243 | 1.81 (0.43) | 0.149 | 4.70 (1.63) | 0.304 |
| | Leg with lower severity | 4.77 (1.95) | 0.071 | 1.77 (0.38) | 0.084 | 5.16 (1.77) | 0.117 |

As a result, among the conventional gait parameters, a significant difference is observed only in the gait cycle and the step length with significance level of 5%. However, regarding the step length, the lower limb length largely varies between the patient group and the healthy group. Therefore, it can be said that a substantive difference is present in the gait cycle only. Given the above, it is impossible to early detect a disease, e.g., knee OA, or quantitatively assess the degree of progression using the conventional gait parameters only.

In contrast, the knee horizontal trajectory plane angle $\theta_{xy}$, a gait parameter calculated by the gait analysis system and the gait analysis method according to the present embodiment, exhibits a significant difference regarding both the right and left legs. In addition, although not exhibiting any significant difference regarding the right leg, the left leg, and the side with higher severity, the acceleration vector direction $\theta_{acc}$ exhibits a significant difference regarding the side with lower severity, enabling quantitative assessment of a disease, e.g., knee OA. The novel gait parameters are reviewed in detail below.

First, the knee horizontal plane trajectory of Patient B whose knee horizontal plane trajectory angle is the largest is reviewed as an example. In general, knee OA patients tend to have a reduced knee stability due to a reduction in articular cartilage. The instability becomes particularly a problem at the time of the heel contact at which a load applies and in the subsequent early stance phase, which is a load response phase. Referring to FIG. 31(d), it can be seen that the distance between the knee and the original point in the Y-direction is small at the time of the heel contact and in the early stance phase. This is presumably because the leg is brought closer to the original point, i.e., the gravity center position of the body, in order to make up for the instability of the knee. In the late stance phase, the load tends to decrease, and therefore the instability is less problematic. In the late stance phase, it is presumed that, in this case, the distance between the original point and the swinging knee becomes small in preparation for the heel contact on the opposite side and the distance with respect to the standing knee is large. Even the knee horizontal plane trajectory angles of the knee OA patients without knee pain differ from that of the healthy group. Therefore, it is reasonable to presume that the knee instability is the cause.

Next, the smaller angle $\theta_{acc}$ of the knee acceleration vector direction of the knee OA patients as compared with the healthy persons is presumably due to an increase in rearward component and a reduction in vertical component of the acceleration vector. The causes of an increase in rearward component presumably include the generation of velocity in the forward direction immediately before the heel contact. In general, knee OA patients tend to have a lower one-leg support ability than healthy persons. This is due to knee pain at the time of high loads or looseness of the knee. As a result of this, it is presumed that, in order to reduce the time for one leg support, the timing of the heel contact with the swing leg is advanced, the heel contact is made before the forward velocity of the swing leg, which was swung consequently, is reduced, and rearward acceleration occurs as if to apply a brake. As can be seen from FIGS. 30(b) and (c) or Table 20, this may also be inferred from the fact that the angle $\theta_{acc}$ of the knee acceleration vector direction is rather smaller on the side with lower severity than on the side with higher severity.

The reduction in vertical component is presumably due to a reduction in amount of displacement in the vertical direction due to a reduction in knee flexion angle. The knee flexion in the swing phase plays a role to ensure a clearance of the foot with respect to the ground. A reduction in knee flexion angle due to knee pain reduces the clearance. As a result, it is presumed that the movement of the leg in the vertical direction is reduced, and the velocity and the acceleration in the vertical direction are reduced.

Thus, it was found that angle $\theta_{acc}$ in the knee acceleration vector direction was reduced due to knee OA symptoms including knee pain, knee instability, and knee flexion restrictions.

Table 21 described below indicates results of a comparison of the acceleration of the ground coordinate system. The average values and the standard deviations of the rearward component $a_x$, the vertical component $a_z$, and their square-root of sum of squares $a_{xz}$ of the acceleration vector of the healthy group and the knee OA patient group are indicated. In addition, the p values in the Table are values at a time when an unpaired t-test was conducted. It can also be seen from the Table that the values $a_x$ and $a_{xz}$ are larger in the patient group and the value $a_z$ is smaller in the patient group.

Heretofore, the description has been given on the basis of the embodiment. However, the present invention is not limited to the aforementioned embodiment, but a change may be properly made within the scope of the claims. For example, in the aforementioned embodiment, an example of determining the novel gait parameters with regard to a knee joint was described. However, the present invention is not limited thereto, but the same parameters may be determined with regard to other lower limb joints, e.g., an ankle joint. In addition, in the aforementioned embodiment, the acceleration sensors and the angular velocity sensors are attached to both legs to acquire the gait parameters of both legs. However, the sensors may be attached to either one of the legs to calculate the gait parameters of only one leg.

INDUSTRIAL APPLICABILITY

Thus, according to the present invention, it becomes possible to develop the conventional three-dimensional gait analysis using an acceleration sensor and an angular velocity sensor to provide the gait analysis method and the gait analysis system that can obtain the novel gait parameters useful for assessment of the gait action of a subject.

REFERENCE SIGNS LIST 1 gait analysis system
3 sensor unit
4 marker
5 processing device
7 monitor screen
11 data acquisition portion
13 sensor posture estimation portion
15 segment posture computation portion
17 lower limb posture computation portion
19 gait parameter computation portion

What is claimed is:
1. A gait analysis method comprising:
attaching a tri-axial acceleration sensor and a tri-axial angular velocity sensor to lower limb portions across at least one joint of joints constituting at least one of lower limbs of a subject;
measuring acceleration and angular velocity of each lower limb portion with the tri-axial acceleration sensor and the tri-axial angular velocity sensor during gait of the subject;

calculating a posture of each lower limb portion during the gait based on the acceleration and the angular velocity measured;

constructing a three-dimensional model including a motion trajectory of the at least one joint; and calculating an angle of an acceleration vector of the at least one joint only at a time of heel contact with regard to the motion trajectory in a sagittal plane as a gait parameter.

2. The gait analysis method according to claim 1, wherein the at least one joint is a knee joint.

3. The gait analysis method according to claim 1, wherein the three-dimensional model including the motion trajectory of the at least one joint is constructed with regard to each of right and left lower limbs of the subject.

4. The gait analysis method according to claim 2, wherein the three-dimensional model including the motion trajectory of the at least one joint is constructed with regard to each of right and left lower limbs of the subject.

5. The gait analysis method according to claim 3, wherein an approximation straight line is formed with respect to each of motion trajectories of right and left joints in a horizontal plane, and an angle formed between the approximation straight lines is calculated as the gait parameter.

6. The gait analysis method according to claim 4, wherein an approximation straight line is formed with respect to each of motion trajectories of right and left joints in a horizontal plane, and an angle formed between the approximation straight lines is calculated as a-the gait parameter.

7. The gait analysis method according to claim 1, wherein a Lissajous figure of the at least one joint is created from the three- dimensional model, and the gait parameter is calculated based on the Lissajous figure.

8. The gait analysis method according to claim 2, wherein a Lissajous figure of the at least one joint is created from the three- dimensional model, and the gait parameter is calculated based on the Lissajous figure.

9. The gait analysis method according to claim 3, wherein a Lissajous figure of the at least one joint is created from the three-dimensional model, and the gait parameter is calculated based on the Lissajous figure.

10. The gait analysis method according to claim 4, wherein a Lissajous figure of the at least one joint is created from the three-dimensional model, and the gait parameter is calculated based on the Lissajous figure.

11. The gait analysis method according to claim 5, wherein a Lissajous figure of the at least one joint is created from the three- dimensional model, and the gait parameter is calculated based on the Lissajous figure.

12. The gait analysis method according to claim 6, wherein a Lissajous figure of the at least one joint is created from the three-dimensional model, and the gait parameter is calculated based on the Lissajous figure.

13. A gait analysis system comprising:

a tri-axial acceleration sensor and a tri-axial angular velocity sensor attached to lower limb portions across at least one joint of joints constituting at least one of lower limbs of a subject, the tri-axial acceleration sensor and the tri-axial angular velocity sensor measuring acceleration and angular velocity of each lower limb portion during gait of the subject; and a processing device that is configured to:

calculate a posture of each lower limb portion during the gait based on acceleration and angular velocity measured and constructing a three-dimensional model including a motion trajectory of the at least one joint; and calculate an angle of an acceleration vector of the at least one joint only at a time of heel contact with regard to the motion trajectory in a sagittal plane as a gait parameter.

14. The gait analysis system according to claim 13, wherein the tri-axial acceleration sensor and the tri-axial angular velocity sensor are attached to right and left lower limbs of the subject, and the processing device is configured to form an approximation straight line with respect to each of motion trajectories of right and left joints in a horizontal plane and calculate an angle formed between the approximation straight lines as the gait parameter.

15. The gait analysis system according to claim 13, wherein the processing device is configured to create a Lissajous figure of the at least one joint from the three-dimensional model and calculate the gait parameter based on the Lissajous figure.

16. The gait analysis system according to claim 14, wherein the processing device is configured to create a Lissajous figure of the at least one joint from the three-dimensional model and calculate the gait parameter based on the Lissajous figure.

* * * * *